(12) United States Patent
Sterrett et al.

(10) Patent No.: US 11,642,064 B2
(45) Date of Patent: May 9, 2023

(54) HIGH DENSITY ELECTRODE MAPPING CATHETER

(71) Applicant: St. Jude Medical, Cardiology Division, Inc., St. Paul, MN (US)

(72) Inventors: Terry L. Sterrett, Huntington Beach, CA (US); John J. Crow, San Diego, CA (US); Eric Lim, Tustin, CA (US); Gregory K. Olson, Elk River, MN (US); Jeffrey A. Schweitzer, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 596 days.

(21) Appl. No.: 16/781,499

(22) Filed: Feb. 4, 2020

(65) Prior Publication Data
US 2020/0229726 A1 Jul. 23, 2020

Related U.S. Application Data

(63) Continuation of application No. 15/331,562, filed on Oct. 21, 2016, now Pat. No. 10,595,738.
(Continued)

(51) Int. Cl.
*H05K 3/14* (2006.01)
*H05K 3/06* (2006.01)
(Continued)

(52) U.S. Cl.
CPC .............. *A61B 5/287* (2021.01); *A61B 5/283* (2021.01); *A61B 5/6858* (2013.01); *A61B 18/14* (2013.01);
(Continued)

(58) Field of Classification Search
CPC ..... A61B 5/287; A61B 18/14; A61B 18/1492; A61B 2017/00526; A61B 2562/125; A61B 2562/222; H05K 3/06; H05K 3/143
See application file for complete search history.

(56) References Cited

U.S. PATENT DOCUMENTS 4,522,212 A   6/1985  Gelinas et al.
5,224,939 A   7/1993  Holman et al.
(Continued)

FOREIGN PATENT DOCUMENTS

AU   2015202258 A1   5/2015
AU   2016204351 A1   1/2017
(Continued)

OTHER PUBLICATIONS

Rao, Chepuri R.K. and Trivedi, D.C., Chemical and electrochemical depositions of platinum group metals and their applications, Coordination Chemistry Reviews, 249, (2005) pp. 613-631 ([copy provided in parent U.S. Appl. No. 15/331,562].
(Continued)

*Primary Examiner* — Peter Dungba Vo
*Assistant Examiner* — Jose K Abraham
(74) *Attorney, Agent, or Firm* — Kilpatrick Townsend & Stockton LLP

(57) ABSTRACT

An integrated electrode structure can comprise a catheter shaft comprising a proximal end and a distal end, the catheter shaft defining a catheter shaft longitudinal axis. A flexible tip portion can be located adjacent to the distal end of the catheter shaft, the flexible tip portion comprising a flexible framework. A plurality of microelectrodes can be disposed on the flexible framework and can form a flexible array of microelectrodes adapted to conform to tissue. A plurality of conductive traces can be disposed on the flexible framework, each of the plurality of conductive traces can be
(Continued)

electrically coupled with a respective one of the plurality of microelectrodes.

17 Claims, 53 Drawing Sheets

Related U.S. Application Data

(60) Provisional application No. 62/324,067, filed on Apr. 18, 2016, provisional application No. 62/244,565, filed on Oct. 21, 2015.

(51) Int. Cl.
  *A61B 5/287* (2021.01)
  *A61B 5/00* (2006.01)
  *A61B 18/14* (2006.01)
  *A61N 1/362* (2006.01)
  *A61B 5/283* (2021.01)
  *A61B 17/00* (2006.01)
  *A61B 18/00* (2006.01)

(52) U.S. Cl.
  CPC .......... *A61B 18/1492* (2013.01); *A61N 1/362* (2013.01); *H05K 3/06* (2013.01); *H05K 3/143* (2013.01); *A61B 2017/00526* (2013.01); *A61B 2018/00267* (2013.01); *A61B 2018/00351* (2013.01); *A61B 2018/00357* (2013.01); *A61B 2018/00577* (2013.01); *A61B 2018/00839* (2013.01); *A61B 2562/028* (2013.01); *A61B 2562/125* (2013.01); *A61B 2562/222* (2013.01)

(56) References Cited

U.S. PATENT DOCUMENTS

| | | | |
|---|---|---|---|
| 5,380,301 A | 1/1995 | Prichard et al. |
| 5,400,783 A | 3/1995 | Pomeranz et al. |
| 5,456,254 A | 10/1995 | Pietroski et al. |
| 5,465,717 A | 11/1995 | Imran et al. |
| 5,626,136 A | 5/1997 | Webster, Jr. |
| 5,702,438 A | 12/1997 | Avitall |
| 5,715,817 A | 2/1998 | Stevens-Wright et al. |
| 5,715,832 A | 2/1998 | Koblish et al. |
| 5,827,278 A | 10/1998 | Webster, Jr. |
| 5,876,373 A | 3/1999 | Giba et al. |
| 5,964,757 A | 10/1999 | Ponzi |
| 6,029,091 A | 2/2000 | de la Rama et al. |
| 6,071,282 A | 6/2000 | Fleischman |
| 6,074,379 A | 6/2000 | Prichard |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,273,404 B1 | 8/2001 | Holman et al. |
| 6,415,187 B1 | 7/2002 | Kuzma et al. |
| 6,491,681 B1 | 12/2002 | Kunis et al. |
| 6,522,932 B1 | 2/2003 | Kuzma et al. |
| 6,554,794 B1 | 4/2003 | Mueller et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,004,937 B2 | 2/2006 | Lentz et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,214,220 B2 | 5/2007 | McGlinch et al. |
| 7,217,256 B2 | 5/2007 | Di Palma |
| 7,228,164 B2 | 6/2007 | Fuimaono et al. |
| 7,257,435 B2 | 8/2007 | Plaza |
| 7,360,293 B2 * | 4/2008 | Sato ............... G06V 40/1306 29/595 |
| 7,412,274 B2 | 8/2008 | Mejia |
| 7,429,261 B2 | 9/2008 | Kunis et al. |
| 7,561,907 B2 | 7/2009 | Fuimaono et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,157,848 B2 | 4/2012 | Zhang et al. |
| 8,221,390 B2 | 7/2012 | Pal et al. |
| 8,271,099 B1 | 9/2012 | Swanson |
| 8,273,016 B2 | 9/2012 | O'sullivan |
| 8,295,902 B2 | 10/2012 | Salahieh et al. |
| 8,364,234 B2 | 1/2013 | Kordis et al. |
| 8,376,990 B2 | 2/2013 | Ponzi et al. |
| 8,391,947 B2 | 3/2013 | Urman et al. |
| 8,447,377 B2 | 5/2013 | Harlev et al. |
| 8,486,063 B2 | 7/2013 | Werneth et al. |
| 8,560,086 B2 | 10/2013 | Just et al. |
| 8,565,894 B2 | 10/2013 | Vetter et al. |
| 8,603,069 B2 | 12/2013 | Selkee |
| 8,608,703 B2 | 12/2013 | Riles et al. |
| 8,649,880 B1 | 2/2014 | Parker, Jr. |
| 8,696,917 B2 * | 4/2014 | Petisce ............... A61B 5/415 216/36 |
| 8,700,120 B2 | 4/2014 | Koblish |
| 8,706,193 B2 | 4/2014 | Govari et al. |
| 8,744,599 B2 | 6/2014 | Tegg |
| 8,755,861 B2 | 6/2014 | Harlev et al. |
| 8,777,929 B2 | 7/2014 | Schneider et al. |
| 8,792,962 B2 | 7/2014 | Esguerra et al. |
| 8,795,504 B2 | 8/2014 | Petrossians et al. |
| 8,814,824 B2 | 8/2014 | Kauphusman et al. |
| 8,814,825 B2 | 8/2014 | Tegg et al. |
| 8,880,158 B2 | 11/2014 | Spector |
| 8,882,705 B2 | 11/2014 | McDaniel et al. |
| 8,894,610 B2 | 11/2014 | Macnamara et al. |
| 8,996,091 B2 | 3/2015 | de la Rama et al. |
| 9,017,308 B2 | 4/2015 | Klisch et al. |
| 9,033,893 B2 | 5/2015 | Spector |
| 9,033,917 B2 | 5/2015 | Magana et al. |
| 9,044,245 B2 | 6/2015 | Condie et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,254,093 B2 | 2/2016 | Spector |
| 9,282,908 B2 | 3/2016 | Spector |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,474,894 B2 | 10/2016 | Mercanzini et al. |
| 9,486,280 B2 | 11/2016 | Koblish et al. |
| 9,486,282 B2 | 11/2016 | Solis |
| 9,532,703 B2 | 1/2017 | Huszar et al. |
| 9,539,413 B2 | 1/2017 | Ogle |
| 9,649,158 B2 | 5/2017 | Datta et al. |
| 9,687,166 B2 | 6/2017 | Subramaniam et al. |
| 9,693,699 B2 | 7/2017 | Spector et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,706,935 B2 | 7/2017 | Spector |
| 9,713,418 B2 | 7/2017 | Huszar et al. |
| 9,788,895 B2 | 10/2017 | Solis |
| 9,820,664 B2 | 11/2017 | Hotlink et al. |
| 9,833,608 B2 | 12/2017 | Masson |
| 9,844,645 B2 | 12/2017 | Pai et al. |
| 9,848,795 B2 | 12/2017 | Marecki et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |

(56) References Cited

U.S. PATENT DOCUMENTS

| | | |
|---|---|---|
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,143,394 B2 | 12/2018 | Solis |
| 10,322,261 B2 | 6/2019 | Pai et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,476 B2 | 2/2021 | Spector |
| 10,912,925 B2 | 2/2021 | Houck |
| 10,966,623 B2 | 4/2021 | Wu et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,089,987 B2 | 8/2021 | Spector |
| 11,116,436 B2 | 9/2021 | Wu et al. |
| 11,141,568 B2 | 10/2021 | Hsueh et al. |
| 11,160,482 B2 | 11/2021 | Solis |
| 11,272,886 B2 | 3/2022 | Harlev et al. |
| 2002/0165484 A1 | 11/2002 | Bowe et al. |
| 2003/0093069 A1 | 5/2003 | Panescu et al. |
| 2003/0100895 A1* | 5/2003 | Simpson ............ A61B 18/1492 606/41 |
| 2005/0159741 A1 | 7/2005 | Paul et al. |
| 2007/0083193 A1* | 4/2007 | Werneth ............... A61B 5/7445 606/41 |
| 2008/0108221 A1* | 5/2008 | Kim .................... C25D 7/123 438/652 |
| 2008/0140152 A1 | 6/2008 | Imran et al. |
| 2008/0312521 A1 | 12/2008 | Solomon |
| 2009/0149848 A1 | 6/2009 | Werneth et al. |
| 2009/0171274 A1 | 7/2009 | Harlev et al. |
| 2009/0198300 A1 | 8/2009 | Zhang et al. |
| 2011/0118726 A1 | 5/2011 | de la Rama et al. |
| 2012/0271302 A1 | 10/2012 | Behl et al. |
| 2012/0296232 A1 | 11/2012 | Ng |
| 2013/0126224 A1* | 5/2013 | Kim ..................... H05K 3/3452 174/262 |
| 2013/0253504 A1 | 9/2013 | Fang |
| 2013/0274582 A1 | 10/2013 | Afonso et al. |
| 2014/0100639 A1 | 4/2014 | Lee et al. |
| 2014/0142408 A1 | 5/2014 | de la Rama et al. |
| 2014/0166612 A1* | 6/2014 | Petisce ................. B32B 37/025 216/13 |
| 2014/0182887 A1* | 7/2014 | Yoshioka ............ H01L 25/0655 174/250 |
| 2014/0200639 A1 | 7/2014 | de la Rama |
| 2014/0238175 A1 | 8/2014 | Huszar et al. |
| 2014/0269602 A1 | 9/2014 | Kawagishi |
| 2014/0288552 A1 | 9/2014 | Kunis et al. |
| 2014/0296846 A1 | 10/2014 | Huszar et al. |
| 2014/0296849 A1 | 10/2014 | Coe et al. |
| 2014/0296902 A1 | 10/2014 | Huszar et al. |
| 2014/0316496 A1 | 10/2014 | Masson et al. |
| 2014/0336636 A1 | 11/2014 | Huszar et al. |
| 2014/0350564 A1 | 11/2014 | Huszar et al. |
| 2015/0080883 A1 | 3/2015 | Haverkost et al. |
| 2015/0105645 A1 | 4/2015 | Subramaniam et al. |
| 2015/0119911 A1 | 4/2015 | Mckenzie |
| 2015/0141785 A1 | 5/2015 | Hayam et al. |
| 2015/0159741 A1 | 6/2015 | Versteyhe et al. |
| 2015/0276651 A1* | 10/2015 | Petisce ............... G01N 27/3272 216/13 |
| 2015/0296626 A1* | 10/2015 | Greenberg ........... H05K 3/0011 216/13 |
| 2015/0351652 A1* | 12/2015 | Marecki ............. A61B 18/1492 29/829 |
| 2015/0366508 A1* | 12/2015 | Chou ..................... A61B 5/287 600/467 |
| 2016/0059004 A1 | 3/2016 | Mercanzini et al. |
| 2016/0143588 A1 | 5/2016 | Hoitink et al. |
| 2016/0184041 A1* | 6/2016 | Gafford ................. A61B 34/72 606/174 |
| 2016/0213423 A1 | 7/2016 | Kauphusman et al. |
| 2016/0213916 A1 | 7/2016 | de la Rama |
| 2016/0228696 A1* | 8/2016 | Imran .................. A61N 1/0553 |
| 2016/0278851 A1 | 9/2016 | Mannion et al. |
| 2016/0317094 A1 | 11/2016 | Byrd et al. |
| 2016/0331471 A1 | 11/2016 | Deno et al. |
| 2016/0331933 A1 | 11/2016 | Knutsen |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | de la Rama et al. |
| 2017/0112405 A1 | 4/2017 | Sterrett et al. |
| 2018/0042667 A1 | 2/2018 | Pappone et al. |
| 2018/0050190 A1 | 2/2018 | Masson |
| 2018/0056038 A1 | 3/2018 | Aujla |
| 2018/0070845 A1 | 3/2018 | Hoitink et al. |
| 2018/0235496 A1 | 8/2018 | Wu et al. |
| 2018/0303361 A1 | 10/2018 | Wu et al. |
| 2019/0175043 A1 | 6/2019 | Wu et al. |
| 2020/0077912 A1 | 3/2020 | Wu et al. |
| 2020/0138319 A1 | 5/2020 | Spector |
| 2020/0138378 A1 | 5/2020 | de la Rama et al. |
| 2020/0155021 A1 | 5/2020 | Wu et al. |
| 2020/0221966 A1 | 7/2020 | Wu et al. |
| 2020/0229727 A1 | 7/2020 | Hoitink et al. |
| 2020/0253496 A1 | 8/2020 | Deno et al. |
| 2020/0405166 A1 | 12/2020 | Wu et al. |
| 2021/0145342 A1 | 5/2021 | Wang |
| 2021/0187246 A1 | 6/2021 | Houck |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0015678 A1 | 1/2022 | Spector |
| 2022/0023594 A1 | 1/2022 | Pai |
| 2022/0054066 A1 | 2/2022 | Solis |
| 2022/0175294 A1 | 6/2022 | Spector |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101351162 A | 1/2009 |
| CN | 101797181 A | 8/2010 |
| CN | 103687538 A | 3/2014 |
| CN | 101927053 B | 1/2015 |
| CN | 103157168 B | 4/2015 |
| CN | 104968261 A | 10/2015 |
| CN | 105960201 A | 9/2016 |
| CN | 106264715 A | 1/2017 |
| CN | 106264716 A | 1/2017 |
| CN | 106308790 A | 1/2017 |
| CN | 104958824 B | 12/2018 |

(56) References Cited

FOREIGN PATENT DOCUMENTS

| | | |
|---|---|---|
| CN | 104434083 B | 4/2019 |
| CN | 104968261 B | 5/2019 |
| CN | 105592778 B | 7/2019 |
| CN | 106264715 B | 11/2020 |
| CN | 106264716 B | 11/2020 |
| CN | 106308790 B | 6/2021 |
| CN | 107529958 B | 7/2021 |
| CN | 110559544 B | 9/2021 |
| CN | 105615994 B | 10/2021 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2249919 | 11/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |
| EP | 2732843 A1 | 5/2014 |
| EP | 2747680 A2 | 7/2014 |
| EP | 2752153 A1 | 7/2014 |
| EP | 2792322 A1 | 10/2014 |
| EP | 2792323 A1 | 10/2014 |
| EP | 2796103 A1 | 10/2014 |
| EP | 2907462 A1 | 8/2015 |
| EP | 2915555 A1 | 9/2015 |
| EP | 3023052 A | 5/2016 |
| EP | 1968679 B1 | 9/2016 |
| EP | 2241279 B1 | 9/2016 |
| EP | 3111871 A1 | 1/2017 |
| EP | 3111872 A1 | 1/2017 |
| EP | 3114987 A1 | 1/2017 |
| EP | 2796103 B1 | 2/2017 |
| EP | 2792322 B1 | 10/2017 |
| EP | 2792323 B1 | 10/2017 |
| EP | 3115076 A4 | 10/2017 |
| EP | 3117863 A4 | 10/2017 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3466363 A1 | 4/2019 |
| EP | 2550989 B1 | 6/2019 |
| EP | 3527125 A1 | 8/2019 |
| EP | 3434218 B1 | 2/2020 |
| EP | 2908723 | 3/2020 |
| EP | 3114987 B1 | 8/2020 |
| EP | 3738508 A1 | 11/2020 |
| EP | 3738509 A1 | 11/2020 |
| EP | 3750475 A1 | 12/2020 |
| EP | 2155301 B1 | 4/2021 |
| EP | 2809254 B1 | 6/2021 |
| IL | 246415 B | 12/2019 |
| IN | 201614021431 A | 12/2016 |
| IN | 201614021432 A | 12/2016 |
| IN | 201614021450 A | 12/2016 |
| JP | 4545384 B2 | 7/2010 |
| JP | 2011512991 | 4/2011 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 2017012750 A | 1/2017 |
| JP | 2017012755 A | 1/2017 |
| JP | 2017038919 A | 2/2017 |
| JP | 2017051211 A | 3/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6466114 B2 | 2/2019 |
| JP | 6515084 B2 | 4/2019 |
| JP | 6655655 B2 | 2/2020 |
| JP | 6776021 B2 | 10/2020 |
| JP | 6786275 B2 | 11/2020 |
| JP | 2021007772 A | 1/2021 |
| JP | 6843502 B2 | 3/2021 |
| JP | 6926306 B2 | 8/2021 |
| JP | 6932484 B2 | 8/2021 |
| JP | 6980386 B2 | 11/2021 |
| JP | 2022020838 A | 2/2022 |
| RU | 2016124794 A | 12/2017 |
| RU | 2016124801 A | 12/2017 |
| RU | 2016125763 A | 1/2018 |
| WO | 9843530 A1 | 10/1998 |
| WO | 0168178 A1 | 9/2001 |
| WO | 2005114720 A2 | 12/2005 |
| WO | 2008091197 A | 7/2008 |
| WO | 2008157399 A1 | 12/2008 |
| WO | 2013028998 | 2/2013 |
| WO | 2014113612 A1 | 7/2014 |
| WO | 2015002787 A1 | 1/2015 |
| WO | 2015057521 A1 | 4/2015 |
| WO | 2015095577 A1 | 6/2015 |
| WO | 2015130824 A1 | 9/2015 |
| WO | 2015187430 A2 | 12/2015 |
| WO | 2016001015 A1 | 1/2016 |
| WO | 2016090175 A1 | 6/2016 |
| WO | 2018106496 | 6/2018 |
| WO | 2020113137 | 6/2020 |

OTHER PUBLICATIONS

Sheela G., et al., Electrodeposition of Iridium, Bulletin of Electrochemistry, 15 (5-6) May-Jun. 1999, pp. 208-210 [copy provided in parent U.S. Appl. No. 15/331,562].

Wu, Feng, et al., Electrodeposition of Platinum-Iridium Alloy on Nickel-Base Single-Crystal Superalloy TMS75, Surface and Coatings Technology vol. 184, Issue 1, Jun. 1, 2004 [copy provided in parent U.S. Appl. No. 15/331,562].

Baumgartner, M.E. and Raub, CH. J., The Electrodeposition of Platinum and Platinum Alloys, Platinum Metals Review, 1988, 32, (4), 188-197 [copy provided in parent U.S. Appl. No. 15/331,562].

Ohno, Izumi, Electroless Deposition of Palladium and Platinum, Modern Electroplating, 5th Edition, Edited by Mordechay Schlesinger and Milan Paunovic, Copyright 2010, John Wiley & Sons, Inc. Chp 20, 477-482 [copy provided in parent U.S. Appl. No. 15/331,562].

Electroplating the Platinum Metals—A Recent Survey of Processes and Applications, Platinum Metals Rev., 1970, 14, (3) pp. 93-94 [copy provided in parent U.S. Appl. No. 15/331,562].

Yingna Wu et al., Characterization of Electroplated Platinum-Iridium Alloys on the Nickel-Base Single Crystal Superalloy, Materials Transactions, vol. 46, No. 10 (2005) pp. 2176-2179 [copy provided in parent U.S. Appl. No. 15/331,562].

Anton Georgiev et al., "Chemical and Physical Properties of Polyimides: Biomedical and Engineering Applications", High Performance Polymers—Polyimides Based—From Chemistry to Applications, InTech, (Dec. 19, 2012), Chapter 4, pp. 1-20, doi:10.5772/53918.

* cited by examiner

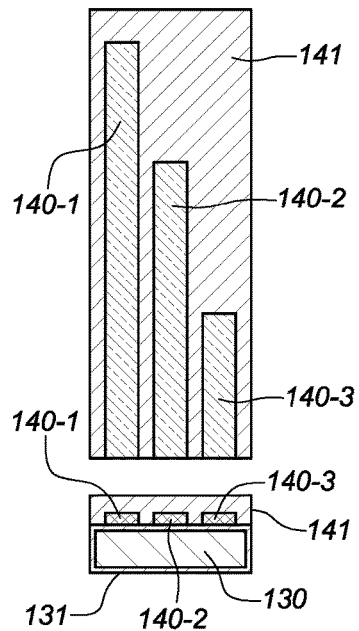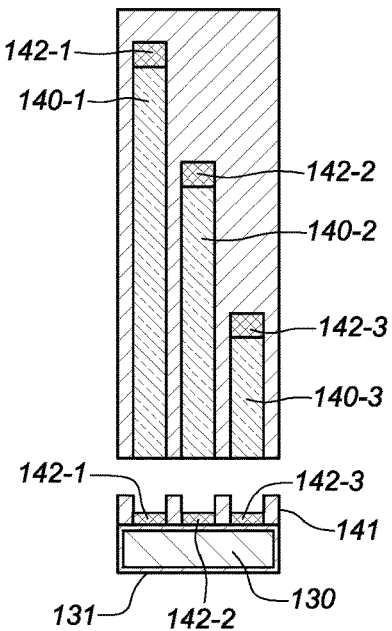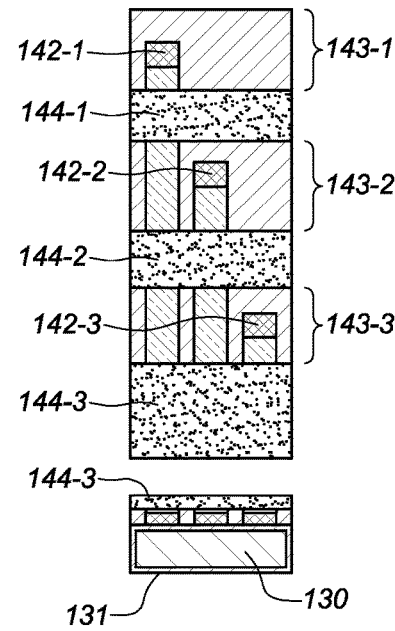
FIG. 3F   FIG. 3G   FIG. 3H
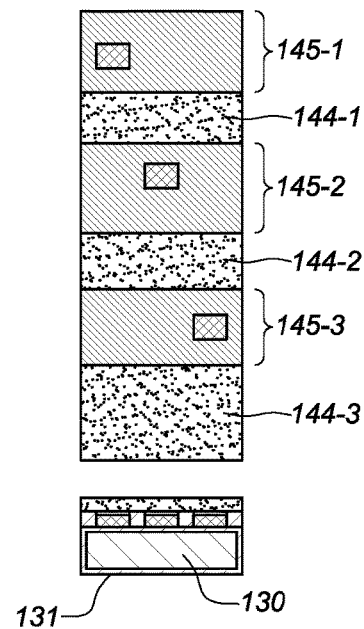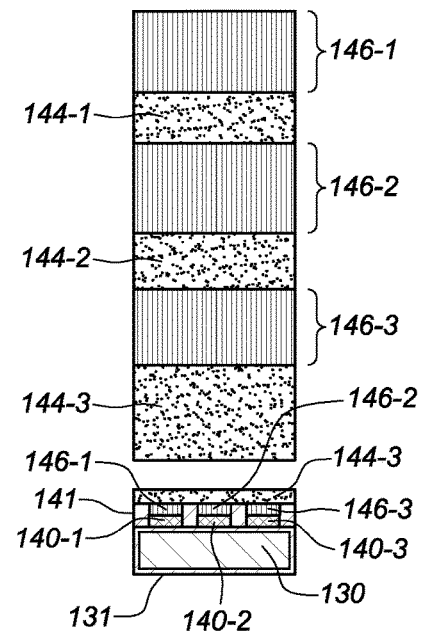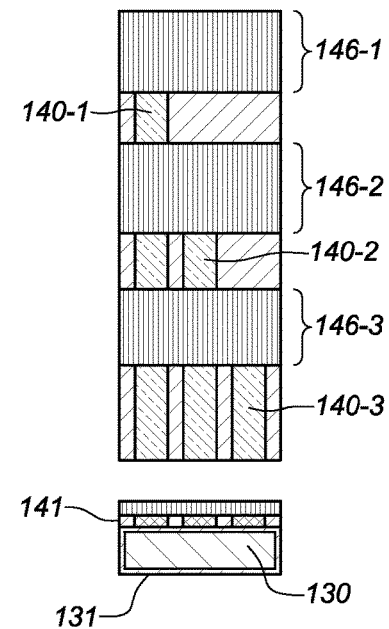
FIG. 3I   FIG. 3J   FIG. 3K

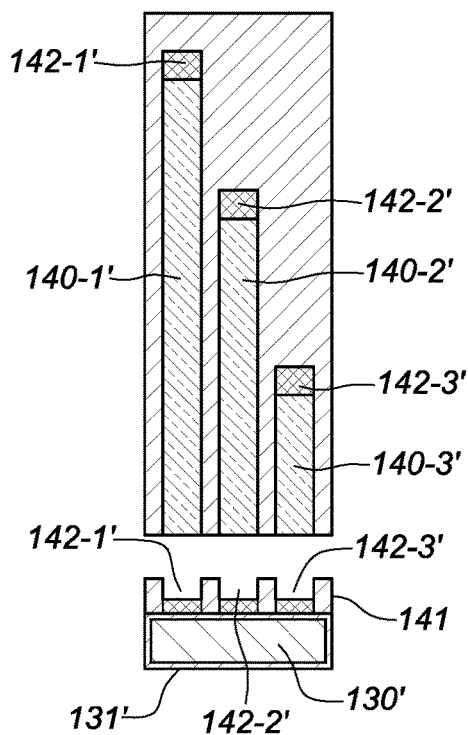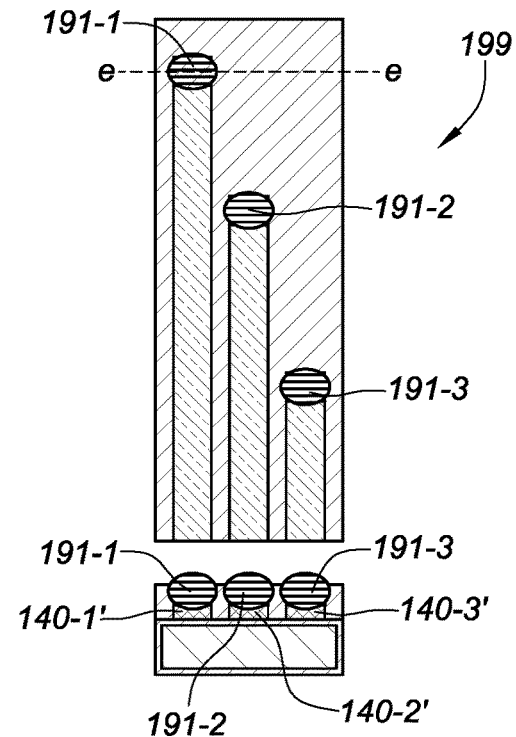
FIG. 6A  FIG. 6B
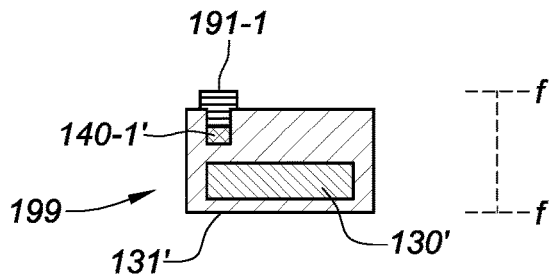
FIG. 6C
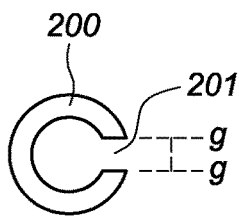 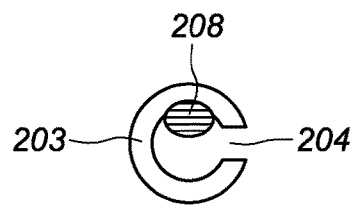 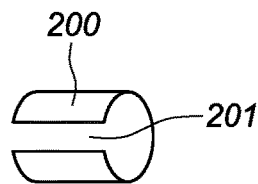
FIG. 6D  FIG. 6E  FIG. 6F

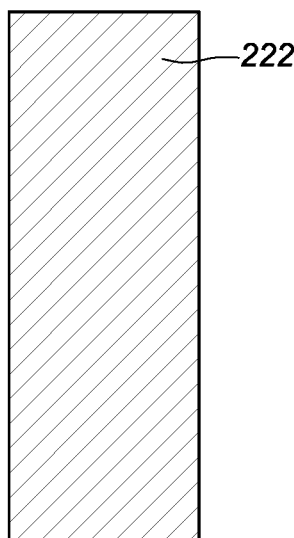
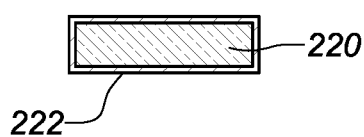
FIG. 7A
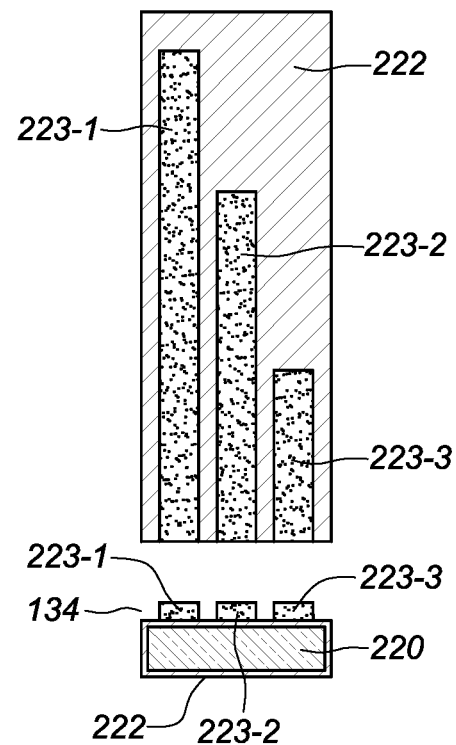
FIG. 7B
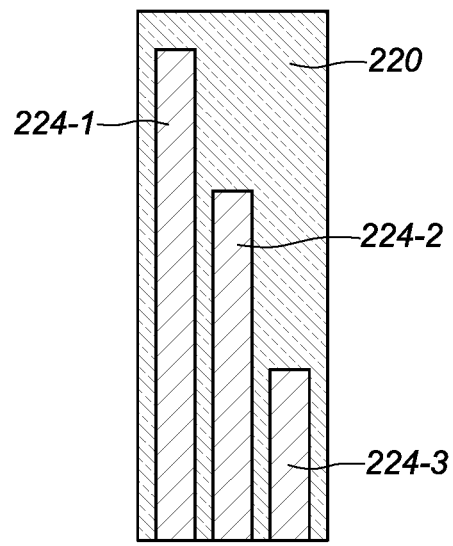
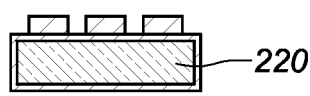
FIG. 7C

| material | modulus - E | | ultimate tensile strength | | loading plateau | | flexural strength | |
|---|---|---|---|---|---|---|---|---|
| | E (GPa) | E (ksi) | $\sigma_{ULT}$ (GPa) | $\sigma_{ULT}$ (ksi) | $\sigma_{LP}$ (GPa) | $\sigma_{LP}$ (ksi) | $\sigma_{FLX}$ (GPa) | $\sigma_{FLX}$ (ksi) |
| NDC super elastic Nitinol | 75 | 10878 | 1.070 | 155 | 0.380 | 55 | --- | --- |
| JM NiTi (Cu doped) | --- | --- | 1.517 | 220 | 0.448 | 65 | --- | --- |
| Fort Wayne Metals | 75 | 10878 | 1.310 | 190 | 0.517 | 75 | --- | --- |
| Euroflex | 75 | 10878 | 1.100 | 160 | 0.380 | 55 | --- | --- |
| Rogers Ultralam 3850HT (LCP) | 4.047 | 587 | n/a | n/a | n/a | n/a | 0.206 | 30 |
| Rogers RT/duroid 5870/5880 | 1.28 | 186 | n/a | n/a | n/a | n/a | 0.042 | 6.1 |
| FR4 - FFI Report 10Jan2014 | 20 | 2901 | n/a | n/a | n/a | n/a | 0.500 | 73 |
| FR4 - ASTM typical | 20 | 2901 | n/a | n/a | n/a | n/a | 0.430 | 62 |
| BT - Isola G200 | 24 | 3489 | 0.355 | 51.5 | n/a | n/a | 0.600 | 87 |
| BT - Nelco N5000-32 | 23 | 3400 | --- | --- | n/a | n/a | --- | --- |

*FIG. 11*

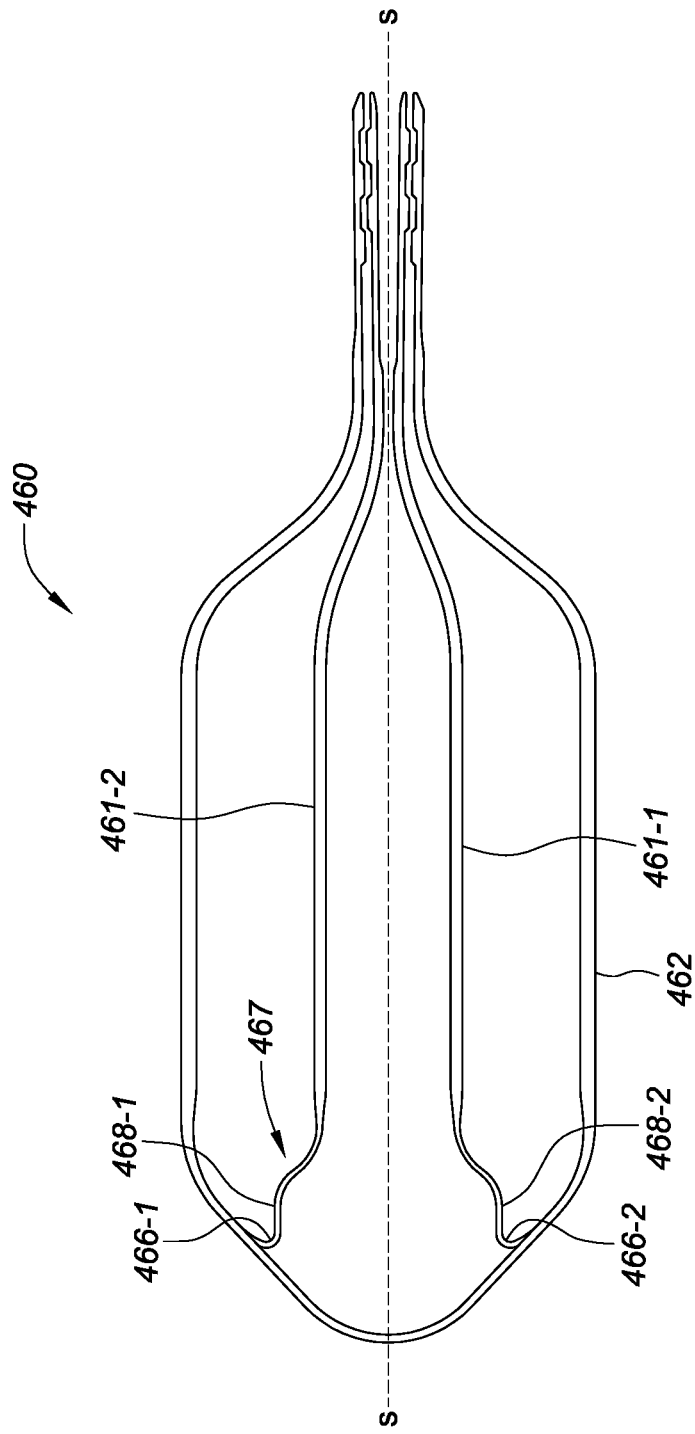

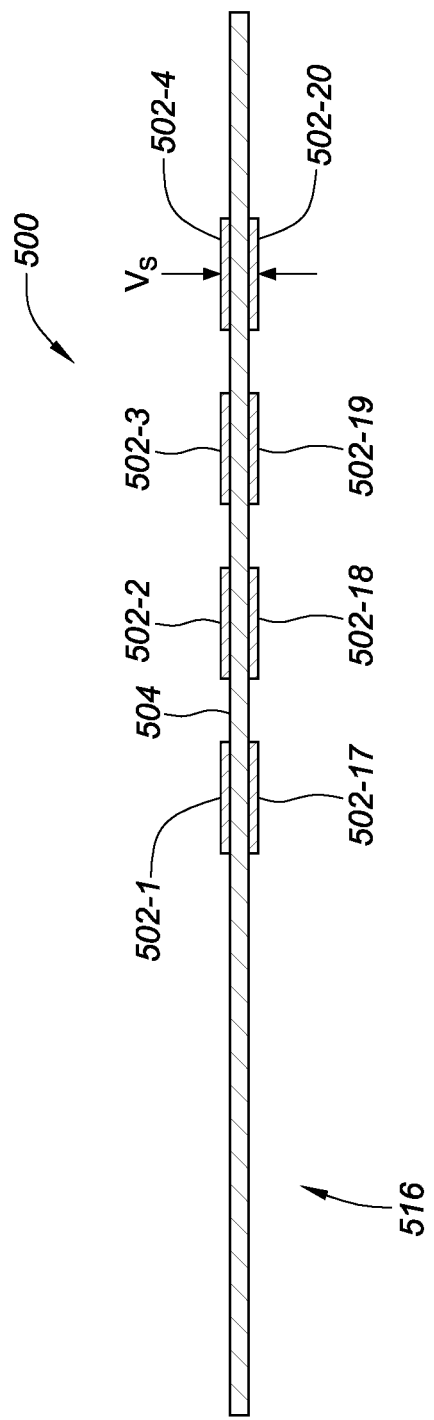

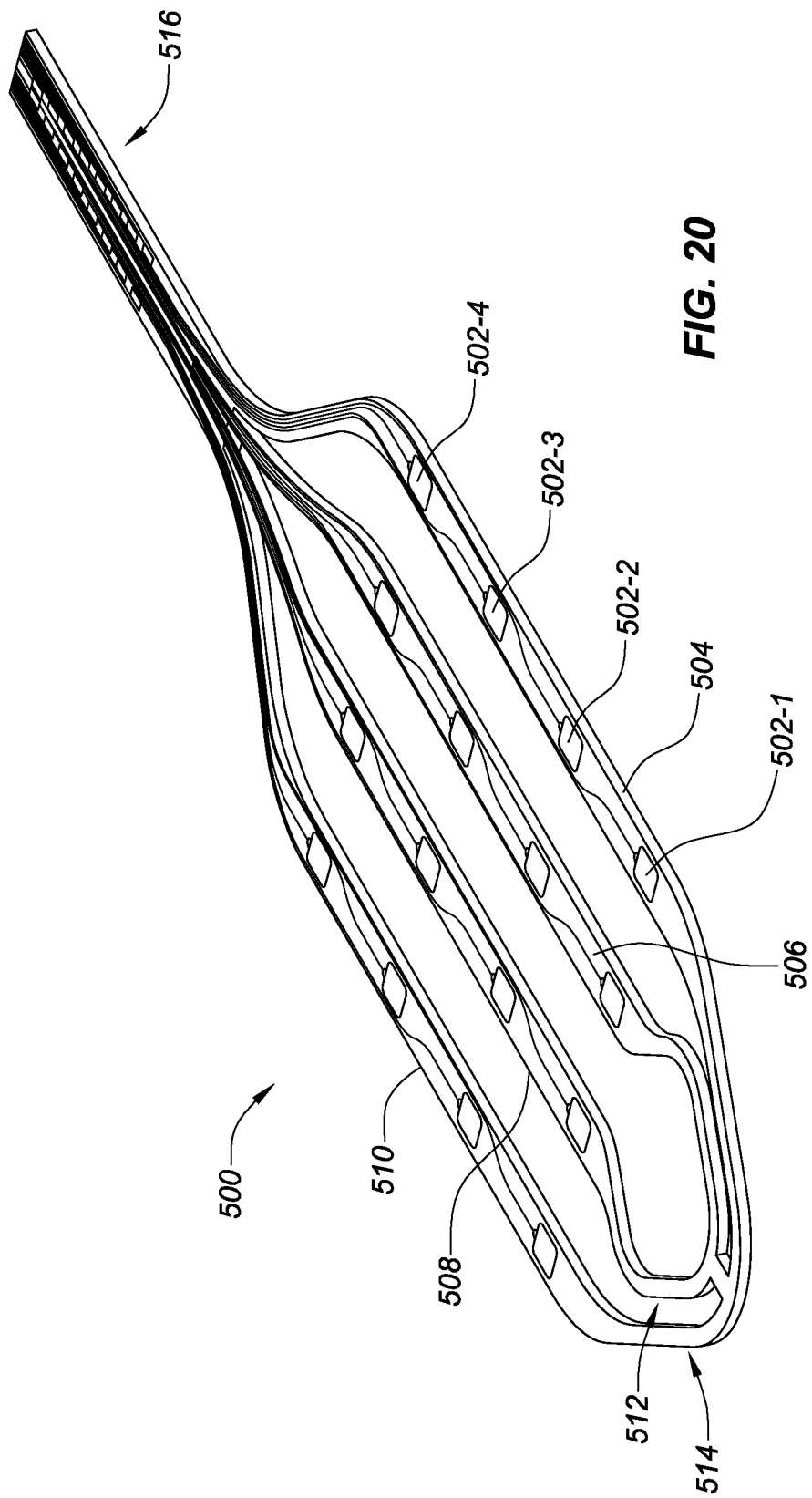

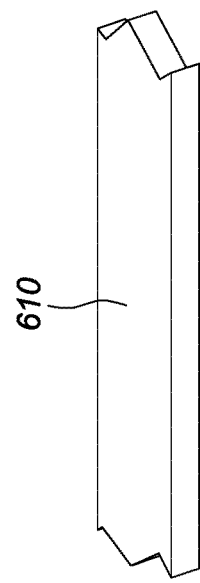
FIG. 23A
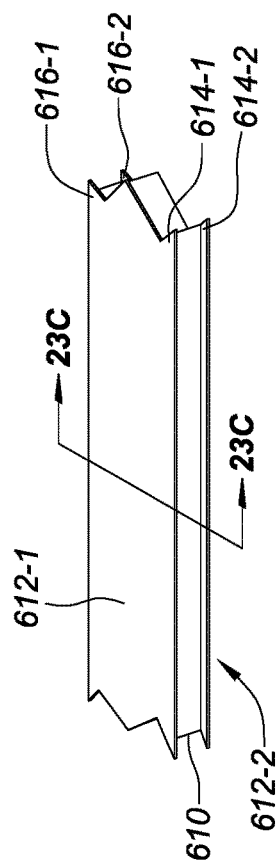
FIG. 23B
FIG. 23C
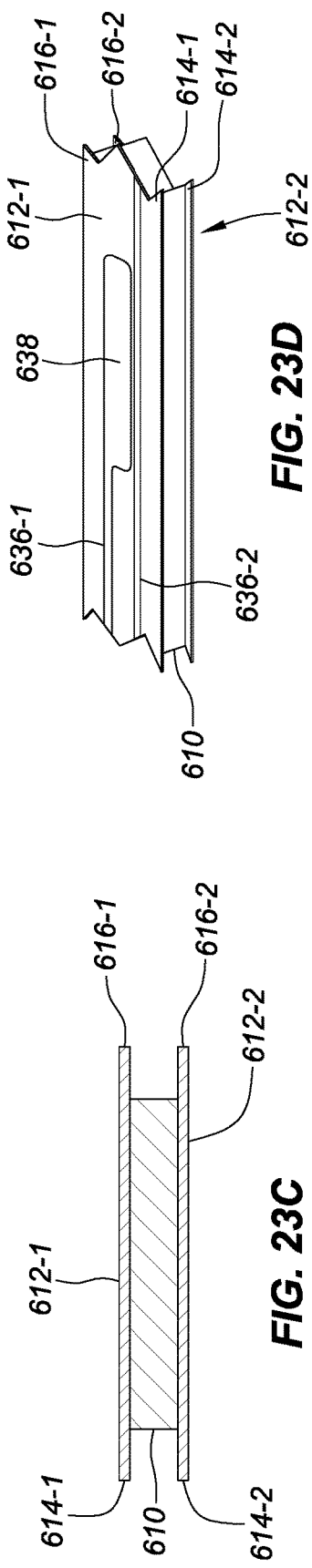
FIG. 23D
FIG. 23E
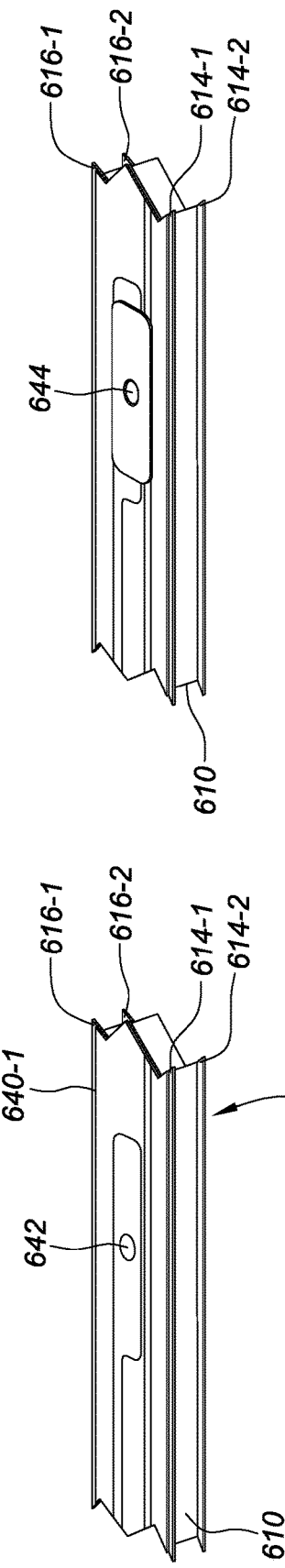
FIG. 23F

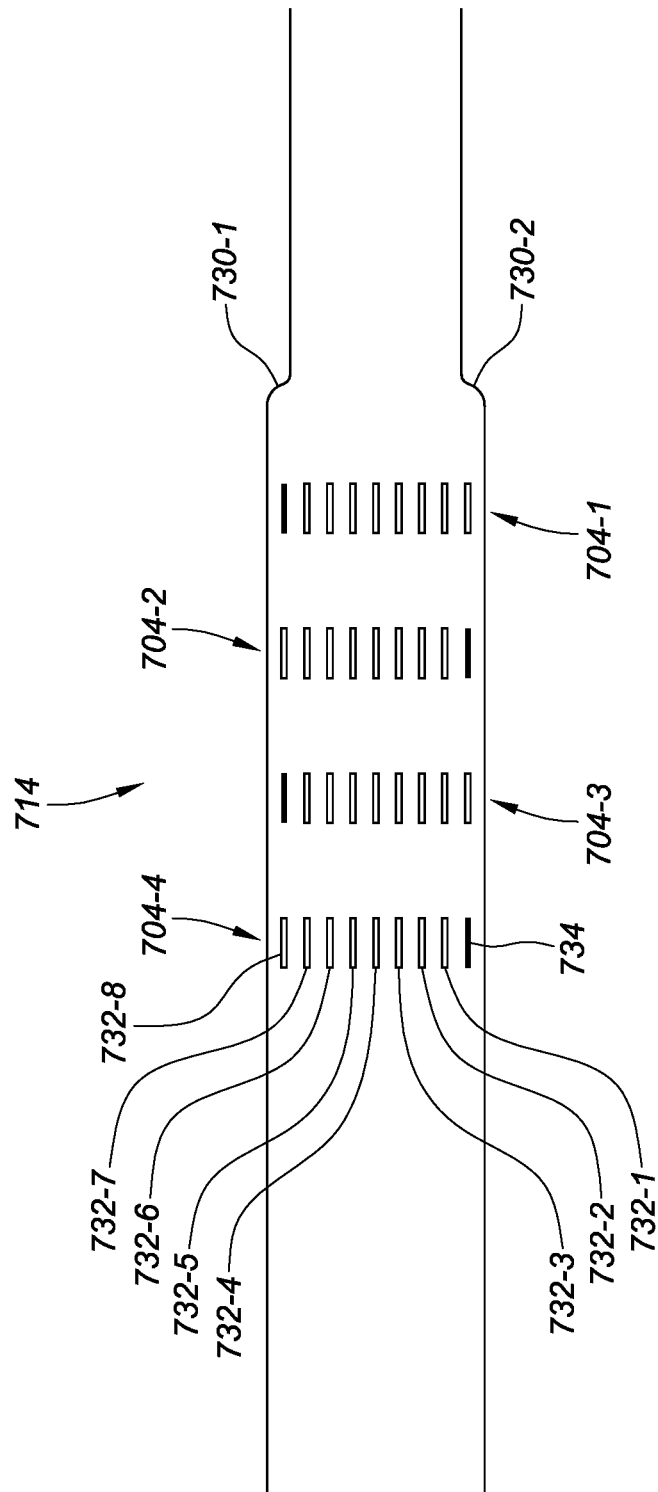

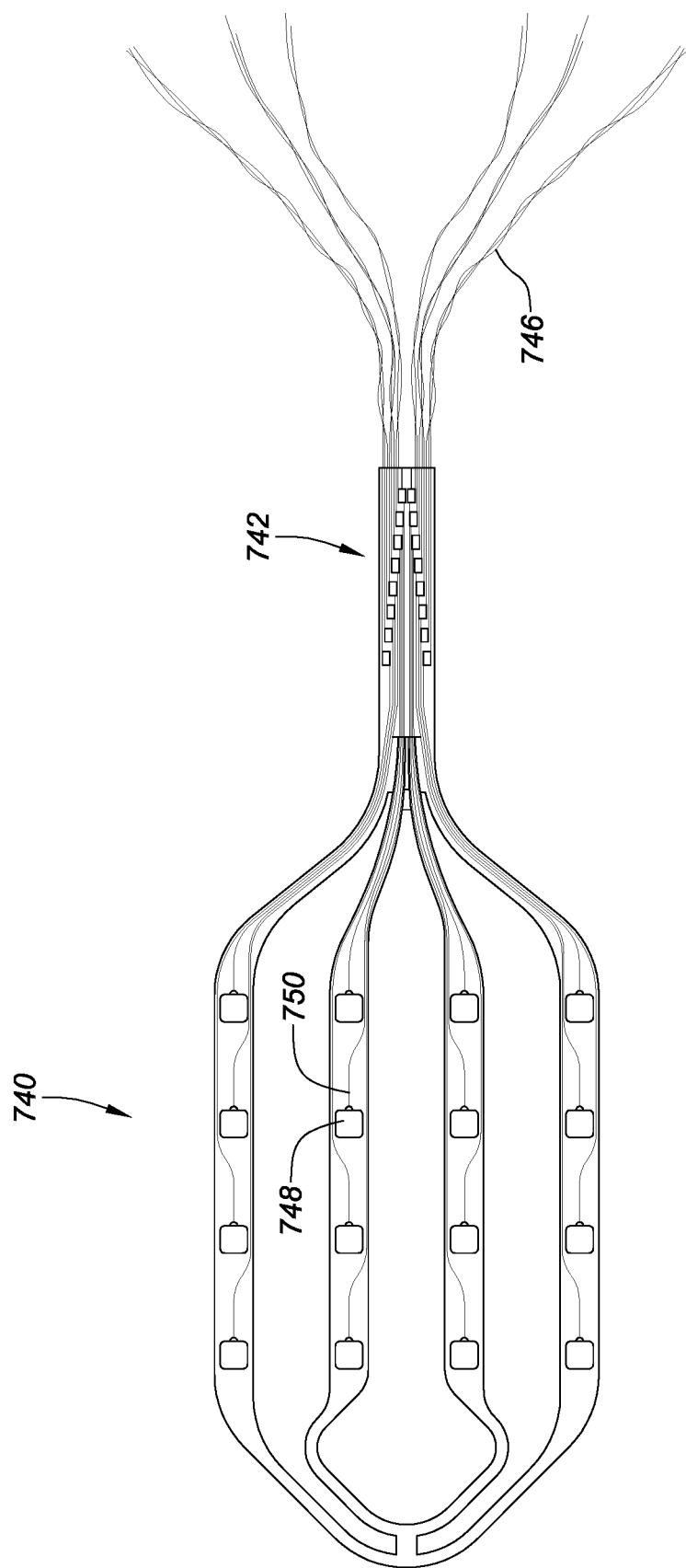

HIGH DENSITY ELECTRODE MAPPING CATHETER

CROSS-REFERENCE TO RELATED APPLICATION

This application is a continuation of U.S. application Ser. No. 15/331,562, filed 21 Oct. 2016 (the '562 application), now U.S. Pat. No. 10,595,738, which claims the benefit of U.S. provisional application No. 62/244,565, filed 21 Oct. 2015 (the '565 application). The application also claims the benefit of U.S. provisional application No. 62/324,067, filed 18 Apr. 2016 (the '067 application). The '562 application, '565 application and the '067 application are all hereby incorporated by reference as though fully set forth herein. This application is related to U.S. application Ser. No. 15/331,369 (the '369 application) titled "HIGH DENSITY ELECTRODE MAPPING CATHETER" filed 21 Oct. 2016, now U.S. Pat. No. 10,362,954, issued 30 Jul. 2019. The '369 application is incorporated by reference as though fully set forth herein.

a. Field of the Disclosure

This disclosure relates to a high density electrode mapping catheter.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments herein provide an integrated electrode structure. In at least one embodiment, the integrated electrode structure can comprise a catheter shaft comprising a proximal end and a distal end, the catheter shaft defining a catheter shaft longitudinal axis. A flexible tip portion can be located adjacent to the distal end of the catheter shaft, the flexible tip portion comprising a flexible framework. A plurality of microelectrodes can be disposed on the flexible framework and can form a flexible array of microelectrodes adapted to conform to tissue. A plurality of conductive traces can be disposed on the flexible framework, each of the plurality of conductive traces can be electrically coupled with a respective one of the plurality of microelectrodes.

Various embodiments herein provide an integrated electrode structure that comprises a catheter shaft that includes a proximal end and a distal end, the catheter shaft defining a catheter shaft longitudinal axis. A flexible tip portion can be located adjacent to the distal end of the catheter shaft, the flexible tip portion comprising a flexible framework that includes an inner understructure and an outer understructure. A plurality of microelectrodes can be disposed on a top surface of the inner understructure and outer understructure and a bottom surface of the inner understructure and outer understructure, forming a flexible array of microelectrodes adapted to conform to tissue. A plurality of conductive traces can be disposed on the top surface of the inner understructure and outer understructure and a bottom surface of the inner understructure and outer understructure, each of the plurality of conductive traces being electrically coupled with a respective one of the plurality of microelectrodes.

Various embodiments herein provide a method for determining a degree of contact between a first electrode and tissue. In some embodiments, the method can include receiving a first electrical signal from the first electrode disposed on a first side of a tip portion of a medical device. In some embodiments, the method can include receiving a second electrical signal from a second electrode disposed on a second side of the tip portion of the medical device, wherein the first electrode and the second electrode are disposed vertically adjacent with respect to one another. In some embodiments, the method can include determining the degree of contact between the first electrode and the tissue based on a comparison between the first electrical signal and the second electrical signal.

BRIEF DESCRIPTION OF THE DRAWINGS

FIGS. 3A to 3K depict a top view and end view of a second inboard arm of the high density electrode mapping catheter and associated processing steps, according to various embodiments of the present disclosure.

FIG. 6A depicts the conductive flexible framework after an additional layer of dielectric material has been stripped from a distal portion of each of the electrically conductive traces, leaving an exposed area, according to various embodiments of the present disclosure.

FIG. 6B depicts a processed conductive flexible framework after the additional layer of dielectric material has been stripped from a distal portion of each of the electrically conductive traces, leaving an exposed area on which solder has been deposited, according to various embodiments of the present disclosure.

FIG. 6C depicts a cross-sectional end view of the processed conductive flexible framework depicted in FIG. 6B along the line ee, according to various embodiments of the present disclosure.

FIG. 6D depicts a hollow cylindrical band, according to various embodiments of the present disclosure.

FIG. 6E depicts a hollow cylindrical band in which solder is deposited, according to various embodiments of the present disclosure.

FIG. 6F depicts an isometric side and front view of the hollow cylindrical band depicted in FIG. 6D, according to various embodiments of the present disclosure.

FIGS. 7A-7C depict a top view and end view of a second inboard arm of the high density electrode mapping catheter, wherein a flexible framework of the high density electrode mapping catheter is formed from a flexible substrate and associated processing steps, according to various embodiments of the present disclosure.

FIG. 11 depicts mechanical properties of various materials that can be used for forming understructures of the flexible tip portion, according to various embodiments of the present disclosure.

FIGS. 18A to 18G depict top views of embodiments of understructure of a high density electrode mapping catheter in FIG. 1A, according to various embodiments of the present disclosure.

FIG. 19D depicts a schematic side view of microelectrodes disposed on a top and bottom of the flexible tip portion depicted in FIG. 19A, according to various embodiments of the present disclosure.

FIG. 20 depicts an isometric side, top, and distal end view of the flexible tip portion depicted in FIG. 19A, according to various embodiments of the present disclosure.

FIGS. 23A-23F depict an isometric top and side view of an arm of an understructure of a high density electrode mapping catheter, according to various embodiments of the present disclosure.

FIG. 25C depicts an enlarged top view of the mounting portion of the flexible tip portion depicted in FIG. 25A, according to various embodiments of the present disclosure.

FIG. 26 depicts a flexible tip portion of a high density electrode mapping catheter similar to that depicted in FIG. 19A that includes a plurality of wires connected to contact pads disposed on a mounting portion, according to various embodiments of the present disclosure.

DETAILED DESCRIPTION

The contents of International Application No. PCT/US2014/011940 entitled Flexible High-Density Mapping Catheter Tips and Flexible Ablation Catheter Tips with Onboard High-Density Mapping Electrodes is hereby incorporated by reference.

Figure 1A:
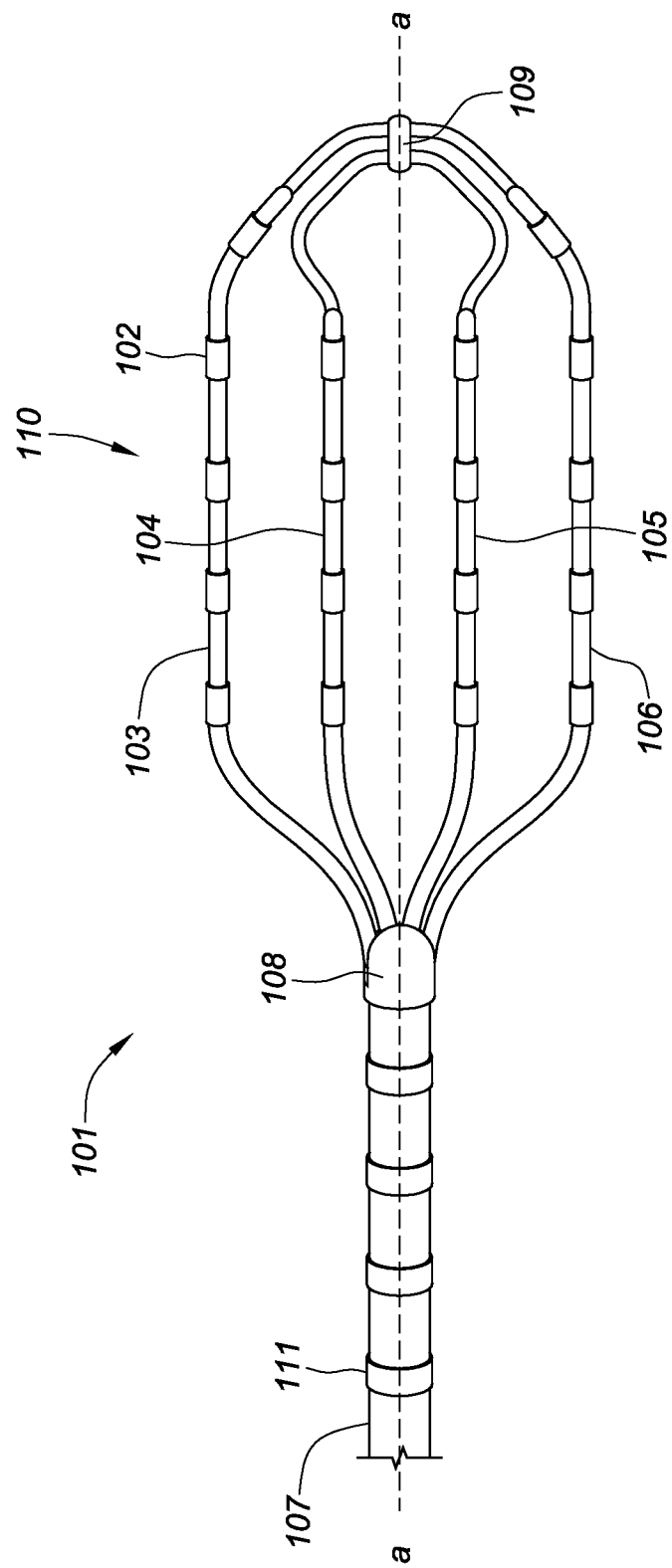
FIG. 1A depicts a top view of a high density electrode mapping catheter, according to various embodiments of the present disclosure.
Figure 1B:
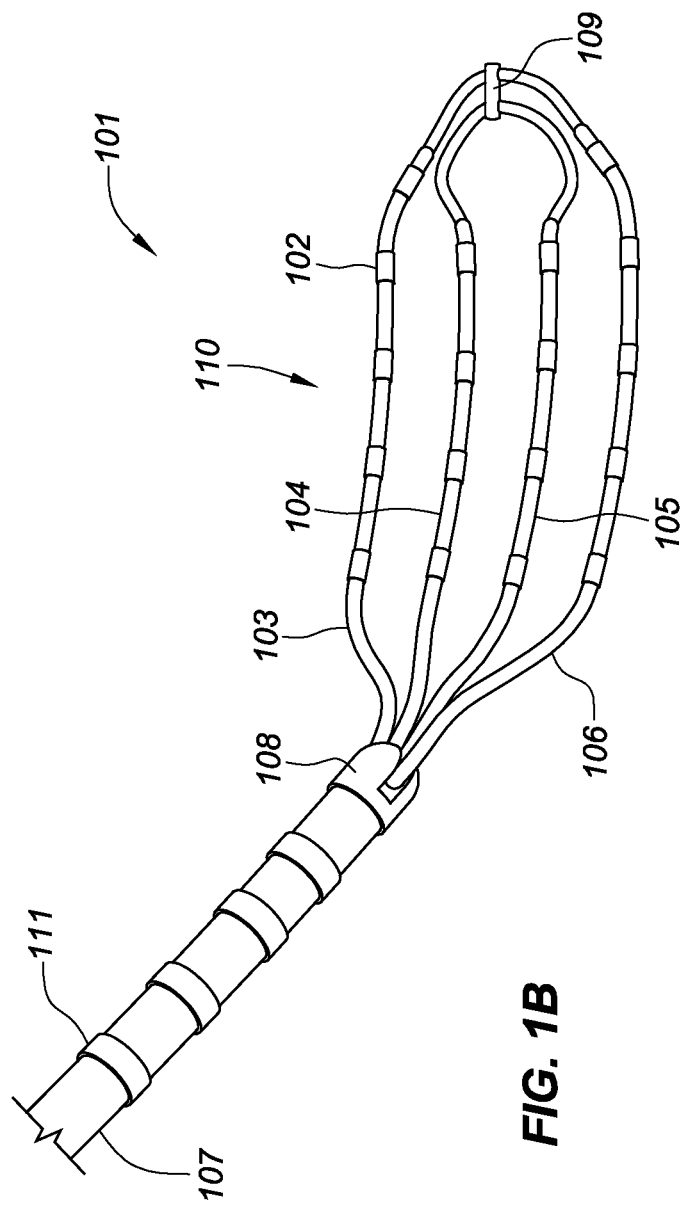
FIG. 1B depicts an isometric side and top view of the high density electrode mapping catheter in FIG. 1A, according to various embodiments of the present disclosure.

FIG. 1A depicts a top view of a high density electrode mapping catheter 101 and FIG. 1B is an isometric side and top view of the high density electrode mapping catheter 101, according to various embodiments of the present disclosure. In some embodiments, the high density electrode mapping catheter 101 can include a flexible tip portion 110 that forms a flexible array of microelectrodes 102. This planar array (or 'paddle' configuration) of microelectrodes 102 comprises four side-by-side, longitudinally-extending arms 103, 104, 105, 106, which can form a flexible framework on which the microelectrodes 102 are disposed. The four microelectrode-carrier arms comprise a first outboard arm 103, a second outboard arm 106, a first inboard arm 104, and a second inboard arm 105. These arms can be laterally separated from each other.

Each of the four arms can carry a plurality of microelectrodes 102. For example, each of the four arms can carry microelectrodes 102 spaced along a length of each of the four arms. Although each of the high density electrode mapping catheters 101 depicted in FIGS. 1A and 1B depict four arms, the high density electrode mapping catheters 101 could comprise more or fewer arms. Additionally, while the high density electrode mapping catheter 101 depicted in FIGS. 1A and 1B depict 18 electrodes (e.g., 5 microelectrodes on first outboard arm 103 and second outboard arm 106 and 4 microelectrodes on first inboard arm 104 and second inboard arm 105), the catheters can include more or fewer than 18 electrodes. In addition, the first outboard arm 103 and second outboard arm 106 can include more or fewer than 5 microelectrodes and the first inboard arm 104 and second inboard arm 105 can include more or fewer than 4 microelectrodes).

In some embodiments, the microelectrodes 102 can be used in diagnostic, therapeutic, and/or mapping procedures. For example and without limitation, the microelectrodes 102 can be used for electrophysiological studies, pacing, cardiac mapping, and ablation. In some embodiments, the microelectrodes 102 can be used to perform unipolar or bipolar ablation. This unipolar or bipolar ablation can create specific lines or patterns of lesions. In some embodiments, the microelectrodes 102 can receive electrical signals from the heart, which can be used for electrophysiological studies. In some embodiments, the microelectrodes 102 can perform a location or position sensing function related to cardiac mapping.

In some embodiments, the high density electrode mapping catheter 101 can include a catheter shaft 107. The catheter shaft 107 can include a proximal end and a distal end. The distal end can include a connector 108, which can couple the distal end of the catheter shaft 107 to a proximal end of the planar array. The catheter shaft 107 can define a catheter shaft longitudinal axis aa, as depicted in FIG. 1A, along which the first outboard arm 103, first inboard arm 104, second inboard arm 105, and second outboard arm 106 can generally extend parallel in relation therewith. The catheter shaft 107 can be made of a flexible material, such that it can be threaded through a tortuous vasculature of a patient. In some embodiments, the catheter shaft 107 can include one or more ring electrodes 111 disposed along a length of the catheter shaft 107. The ring electrodes 111 can be used for diagnostic, therapeutic, and/or mapping procedures, in an example.

As depicted in FIG. 1B, the flexible tip portion 110 can be adapted to conform to tissue (e.g., cardiac tissue). For example, when the flexible tip portion 110 contacts tissue, the flexible tip portion can deflect, allowing the flexible framework to conform to the tissue. In some embodiments, the arms (or the understructure of the arms) comprising the paddle structure (or multi-arm, electrode-carrying, flexible framework) at the distal end of the catheters depicted in FIGS. 1A and 1B are preferably constructed from a flexible or spring-like material such as Nitinol and/or a flexible substrate, as discussed herein. The construction (including, for example, the length and/or diameter of the arms) and material of the arms can be adjusted or tailored to be created, for example, desired resiliency, flexibility, foldability, conformability, and stiffness characteristics, including one or more characteristics that may vary from the proximal end of a single arm to the distal end of that arm, or between or among the plurality of arms comprising a single paddle structure. The foldability of materials such as Nitinol and/or flexible substrate provide the additional advantage of facilitating insertion of the paddle structure into a delivery catheter or introducer, whether during delivery of the catheter into the body or removal of the catheter from the body at the end of a procedure.

Among other things, the disclosed catheters, with their plurality of microelectrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the microelectrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact. Additionally, the catheters described herein may be useful for epicardial and/or endocardial use. For example, the planar array embodiments depicted herein may be used in an epicardial procedure where the planar array of microelectrodes is positioned between the myocardial surface and the pericardium. Alternatively the planar array embodiments may be used in an endocardial procedure to quickly sweep and/or analyze the inner surfaces of the myocardium and quickly create high-density maps of the heart tissue's electrical properties.

Figure 2A:
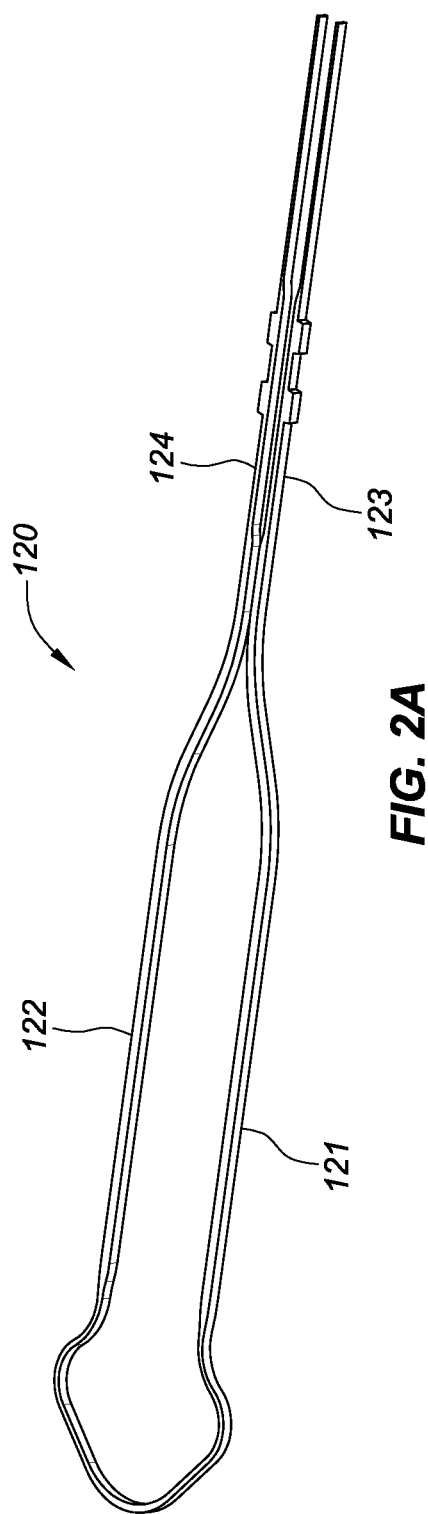
FIG. 2A depicts an isometric side and top view of an inboard understructure of a high density electrode mapping catheter in FIG. 1A, according to various embodiments of the present disclosure.

FIG. 2A is an isometric side and top view of an inboard understructure 120 (also referred to herein as inner understructure) of a high density electrode mapping catheter in FIG. 1A, according to various embodiments of the present disclosure. In some embodiments, the inboard understructure 120 can be formed from a flexible or spring-like material such as Nitinol and/or a flexible substrate, as discussed herein. The inboard understructure 120 can include a first inboard arm understructure 121 and a second inboard arm understructure 122. Although not shown, the outboard understructure (also referred to herein as outer understructure) that provides the understructure for the first outboard arm 103 and the second outboard arm 106 can be formed and/or processed in a manner analogous to that discussed in relation to the inboard understructure 120. Further, if the high density electrode mapping catheter includes additional arms, those arms can be formed and/or processed in a manner analogous to that discussed in relation to the inboard understructure 120. For the sake of brevity, discussion is directed towards the inboard understructure 120. As depicted, the inboard understructure 120 can include a first inboard mounting arm 123 and a second inboard mounting arm 124. The inboard mounting arms can be inserted into a distal end of the catheter 107 and through the connector 108 and can be used to connect the flexible tip portion 110 to the distal end of the catheter 107. In some embodiments, the inboard mounting arms can be inserted through a torsional spacer, as discussed herein.

As depicted in FIG. 2A, the inboard understructure 120 (and although not depicted, the outboard understructure) can be formed from a planar piece of material. However, in some embodiments, the inboard understructure 120 (and the outboard understructure) can be formed from a cylindrical, square, or other shape of understructure. In some embodiments, the inboard understructure 120 and the outboard understructure can be formed from a single unitary piece of material, as discussed in relation to FIGS. 18A to 18G.

Figure 2B:
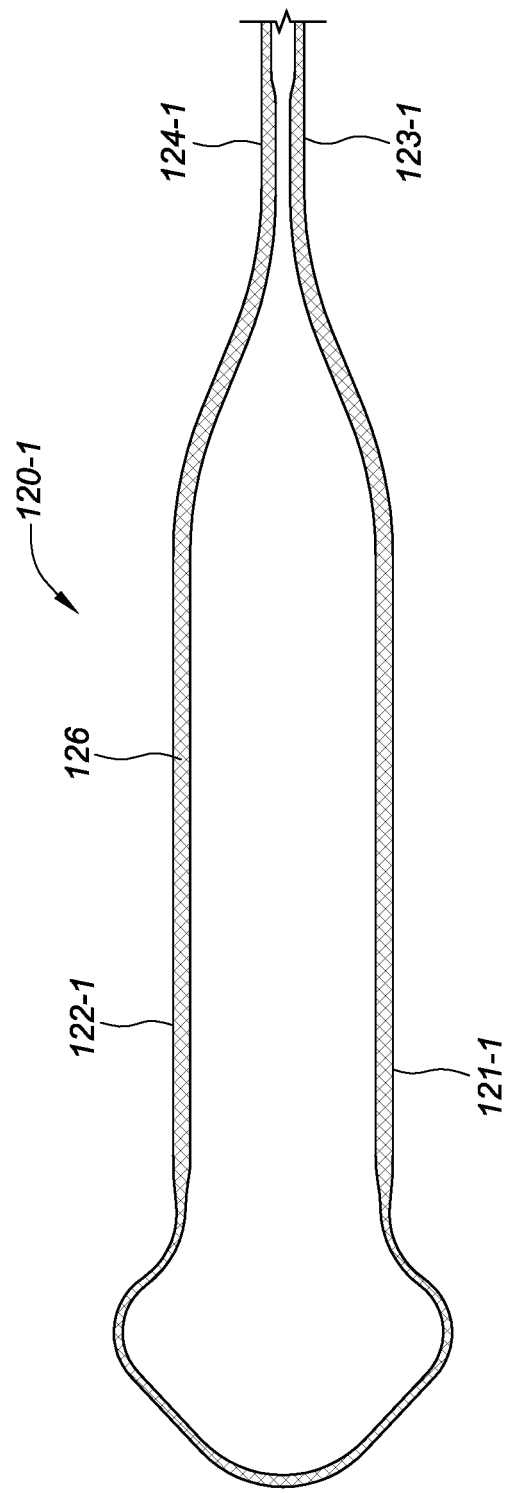
FIG. 2B depicts an isometric side and top view of a coated inboard understructure of a high density electrode mapping catheter, according to various embodiments of the present disclosure.

FIG. 2B depicts an isometric side and top view of a coated inboard understructure 122-1 of a high density electrode mapping catheter 101, according to various embodiments of the present disclosure. In some current practices, high density electrode mapping catheters can be assembled using tubular subassemblies for the inboard understructure and the outboard understructure. One reason for the use of tubing when assembling the understructures is to allow wire to be threaded through the tubing for connection of each individual microelectrode. This process can be labor and/or cost intensive, since each wire may be individually threaded through the tubing and individually connected with each microelectrode. Further, ensuring that a reliable electrical connection is established between each microelectrode and its wire can be challenging.

In addition, use of tubing can result in a less predictable deflection of the flexible tip portion since the walls of the tubing may be symmetrical and are not biased to bend in a particular manner. Embodiments of the present disclosure can provide for a less labor and cost intensive assembly process, as well as provide for a more predictable deflection of the flexible tip portion 110. In some embodiments, a plurality of patterned conductive traces can be disposed on a flexible framework of an expandable structure. For instance, the plurality of patterned conductive traces can be disposed on a flexible framework of an expandable medical device structure. Some embodiments of the present disclosure can provide for a flexible tip portion 110 that includes a plurality of patterned conductive traces disposed on the flexible framework of the flexible tip portion 110, as discussed herein, in lieu of individually run wires. The patterned conductive traces can be electrically coupled with the plurality of microelectrodes 102 disposed on the flexible tip portion 110. The patterned conductive traces can be formed via a process that is less labor and/or cost intensive than current practices. Some embodiments of the present disclosure can provide a means for testing an electrical connection between the microelectrodes 102 and the patterned conductive traces and/or wires, which electrically connect the plurality of microelectrodes 102.

In some embodiments of the present disclosure, the inboard understructure can be coated with a dielectric material. In some embodiments, examples of the dielectric material can include parylene. Other dielectric materials such as a polyimide (e.g., PI-2771 or HD-4004 available from HD Microsystems) and/or an epoxy (e.g., SU8 epoxy available from MicroChem Corp), etc. can be used in accordance with design and end-use requirements. In some embodiments where the understructure is an electrically conductive material, the dielectric can electrically insulate the conductive traces, as discussed herein, from the electrically conductive material.

Figures 3A, 3B, 3C:
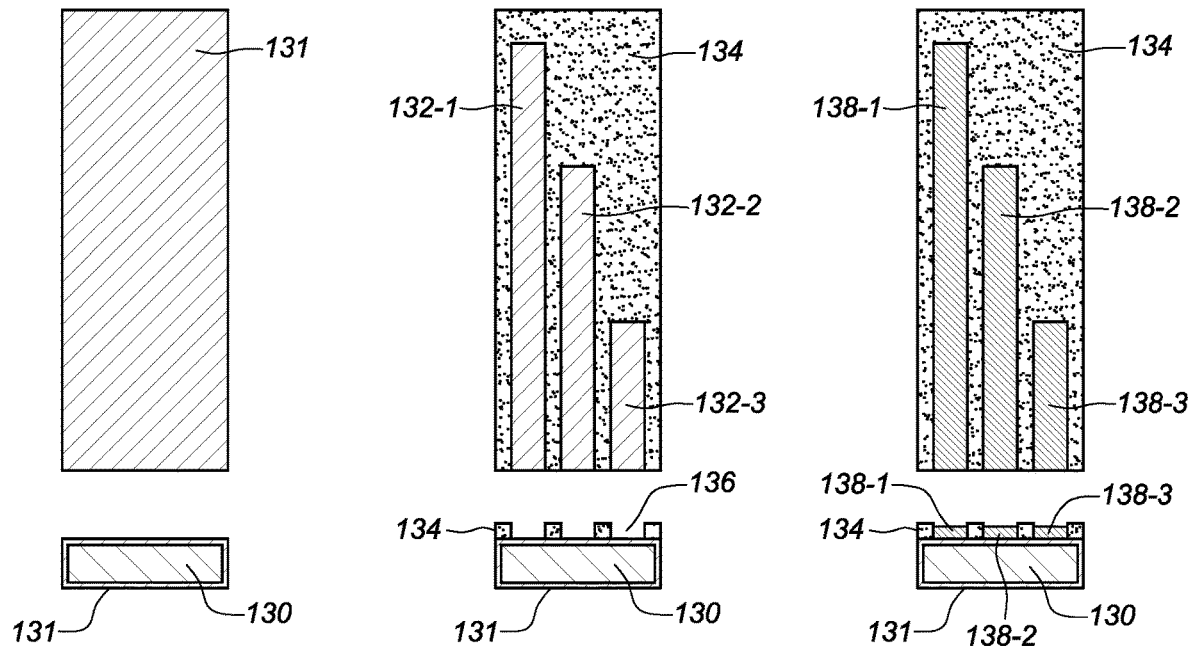

FIGS. 3A to 3K depict a top view and end view of a second inboard arm of the high density electrode mapping catheter and associated processing steps, according to various embodiments of the present disclosure (the top view is depicted above the end view in FIGS. 3A to 3K). FIG. 3A depicts a conductive flexible framework 130 of the inboard understructure 120 coated with a dielectric material 131, according to various embodiments of the present disclosure. In an example, the dielectric material can be applied to the conductive flexible framework 130 to coat the conductive flexible framework 130 in the dielectric material 131 to provide an electrically insulative layer, upon which patterned conductive traces can be disposed.

FIG. 3B depicts the conductive flexible framework 130 of the inboard understructure 120 (also referred to as flexible framework) coated with the dielectric material 131 and a mask 134 (also referred to as masked portion), according to various embodiments of the present disclosure. In an example, one or more unmasked trace pattern portions 132-1, 132-2, 132-3 can be formed on the dielectric coating of the conductive flexible framework 130 via the mask 134. In some embodiments, the mask 134 can form channels 136 along the dielectric material, in which a conductive material can be deposited to form the electrically conductive traces.

FIG. 3C depicts seed layers 138-1, 138-2, 138-3 deposited in the unmasked trace pattern portions 132-1, 132-2, 132-3 of FIG. 3B, according to various embodiments of the present disclosure. In some embodiments, the seed layers can be deposited within the channels 136 to partially fill the channels with the seed layers 138-1, 138-2, 138-3. In some embodiments, the seed layers 138-1, 138-2, 138-3 can include copper (Cu), nickel (Ni), aluminum (Al), etc. The seed layers 138-1, 138-2, 138-3 can provide a base layer upon which a layer of conductive material can be deposited. In an example, the seed layers 138-1, 138-2, 138-3 can provide an interface between the dielectric material 131 and a conductive material which is deposited on the conductive flexible framework 130 to form electrically conductive traces. For instance, the seed layer can allow for the conductive material to be adhered to the dielectric material 131 (e.g., the conductive material is adhered to the dielectric material 131 via the seed layers 138-1, 138-2, 138-3).

Figures 3D, 3E:
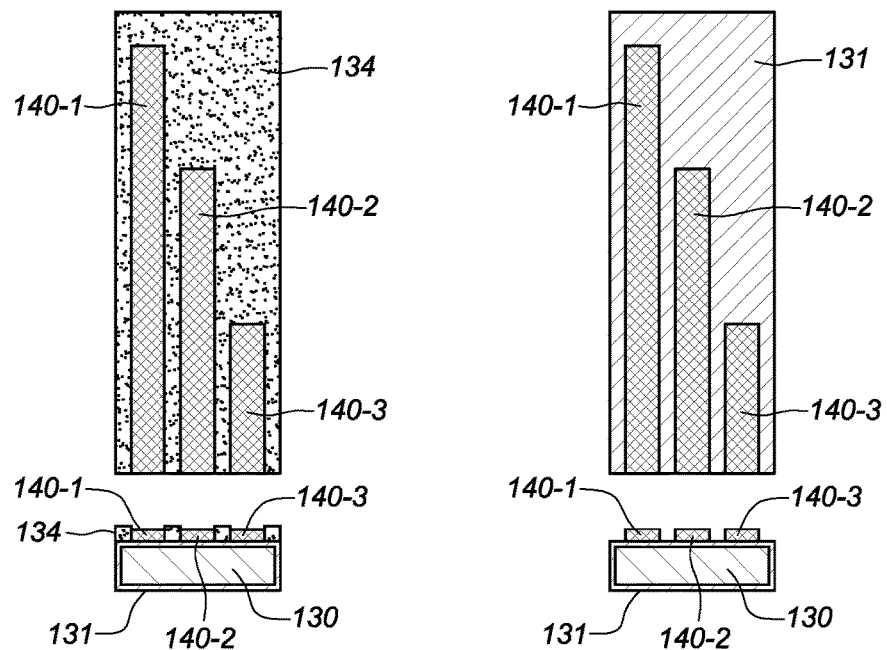

FIG. 3D depicts the seed layers 138-1, 138-2, 138-3 being plated with a conductive material (e.g., copper) to form electrically conductive traces 140-1, 140-2, 140-3, according to various embodiments of the present disclosure. In an example, the conductive material is deposited on the seed layers 138-1, 138-2, 138-3 and is thus adhered to the dielectric material 131. However, because the portions surrounding the electrically conductive traces 140-1, 140-2, 140-3 are masked, the conductive material is not deposited in those locations.

FIG. 3E depicts the conductive flexible framework 130 coated with the dielectric 131 and the electrically conductive traces 140-1, 140-2, 140-3, according to various embodiments of the present disclosure. In some embodiments, the masked portion 134 can be stripped, leaving the electrically conductive traces 140-1, 140-2, 140-3 exposed on the dielectric material 131 that coats the conductive flexible framework 130. In an example, the dielectric material 131 can insulate the electrically conductive traces 140-1, 140-2, 140-3 from the conductive flexible framework 130, thus preventing shorts from occurring between the electrically conductive traces 140-1, 140-2, 140-3.

FIG. 3F depicts the conductive flexible framework 130 coated with an additional layer of dielectric material 141, according to various embodiments of the present disclosure. The additional layer of dielectric material 141 can be deposited over the initial layer of dielectric material 131 and over the electrically conductive traces 140-1, 140-2, 140-3. In some embodiments, the additional layer of dielectric material 141 may only be deposited on the side of the conductive flexible framework 130 upon which the electrically conductive traces 140-1, 140-2, 140-3 are disposed.

FIG. 3G depicts the conductive flexible framework 130 after the additional layer of dielectric material 141 has been stripped from a distal portion of each of the electrically conductive traces 140-1, 140-2, 140-3, leaving an exposed area 142-1, 142-2, 142-3. In some embodiments, laser ablation can be used to strip the distal portion of each of the electrically conductive traces 140-1, 140-2, 140-3 to create the exposed area 142-1, 142-2, 142-3. In some embodiments, the additional layer of dielectric material can be removed via laser ablation. In some embodiments, the exposed area 142-1, 142-2, 142-3 can be formed using photo-definable dielectric materials, wherein the exposed area 142-1, 142-2, 142-3 is masked and the dielectric material is patterned over the masked area. The photo-definable dielectric material can be developed and the masked material can be stripped to generate the exposed area 142-1, 142-2, 142-3.

FIG. 3H depicts mask defined areas 143-1, 143-2, 143-3 on the conductive flexible framework 130, according to various embodiments of the present disclosure. In some embodiments, a mask material (e.g., masked portions 144-1, 144-2, 144-3) can be a photo-definable mask material, wherein the mask material can be patterned over the masked portions 144-1, 144-2, 144-3 and developed to generate the masked portions 144-1, 144-2, 144-3. The masked portions can be located proximally and distally with respect to the distal portion of each of the plurality of conductive traces 140-1, 140-2, 140-3 (and the exposed areas 142-1, 142-2, 142-3) to form the mask defined areas 143-1, 143-2, 143-3.

FIG. 3I depicts seed layers 145-1, 145-2, 145-3 deposited on the mask defined areas 143-1, 143-2, 143-3, according to various embodiments of the present disclosure. As previously discussed, the seed layers 145-1, 145-2, 145-3 can be deposited within the mask defined areas. In some embodiments, the seed layers 145-1, 145-2, 145-3 can include copper (Cu), nickel (Ni), aluminum (Al), etc. The seed layers 145-1, 145-2, 145-3 can provide a base layer upon which a layer of conductive material can be deposited. In an example, the seed layers 145-1, 145-2, 145-3 can provide an interface between the additional layer of dielectric material 141 and the distal portion of the electrically conductive traces 140-1, 140-2, 140-3 and subsequently applied conductive material that forms the microelectrodes 102. For instance, the seed layer can allow for the conductive material that forms the microelectrodes to be adhered to the additional dielectric material 141. And the distal portion of the electrically conductive traces 140-1, 140-2, 140-3.

FIG. 3J depicts microelectrodes 146-1, 146-2, 146-3 that have been formed on the conductive flexible framework 130 via a plating process, according to various embodiments of the present disclosure. In some embodiments, the seed layers 145-1, 145-2, 145-3 can be plated with a conductive material to form the microelectrodes 146-1, 146-2, 146-3. The conductive material that is used to form the microelectrodes 146-1, 146-2, 146-3 can include platinum iridium (Pt-Ir) in some embodiments. The platinum iridium coating process can be performed as described in Rao, Chepuri R.K. and Trivedi, D.C., Chemical and electrochemical depositions of platinum group metals and their applications, Coordination Chemistry Reviews, 249, (2005) pp 613-631; Sheela G., et al., Electrodeposition of Iridium, Bulletin of Electrochemistry, 15 (5-6) May-June 1999, pp 208-210; Wu, Feng, et al., Electrodeposition of Platinum-Iridium Alloy on Nickel-Base Single-Crystal Superalloy TMS75, Surface and Coatings Technology Volume 184, Issue 1, 1 Jun. 2004; Baumgartner, M. E. and Raub, Ch. J., The Electrodeposition of Platinum and Platinum Alloys, Platinum Metals Review, 1988, 32, (4), 188-197; Ohno, Izumi, Electroless Deposition of Palladium and Platinum, Modern Electroplating, 5th Edition, Edited by Mordechay Schlesinger and Milan Paunovic, Copyright 2010, John Wiley & Sons, Inc. Chp 20, 477-482; Electroplating the Platinum Metals—A RECENT SURVEY OF PROCESSES AND APPLICATIONS, Platinum Metals Rev., 1970, 14, (3) pp 93-94; and/or Yingna Wu et al., Characterization of Electroplated Platinum-Iridium Alloys on the Nickel-Base Single Crystal Superalloy, Materials Transactions, Vol. 46, No. 10 (2005) pp 2176-2179, which are hereby incorporated by reference.

In some embodiments, the conductive material can be plated circumferentially around the flexible framework 130. For example, the conductive material can extend circumferentially around one of the first and second inboard arm understructures 121, 122. As such, the seed layers 145-1, 145-2, 145-3, as well as the masked portions 144-1, 144-2, 144-3 can extend circumferentially around the first and second inboard arm understructures 121, 122, such that the conductive material can be plated circumferentially around the flexible framework 130. As such, the microelectrodes 146-1, 146-2, 146-3 can be formed as ring electrodes that are axial with a respective one of the first inboard arm understructure 121 and the second inboard arm understructure 122.

FIG. 3K depicts the dielectric 131 coated conductive flexible framework 130 that includes the additional layer of dielectric material 141, electrically conductive traces 140-1, 140-2, 140-3, and the microelectrodes 146-1, 146-2, 146-3. In some embodiments, the masked portions 144-1, 144-2, 144-3 can be stripped, thus exposing the dielectric coated electrically conductive traces 140-1, 140-2, 140-3 on the dielectric 131 coated conductive flexible framework 130. The microelectrodes 146-1, 146-2, 146-3 can be electrically coupled to each respective electrically conductive trace 140-1, 140-2, 140-3, while remaining insulated from one another as a result of the additional dielectric material 141 that coats the electrically conductive traces 140-1, 140-2, 140-3.

Figure 4A:
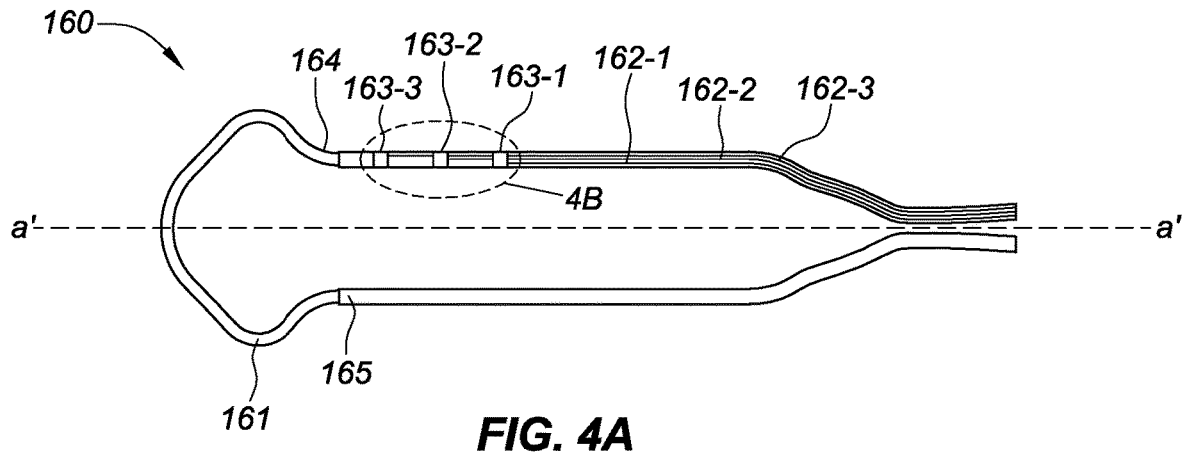
FIG. 4A depicts a top view of a processed inboard understructure, according to various embodiments of the present disclosure.
Figure 4B:
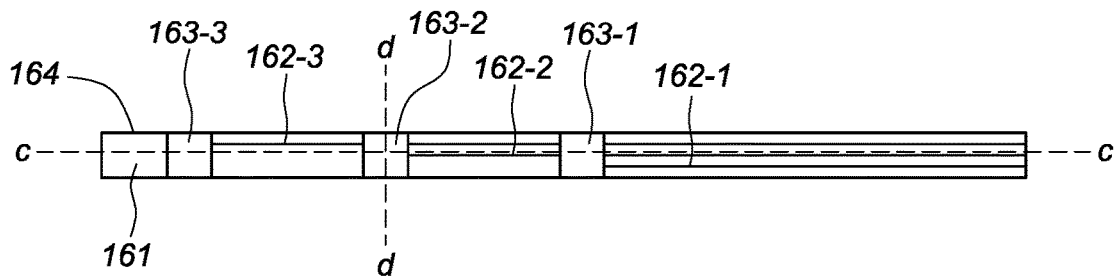
FIG. 4B depicts an enlarged portion (indicated by dotted oval 4B) of a first inboard arm of the processed inboard understructure depicted in FIG. 4A, according to various embodiments of the present disclosure.

FIG. 4A depicts a top view of a processed inboard understructure 160, according to various embodiments of the present disclosure. FIG. 4B depicts an enlarged portion (indicated by dotted oval 4B) of a first inboard arm 164 of the processed inboard understructure depicted in FIG. 4A, according to various embodiments of the present disclosure. As depicted, the processed inboard understructure 160 can be have a dielectric coating 161 that coats a conductive flexible framework (e.g., conductive flexible framework 130) of the processed inboard understructure 160. The dielectric coating 161 can be disposed between each of a plurality of patterned conductive traces 162-1, 162-2, 162-2 and the conductive flexible framework. The dielectric coating 161 can insulate the patterned conductive traces 162-1, 162-2, 162-2 from the conductive flexible framework, thus preventing a short from occurring between the patterned conductive traces 162-1, 162-2, 162-2. In some embodiments, a first patterned conductive trace 162-1 can be electrically coupled to a first microelectrode 163-1; a second patterned conductive trace 162-2 can be electrically coupled to a second microelectrode 163-2; and a third patterned conductive trace 162-3 can be electrically coupled to a third microelectrode 163-3.

In some embodiments, the plurality of microelectrodes 163-1, 163-2, 163-3 can be arranged in a group. For example, the plurality of microelectrodes 163-1, 163-2, 163-3 disposed along the first inboard arm 164 can be arranged in a respective group of three microelectrodes, as depicted in FIG. 4A, although more or fewer than three microelectrodes 163-1, 163-2, 163-3 can be arranged in a group along the first inboard arm 164. In addition, groups of microelectrodes can be arranged along the second inboard arm 165, along the first outboard arm, and/or along the second outboard arm, as depicted in FIG. 1A. In some embodiments, the high density electrode mapping catheter 101 can include more than or fewer than four arms.

The plurality of groups of microelectrodes can be arranged in respective rows of longitudinally aligned microelectrodes that are aligned parallel to a catheter shaft longitudinal axis a'a'. In some embodiments, the plurality of patterned conductive traces 162-1, 162-2, 162-2 can be aligned parallel to the catheter shaft longitudinal axis a'a', depicted in FIG. 1A.

Figure 4C:
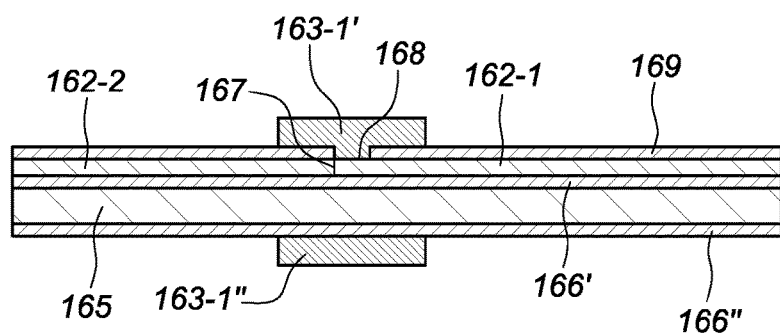
FIG. 4C depicts a cross-sectional view of the first outboard arm along the line cc, in FIG. 4B, according to various embodiments of the present disclosure.
Figure 4D:
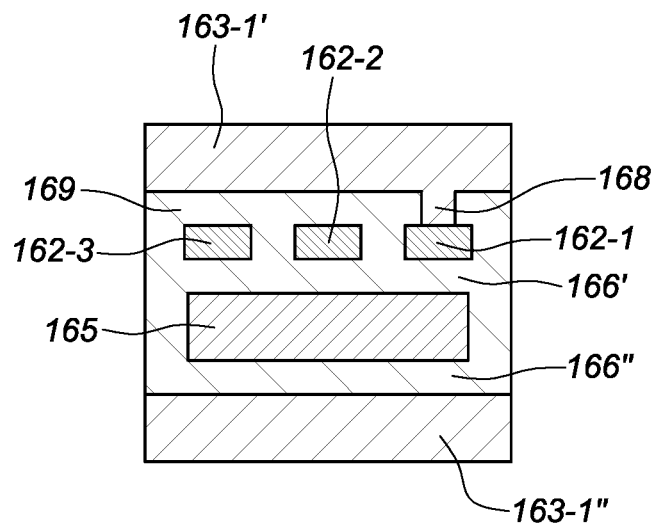
FIG. 4D depicts a cross-sectional view of the first outboard arm along line dd, in FIG. 4B, according to various embodiments of the present disclosure.

FIG. 4C depicts a cross-sectional view of the first outboard arm 164 along the line cc, in FIG. 4B, according to various embodiments of the present disclosure. FIG. 4D depicts a cross-sectional view of the first outboard arm 164 along line dd, in FIG. 4B, according to various embodiments of the present disclosure. As depicted, the first outboard arm 164 includes the conductive flexible framework 165 that has been coated with a dielectric material 166', 166". In some embodiments, the conductive flexible framework 165 can be coated with an upper layer of dielectric material 166' and a lower layer of dielectric material 166". However, the conductive flexible framework 165 can be coated circumferentially with the dielectric material, as discussed herein, such that microelectrodes that are circumferentially and coaxially disposed around the conductive flexible framework 165 are insulated from the conductive flexible framework 165, preventing short circuiting between multiple microelectrodes disposed on the conductive flexible framework 165.

A first patterned conductive trace 162-1 can be disposed on top of the upper layer of dielectric material 166' and can be electrically coupled with the first microelectrode 163-1' via an exposed area located at a distal portion of the first patterned conductive trace 162-1, as discussed herein. In an example, the first microelectrode 163-1' can be coupled to the first patterned conductive trace 162-1 by plating a masked defined area (e.g., mask defined area 145-3), as discussed in relation to FIGS. 3I to 3K. The first microelectrode 163-1' can contact the exposed area 168 (e.g., exposed area 142-3) of the first patterned conductive trace 162-1, thus electrically coupling the first patterned conductive trace 162-1 with the first microelectrode 163-1'. In some embodiments, the first microelectrode 163-1' can be electrically coupled to the exposed area 168 of the first patterned conductive trace 162-1 at a location that is proximal to a distal end 167 of the first patterned conductive trace 162-1.

As depicted in FIG. 4C, the second patterned conductive trace 162-2 (and third patterned conductive trace 162-3, which is obscured by the second patterned conductive trace 162-2) can extend distally with respect to the first microelectrode 163-1' and can be electrically coupled with the second microelectrode 163-2 (and third microelectrode 163-3). The second patterned conductive trace 162-2 (and the third patterned conductive trace 162-3) can be electrically insulated from the first microelectrode 163-1' via an additional layer of dielectric material 169, as discussed herein.

In some embodiments, single layers or multiple layers of patterned conductive traces can be formed on the conductive flexible framework 165. For example, the processed inboard understructure 160 is depicted as including a single layer of patterned conductive traces 162-1, 162-2, 162-3. However, in some embodiments, the processed inboard understructure 160 can multiple layers of patterned conductive traces. This can be desirable where an increased number of microelectrodes are placed on one or more of the inboard arms and/or outboard arms; a width of the frame is decreased, thus decreasing an area for placement of the patterned conductive traces; and/or a width of the patterned conductive traces is increased (e.g., due to a material selection associated with the traces). For example, with an increased number of microelectrodes, a width of the arms may not be sufficient such that the patterned conductive traces are adequately separated from one another to prevent cross-talk and/or shorting between the patterned conductive traces. As such, multiple layers of patterned conductive traces can be formed on the arms, each layer being separated from one another by a dielectric material.

Figure 16:
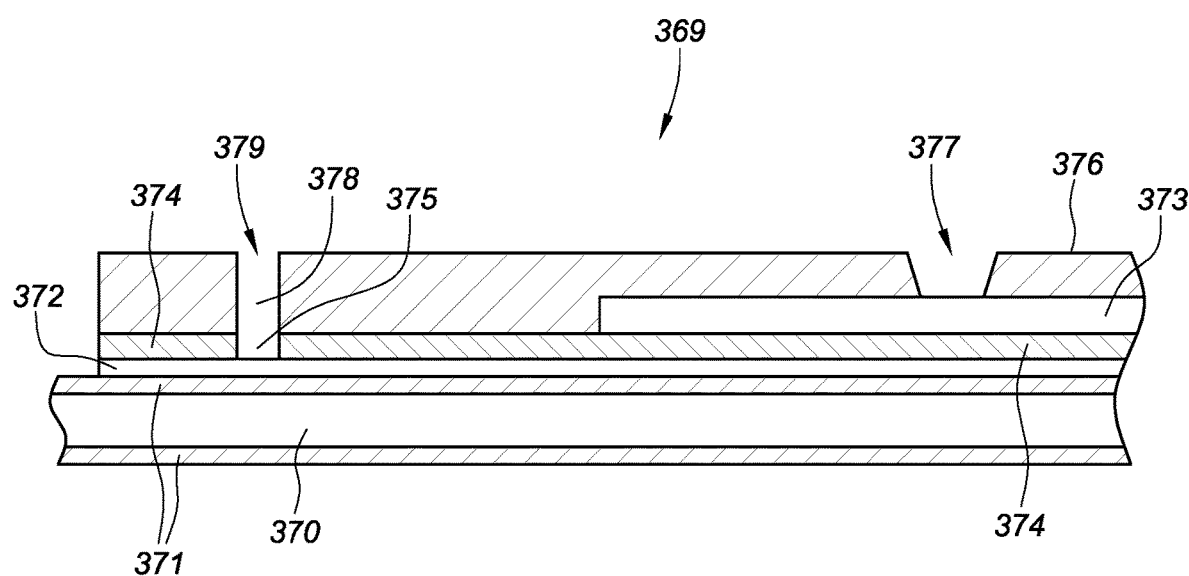
FIG. 16 depicts a side view of an arm of the high density electrode mapping catheter, according to various embodiments of the present disclosure.

Connection between each patterned conductive trace and an associated microelectrode can be made by filled vias, in some embodiments, for example, as discussed in relation to FIG. 16. In some embodiments of the present disclosure, depending on a width of each respective arm, five patterned conductive traces and associated microelectrodes can be formed in a single layer of patterned conductive traces and along a single arm using a 0.001 inch line (e.g., conductive trace) and space (e.g., spacing between the conductive traces) substrate design. For example, each of the patterned conductive traces can be 0.001 inches wide and each patterned conductive trace can be spaced 0.001 inches away from an adjacent patterned conductive trace. In some embodiments, where a greater number of microelectrodes and/or patterned conductive traces are desired, multiple layers of patterned conductive traces can be employed and/or additional traces can be formed on an opposite side of the conductive flexible framework, as depicted in FIG. 5.

Figure 5:
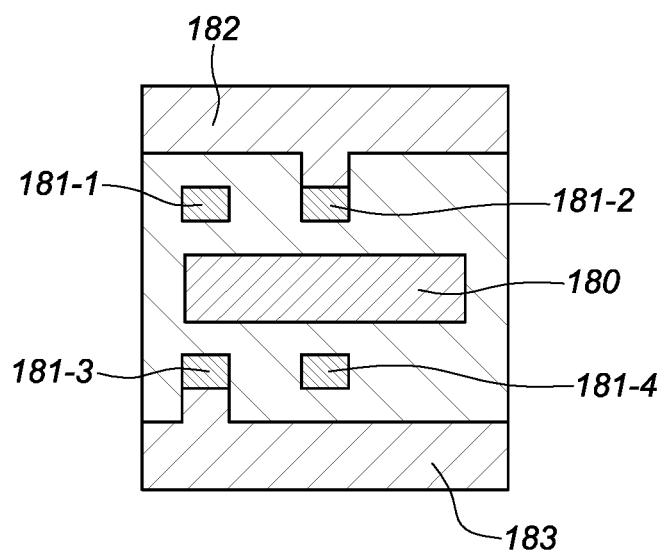
FIG. 5 depicts a cross-sectional view of patterned conductive traces formed on a top and bottom of a conductive flexible framework, according to various embodiments of the present disclosure.

FIG. 5 depicts a cross-sectional view of patterned conductive traces formed on a top and bottom of a conductive flexible framework, according to various embodiments of the present disclosure. In some embodiments, a conductive flexible framework 180 can be coated with a dielectric material, as discussed herein. The dielectric material can be disposed between patterned conductive traces 181-1, 181-2, 181-3, 181-4 and the conductive flexible framework 180, which can serve to insulate the patterned conductive traces 181-1, 181-2, 181-3, 181-4 from the conductive flexible framework 180. In some embodiments, one or more patterned conductive traces can be formed on a top of the conductive flexible framework 180 (e.g., patterned conductive traces 181-1, 181-2) and one or more patterned conductive traces can be formed on a bottom of the conductive flexible framework 180 (e.g., patterned conductive traces 181-3, 181-4) in a manner analogous to that discussed in relation to FIGS. 3A to 3K.

FIG. 6A depicts the conductive flexible framework 130' after the additional layer of dielectric material 141' has been stripped from a distal portion of each of the electrically conductive traces 140-1', 140-2', 140-3', leaving an exposed area 142-1', 142-2', 142-3', according to various embodiments of the present disclosure. In an example, process steps associated with FIGS. 3A to 3G can be performed to arrive at the embodiment depicted in FIG. 6A. In some embodiments, rather than plating the exposed areas 142-1', 142-2', 142-3', solder can be deposited on the distal portions of each of the electrically conductive trace (e.g., traces 140-1', 140-2', 140-3'). For example, FIG. 6B depicts a processed conductive flexible framework 199 after the additional layer of dielectric material 141' has been stripped from a distal portion of each of the electrically conductive traces 140-1', 140-2', 140-3', leaving an exposed area 142-1', 142-2', 142-3' on which solder 191-1, 191-2, 191-3 has been deposited, according to various embodiments of the present disclosure. FIG. 6C depicts a cross-sectional end view of the processed conductive flexible framework 199 depicted in FIG. 6B along the line ee.

FIG. 6D depicts a hollow cylindrical band 200, according to various embodiments of the present disclosure. FIG. 6E depicts a hollow cylindrical band 203 in which solder 208 is deposited, according to various embodiments of the present disclosure. FIG. 6F depicts an isometric side and front view of the hollow cylindrical band 200 depicted in FIG. 6D, according to various embodiments of the present disclosure. In some embodiments, the hollow cylindrical band 200 can be the same or similar to the hollow cylindrical band 203 depicted in FIG. 6E. In some embodiments, the hollow cylindrical band 200 can include a split 201, which can extend longitudinally down a sidewall of the hollow cylindrical band. Although, as depicted in FIG. 6D (and FIG. 6F), the split 201 extends parallel with a longitudinal axis of the hollow cylindrical band 200, the split 201 can be divergent with the longitudinal axis of the hollow cylindrical band 200.

Figure 6G:
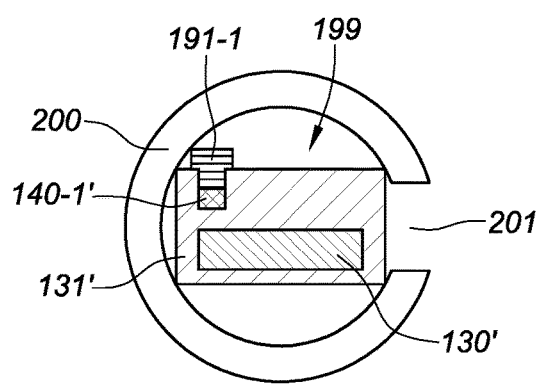
FIG. 6G depicts a hollow cylindrical band coaxially aligned with the processed conductive flexible framework, according to various embodiments of the present disclosure.

In some embodiments, as depicted in FIG. 6G the hollow cylindrical band 200 can be coaxially aligned with the processed conductive flexible framework 199. In some embodiments, the hollow cylindrical band 200 can be slipped over a proximal end of an arm of the processed conductive flexible framework 199 into position over the solder 191-1. For example, the hollow cylindrical band 200 can be placed over the solder 191-1 such the solder 191-1 is aligned with the hollow cylindrical band 200 between a proximal end and a distal end of the hollow cylindrical band 200. In some embodiments, a circumferential width of the split 201 in the hollow cylindrical band 200 (defined by line gg in FIG. 6D) can be greater than a height of the processed conductive flexible framework (defined by line ff in FIG. 6C), such that the hollow cylindrical band 200 (e.g., the slit 201 of the hollow cylindrical band 200) can be laterally slid over the processed conductive flexible framework 199, instead of being slipped over a proximal end of the arm of the processed conductive flexible framework 199.

Figure 6H:
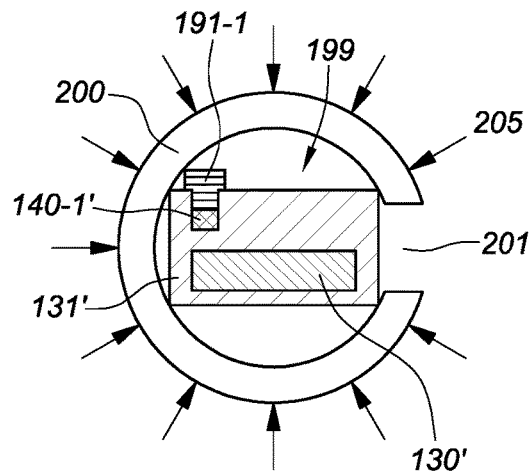
FIG. 6H depicts a processing step associated with the hollow cylindrical band, according to various embodiments of the present disclosure.
Figure 6I:
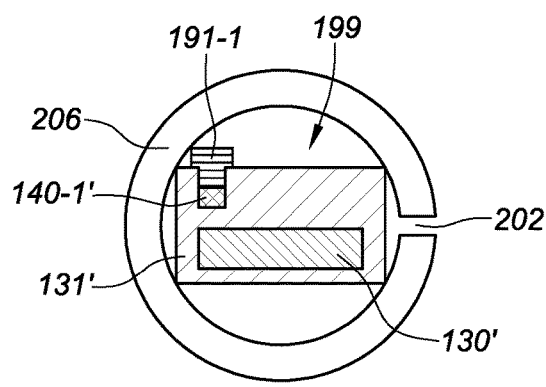
FIG. 6I depicts a swaged hollow cylindrical band after performing the processing step described in relation to FIG. 6H, according to various embodiments of the present disclosure.

FIG. 6H depicts a processing step associated with the hollow cylindrical band 200, according to various embodiments of the present disclosure. In some embodiments, as discussed herein, the hollow cylindrical band 200 can be coaxially aligned with the processed conductive flexible framework 199 and the solder 191-1 can be aligned with the hollow cylindrical band 200 between a proximal end and a distal end of the hollow cylindrical band 200. The hollow cylindrical band 200 can be swaged onto the processed conductive flexible framework 199. In an example, a force can be applied to the hollow cylindrical band 200 in a direction of at least one of the arrows (e.g., arrow 205) to swage the hollow cylindrical band 200 onto the processed conductive flexible framework 199. FIG. 6I depicts the swaged hollow cylindrical band 206 after the processing step described in relation to FIG. 6H, according to various embodiments of the present disclosure. As depicted, a circumferential width of the split 202 can be decreased as a result of the swaging process and the swaged hollow cylindrical band 206 can contact portions of the processed conductive flexible framework 199 (e.g., the corners of the processed conductive flexible framework 199 and the solder 191-1).

Figure 6J:
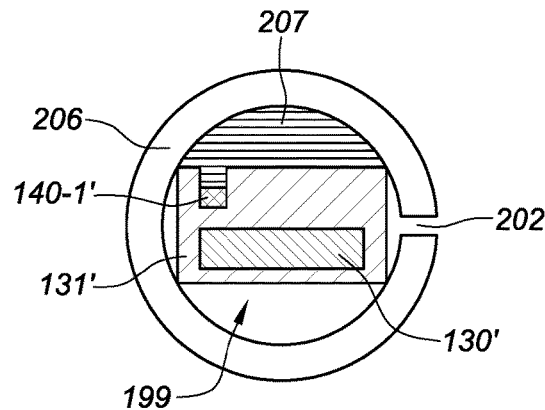
FIG. 6J depicts the swaged hollow cylindrical band and the processed conductive flexible framework after a solder reflow process, according to various embodiments of the present disclosure.

FIG. 6J depicts the swaged hollow cylindrical band 206 and the processed conductive flexible framework 199 after a solder reflow process, according to various embodiments of the present disclosure. In an example, a reflow process can be performed to reflow the solder depicted in FIG. 6I, such that the reflowed solder 207 is distributed and contacts both the swaged hollow cylindrical band 206 and the processed conductive flexible framework 199. The solder 207 can connect the swaged hollow cylindrical band 206 and the processed conductive flexible framework 199 and can electrically couple the electrically conductive trace 140-1 and the swaged hollow cylindrical band 206. As such, the swaged hollow cylindrical band 206 forms the microelectrode, as discussed herein.

With reference to FIG. 6E, where solder 208 is deposited on the hollow cylindrical band 203, solder (e.g., solder 191-1) may or may not be placed on the exposed area 142-1', 142-2', 142-3' of the electrically conductive traces 140-1', 140-2', 140-3'. In an example, the hollow cylindrical band 203 can be placed over the processed conductive flexible framework 199 such that the solder 208 is in close proximity to the exposed area 142-1', 142-2', 142-3' of the electrically conductive traces 140-1', 140-2', 140-3'. In some embodiments, the processing steps depicted and described in relation to FIGS. 6G-6J can be performed to swage the hollow cylindrical band 203 and reflow the solder 208 to establish a connection between the hollow cylindrical band 203 and the processed conductive flexible framework 199 and an electrical connection between the hollow cylindrical band 203 and the electrically conductive trace 140-1'. In some embodiments, solder can be deposited on the hollow cylindrical band 203 and the exposed area 142-1', 142-2', 142-3' of the electrically conductive traces 140-1', 140-2', 140-3' to allow for an increased distribution of solder in the reflowing process.

FIG. 7A depicts a top view and end view of a second inboard arm of the high density electrode mapping catheter, wherein a flexible framework 220 of the high density electrode mapping catheter is formed from a flexible substrate and associated processing steps, according to various embodiments of the present disclosure (the top view is depicted above the end view in FIGS. 7A to 7C). In some embodiments, the flexible framework 220 can be formed from a flexible substrate, in some embodiments. The flexible substrate can include for example, those discussed in relation to FIG. 11. In some embodiments, the flexible substrate can include a printed circuit board. For example, the printed circuit board can be formed from a fiberglass and/or a plastic, which does not conduct electricity. In some embodiments, the printed circuit board can be formed from a polymer. As depicted in FIG. 7A, in some embodiments, the flexible substrate 220 can be coated with a conductive material 222. The conductive material 222 can include Cu, for example, although other conductive materials can be used.

FIG. 7B depicts a top view and end view of the second inboard arm of the high density electrode mapping catheter, wherein a mask layer is deposited on the conductive material 222 coating the flexible framework 220 to form a masked trace pattern 223-1, 223-2, 223-3 on the coated flexible framework and an unmasked portion, according to various embodiments of the present disclosure. In an example, the surrounding areas of the masked trace pattern 223-1, 223-2, 223-3 include the uncoated conductive material 222.

FIG. 7C depicts a top view and end view of the second inboard arm of the high density electrode mapping catheter, wherein the surrounding areas of the masked trace pattern 223-1, 223-2, 223-3 have been stripped of the conductive material 222. In an example, the conductive material 222 can be stripped such that the flexible substrate 220 that surrounds the masked trace pattern 223-1 is exposed. As depicted in FIG. 7C, the masked trace pattern 223-1, 223-2, 223-3 has also been stripped thus exposing electrically conductive traces 224-1, 224-2, 224-3. The electrically conductive traces 224-1, 224-2, 224-3 can be directly connected with the flexible substrate 220, which is electrically insulative. Accordingly, the electrically conductive traces 224-1, 224-2, 224-3 can be electrically insulated from one another, thus preventing short circuits from occurring between the electrically conductive traces 224-1, 224-2, 224-3.

In some embodiments, as will be apparent to those of skill in the art, the embodiment depicted in FIG. 7C can be processed further using the processing steps depicted and described in relation to FIGS. 3E to 3K and/or FIGS. 6A to 6J. For example, a dielectric coating can be deposited on the electrically conductive traces 224-1, 224-2, 224-3 as well as the flexible substrate 220 and exposed areas of the electrically conductive traces 224-1, 224-2, 224-3 can be formed.

Figure 8A:
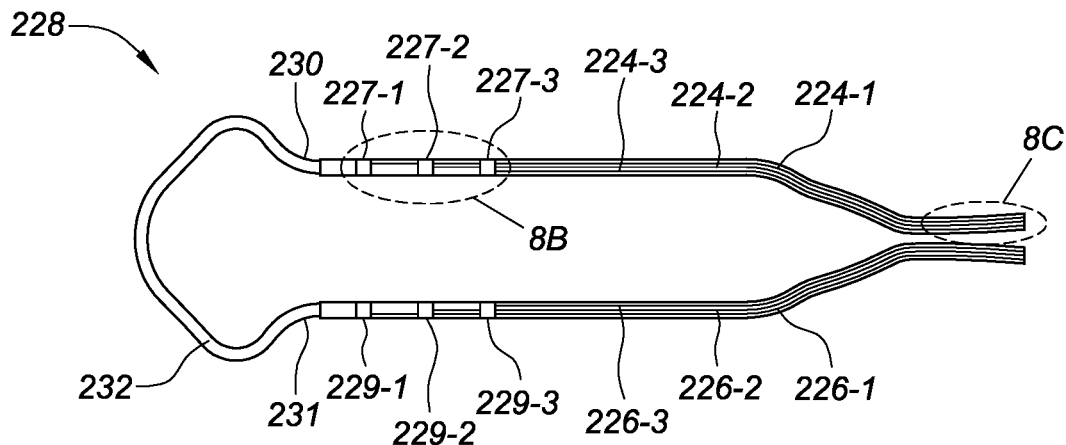
FIG. 8A depicts a top view of a processed inboard understructure, according to various embodiments of the present disclosure.
Figure 8B:
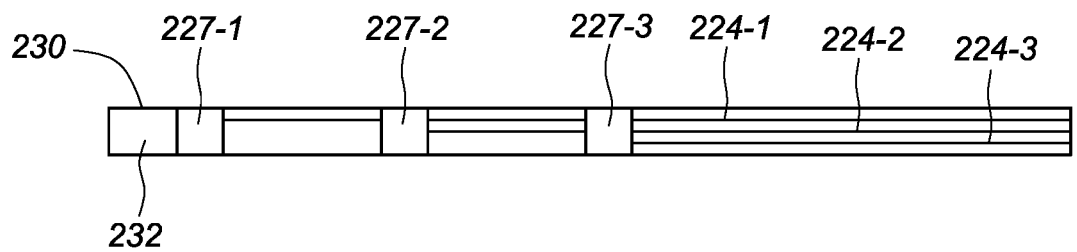
FIG. 8B depicts an enlarged portion (indicated by dotted oval 8B) of a first inboard arm of the processed inboard understructure depicted in FIG. 8A, according to various embodiments of the present disclosure.

FIG. 8A depicts a top view of a processed inboard understructure 228, according to various embodiments of the present disclosure. FIG. 8B depicts an enlarged portion (indicated by dotted oval 8B) of a first inboard arm 230 of the processed inboard understructure 228 depicted in FIG. 8A, according to various embodiments of the present disclosure. The processed inboard understructure 228 includes a first inboard arm 230 and a second inboard arm 231. The processed inboard understructure 228 can be formed from a flexible substrate, in some embodiments, as discussed herein. For example, the flexible substrate include a printed circuit board and/or polymer, in some embodiments. The flexible substrate can be coated with a dielectric material 232, in some embodiments.

The first inboard arm 230 of the processed inboard understructure 228 includes electrically conductive traces 224-1, 224-2, 224-3 and microelectrodes 227-1, 227-2, 227-3. A first electrically conductive trace 224-1 can be electrically coupled to a first microelectrode 227-1; a second electrically conductive trace 224-2 can be electrically coupled to a second microelectrode 227-2; and a third electrically conductive trace 224-3 can be electrically coupled to a third microelectrode 227-3. The second inboard arm 231 of the processed inboard understructure 228 includes electrically conductive traces 226-1, 226-2, 226-3 and microelectrodes 229-1, 229-2, 229-3. A first electrically conductive trace 226-1 can be electrically coupled to a first microelectrode 229-1; a second electrically conductive trace 226-2 can be electrically coupled to a second microelectrode 229-2; and a third electrically conductive trace 226-3 can be electrically coupled to a third microelectrode 229-3.

Figure 8C:
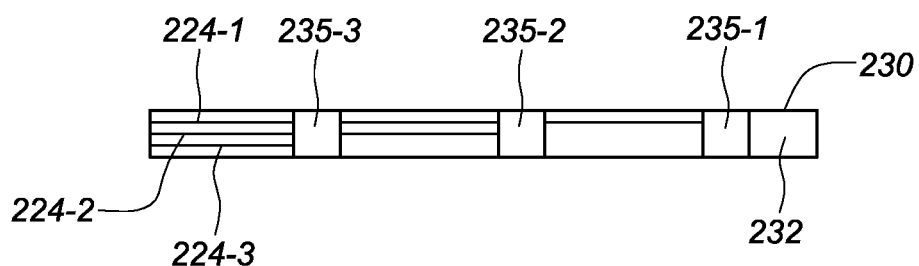
FIG. 8C depicts an enlarged portion (indicated by dotted oval 8C) of a first inboard arm of the processed inboard understructure depicted in FIG. 8A, according to various embodiments of the present disclosure.

FIG. 8C depicts an enlarged portion (indicated by dotted oval 8C) of the first inboard arm 230 of the processed inboard understructure 228 depicted in FIG. 8A, according to various embodiments of the present disclosure. In an example, FIG. 8C depicts the first electrically conductive trace 224-1 electrically coupled to a first proximal termination contact pad 235-1; the second electrically conductive trace 224-2 electrically coupled to a second proximal termination contact pad 235-2; and the third electrically conductive trace 224-3 electrically coupled to a third proximal termination contact pad 235-3. The proximal termination contact pads are not depicted in FIG. 8A. In some embodiments, the flexible framework of the flexible tip portion 110 of the high density electrode mapping catheter 101 can include the proximal termination contact pads. For example, each arm of the inboard understructure and/or each arm of the outboard understructure (and/or additional understructures not shown) can include the proximal termination contact pads along a proximal portion of the inboard understructure and/or outboard understructure.

In some embodiments, the proximal termination contact pads 235-1, 235-2, 235-3 can provide electrical connection points for electrically connecting the microelectrodes (e.g., microelectrodes 227-1, 227-2, 227-3). For example, the proximal termination contact pads 235-1, 235-2, 235-3 can provide an increased area for an electrical connection to be made with each of the electrically conductive traces 224-1, 224-2, 224-3 and thus each of the microelectrodes 227-1, 227-2, 227-3. In some embodiments, the proximal termination contact pads 235-1, 235-2, 235-3 can be used to electrically test continuity between each of the electrically conductive traces and respective microelectrodes. For example, each of the proximal termination contact pads can be probed with an electrical testing device to ensure that an uninterrupted electrical connection exists between each of the proximal termination contact pads, a respective one of the electrically conductive traces, and a respective microelectrode. In some embodiments, the proximal termination contact pads can provide an increased area for probing with the electrical testing device (e.g., versus proving each individual electrically conductive trace).

Figure 9A:
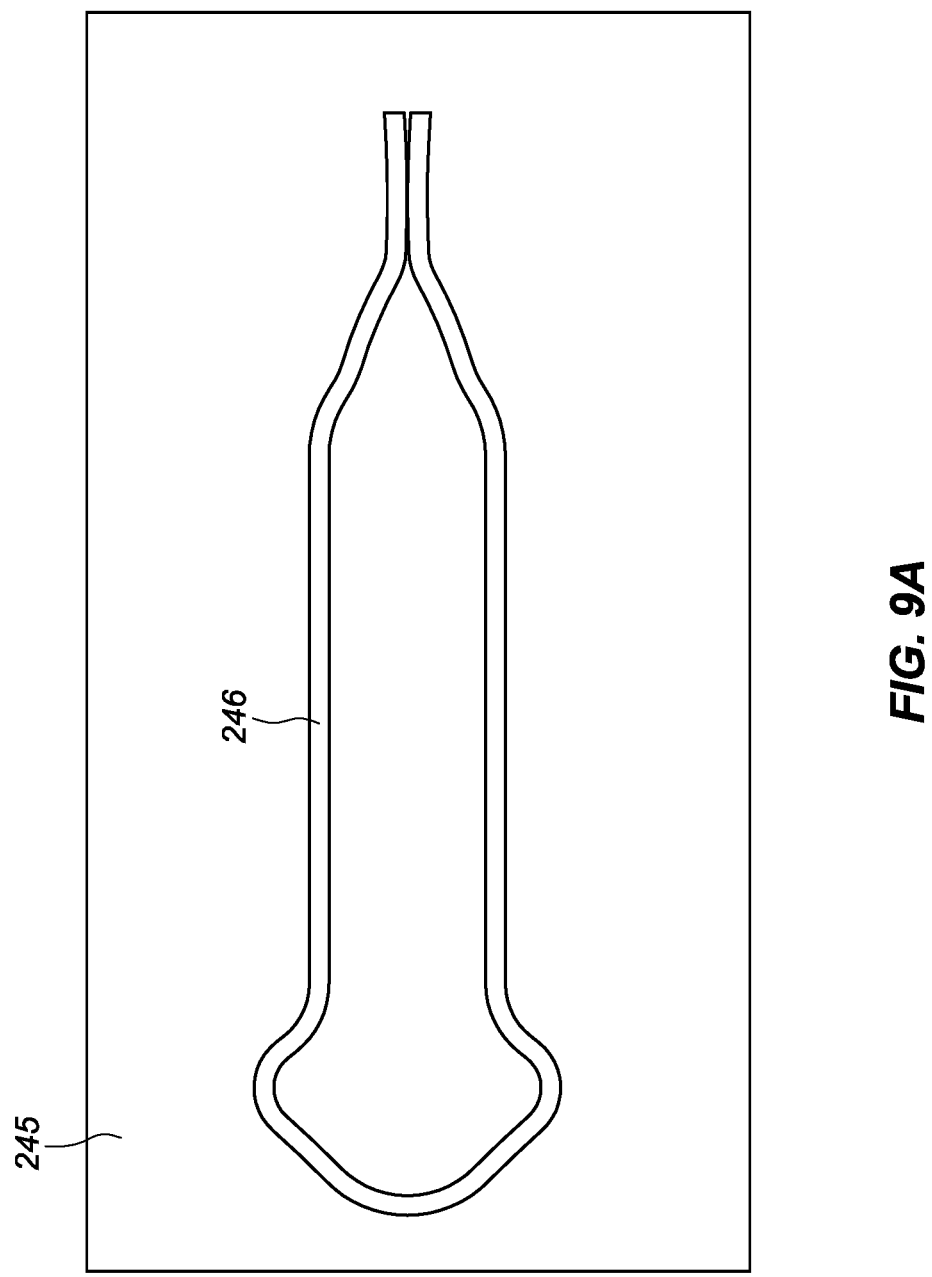
FIG. 9A depicts a top view of a bottom mold for an overmolding process, according to various embodiments of the present disclosure.

FIG. 9A depicts a top view of a bottom mold 245 for an overmolding process, according to various embodiments of the present disclosure. The bottom mold 245 includes a mold cavity 246, which can be size and configured to accept an understructure (e.g., processed understructure) of the flexible tip portion 110. In some embodiments, different molds can be used for the outboard understructure and the inboard understructure (and additional understructures if included). In some embodiments, the bottom mold 245 can be sized and configured to accept the processed inboard understructure 160 and/or the processed inboard understructure 228 in the mold cavity 246, as depicted in FIG. 9B.

Figure 9B:
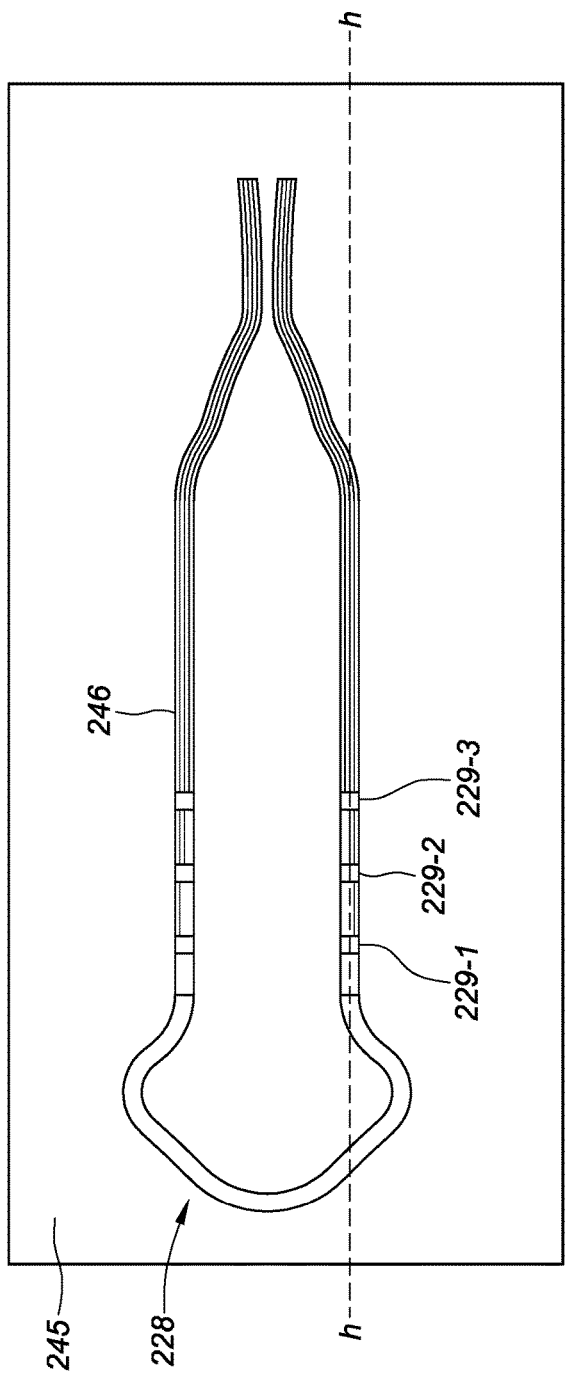
FIG. 9B depicts a processed inboard understructure inserted into the bottom mold depicted in FIG. 9A, according to various embodiments of the present disclosure.
Figure 9C:
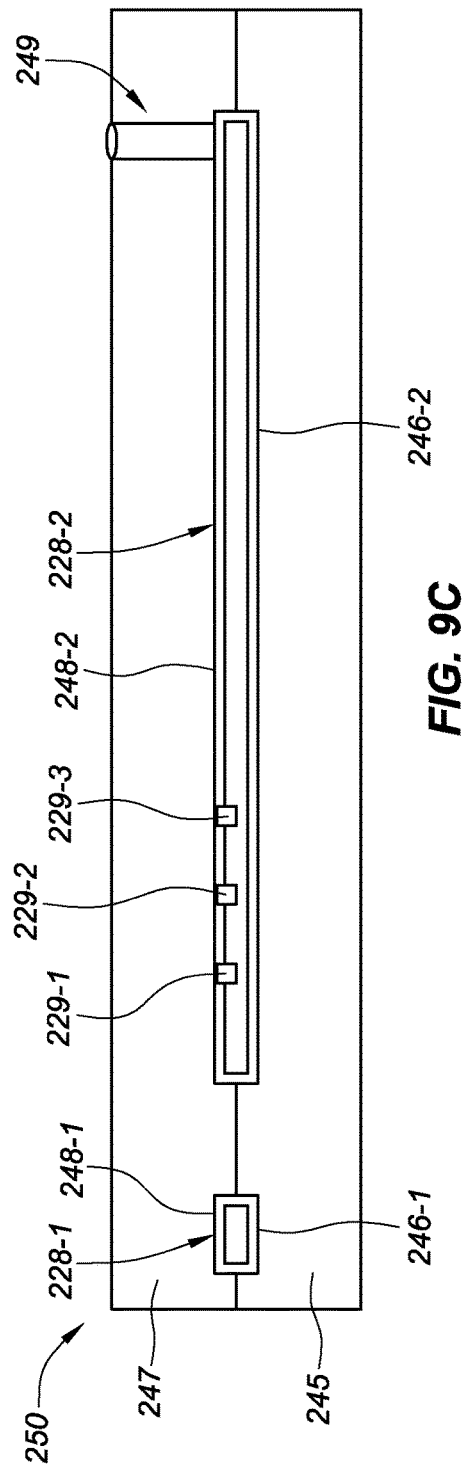
FIG. 9C depicts a cross-sectional side view of an assembled mold and the processed inboard understructure in FIG. 9B along line hh in FIG. 9B, according to various embodiments of the present disclosure.

FIG. 9B depicts a top view of a processed inboard understructure 228 inserted into the bottom mold 245, according to various embodiments of the present disclosure. In an example, the processed inboard understructure 228 depicted in FIG. 8A is depicted as being inserted in the mold cavity 246 of the bottom mold 245. FIG. 9C depicts a cross-sectional side view of an assembled mold 250 along line hh in FIG. 9B, according to various embodiments of the present disclosure.

FIG. 9C depicts a top mold 247 and the bottom mold 245 in a closed position, thus enclosing the processed inboard understructure 228 (consisting of distal portion 228-1 of the processed inboard understructure 228 and proximal portion 228-2 of the processed inboard understructure 228) in the mold cavity and forming assembled mold 250. In an example, the assembled mold 250 includes a bottom mold cavity 246. The cross-sectional view of the bottom mold cavity 246 depicts a distal bottom mold cavity 246-1 and a proximal bottom mold cavity 246-2. The bottom mold cavity 246 can be formed in the bottom mold 245. In an example, the assembled mold 250 includes a top mold cavity 248. The cross-sectional view of the top mold cavity 248 depicts a distal top mold cavity 248-1 and a proximal top mold cavity 248-2. The top mold cavity 248 can be formed in the top mold 247 of the assembled mold 250.

In some embodiments, the bottom mold 245 and the top mold 247 can include standoffs (not shown) that extend into the bottom mold cavity 246 and the top mold cavity 248 to position the processed inboard understructure 228 a particular distance away from walls of the bottom mold 245 and the top mold 247 that form the bottom mold cavity 246 and the top mold cavity 248. In an example, the distance between the processed inboard understructure 228 and the walls of the bottom mold 245 and the top mold 247 can define a thickness of an overmolding that covers the understructure.

In some embodiments, the top mold 247 and/or the bottom mold 245 can include a port 249 configured for introduction of an overmolding material into the bottom mold cavity 246 and the top mold cavity 248. In some embodiments, the assembled mold 250 can include a gate and runner system to help with distribution of the overmolding material into the bottom mold cavity 246 and the top mold cavity 248. The gate and runner system can be designed in accordance with rheological properties of an overmolding material.

Figure 9D:
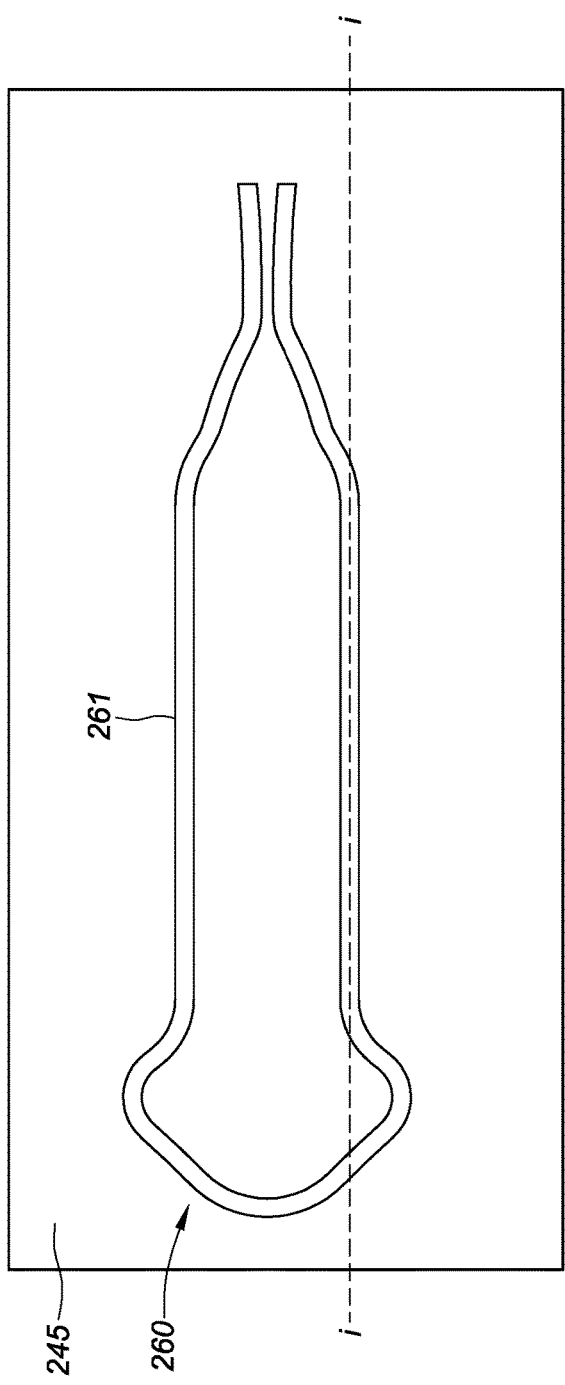
FIG. 9D depicts a top view of bottom mold and an overmolded inboard understructure after an overmolding process has been performed, according to various embodiments of the present disclosure.
Figure 9E:
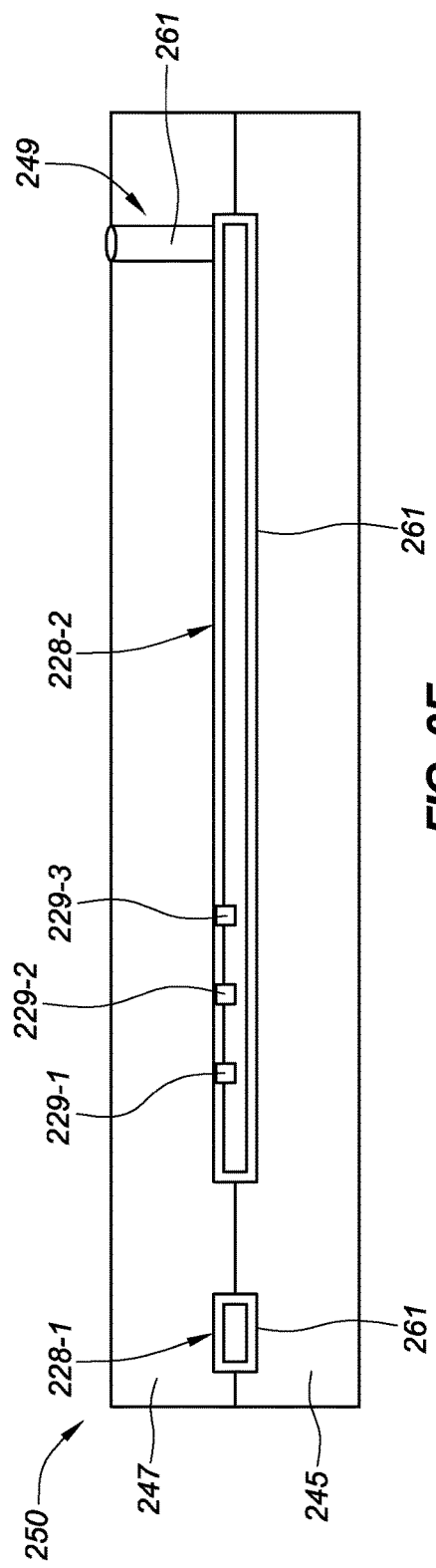
FIG. 9E depicts a cross-sectional side view of an assembled mold and the overmolded inboard understructure in FIG. 9D along line ii in FIG. 9D, according to various embodiments of the present disclosure.

FIG. 9D depicts a top view of bottom mold 245 and an overmolded inboard understructure 260 after an overmolding process has been performed, according to various embodiments of the present disclosure. FIG. 9E depicts a cross-sectional side view of an assembled mold and the overmolded inboard understructure in FIG. 9D along line ii in FIG. 9D, according to various embodiments of the present disclosure. As depicted, the processed inboard understructure 228 has been overmolded with an overmolding material 261. The overmolding material 261 is injected via the port 249 and fills the space existing between the processed inboard understructure 228 and the walls of the bottom mold 245 and the top mold 247 (e.g., assembled mold 250). In some embodiments, the overmolding material 261 can include a polyether block amide (e.g., PEBAX® available from Arkema). In some embodiments, the overmolding material can be a polyurethane (e.g., Pellethane 2363-80A or 2363-90A, or Tecoflex EG93A or EG100A both available from Lubrizol Corp.) or other suitable materials having the required biocompatibility, elastomeric, and mechanical properties required by specific design and end-use requirements.

Figure 10A:
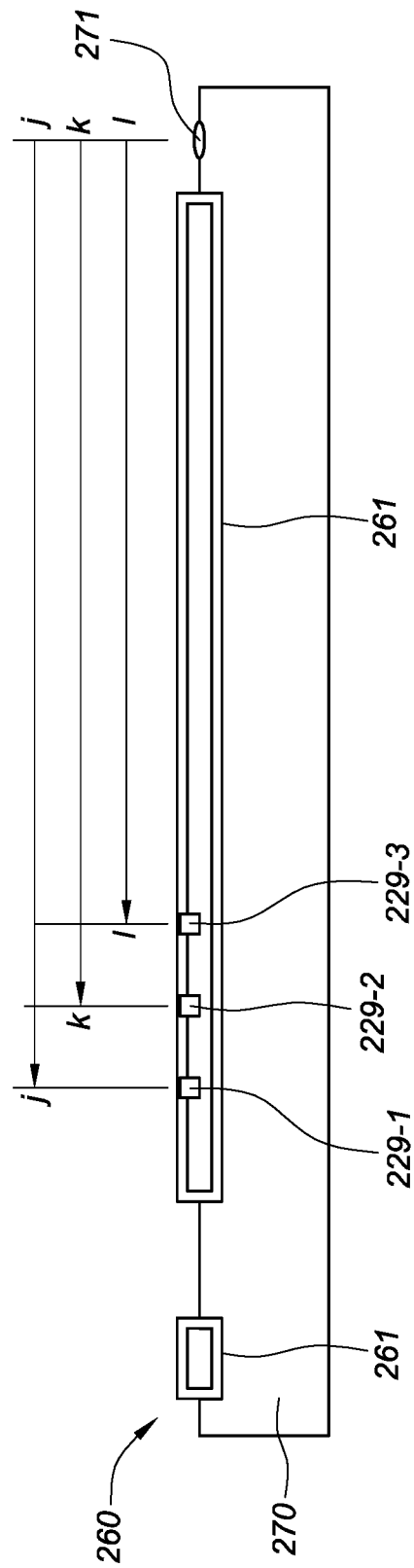
FIG. 10A depicts a cross-sectional side view of an ablation fixture in which the overmolded inboard understructure has been placed, according to various embodiments of the present disclosure.

FIG. 10A depicts a cross-sectional side view of an ablation fixture 270 in which the overmolded inboard understructure 260 has been placed, according to various embodiments of the present disclosure. As depicted, the microelectrodes 229-1, 229-2, 229-3 have been overmolded with the overmolding material 261. In some embodiments, the ablation fixture 270 can include an ablation reference point 271, which can be referenced by an ablation tool, in some embodiments. Although a location of the ablation reference point 271 is depicted as being proximal to the overmolded inboard understructure 260, the reference point 271 can be located distally with respect to the overmolded inboard understructure 260, and/or to either side of the overmolded inboard understructure 260. The ablation tool can be a laser and/or other type of ablation tool, in some embodiments, which can reference the reference point 271 such that the overmolding material 261 covering (e.g., covering an outer surface of) the microelectrodes 229-1, 229-2, 229-3 can be accurately removed by the ablation tool.

In some embodiments, and as depicted, the reference point 271 can be located a particular distance away from each of the microelectrodes, represented by line jj, line kk, and line 11. In some embodiments, the ablation tool can ablate the overmolding material 261 proximally and/or distally with respect to an end point of each of the lines to remove the overmolding material 261 from the outer surface of the microelectrodes 229-1, 229-2, 229-3. In some embodiments, the ablation tool can be programmed to ablate at specific locations based on programmable instructions. For example, a processor (e.g., computer) can execute computer executable instructions stored on a non-transitory computer readable medium to cause the ablation tool to ablate at specific locations.

Figure 10B:
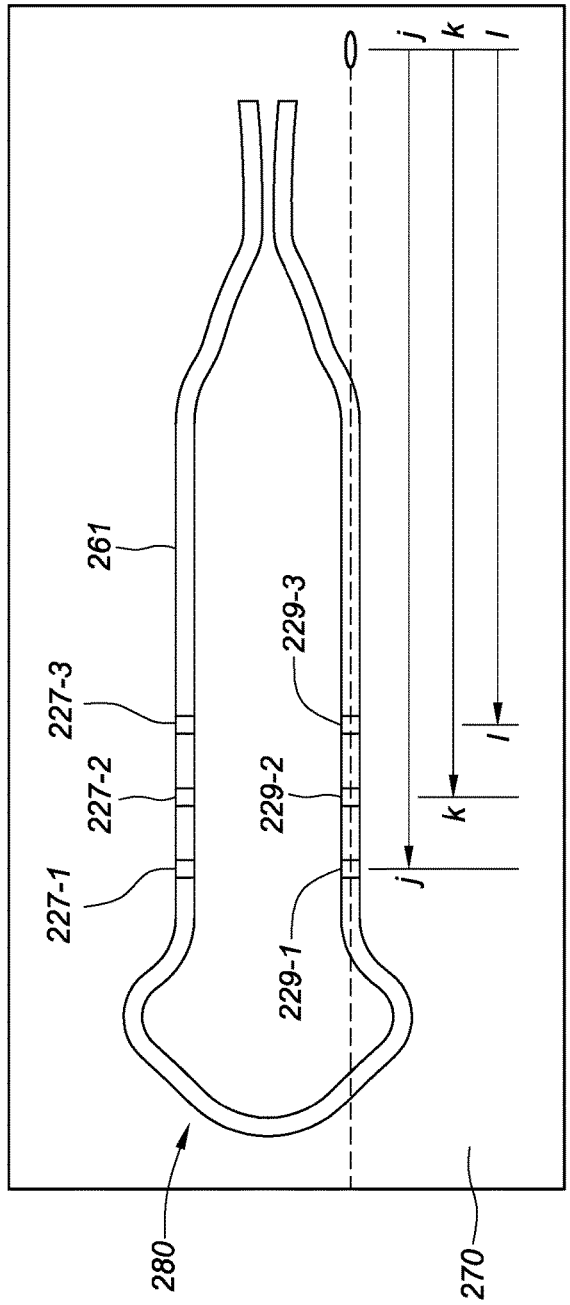
FIG. 10B depicts a top view of the ablation fixture in FIG. 10A after an ablation processing step has been completed and an ablated overmolded inboard understructure, according to various embodiments of the present disclosure.
Figure 10C:
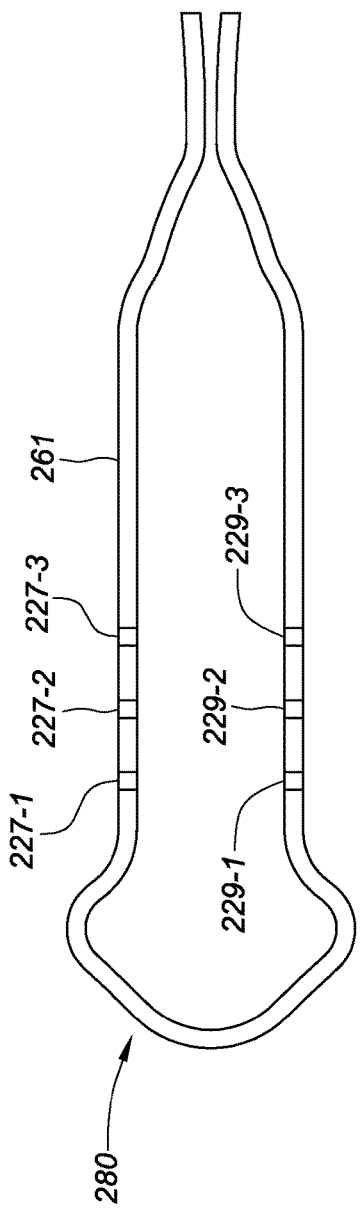
FIG. 10C depicts a top view of the ablated overmolded inboard understructure after being ejected from the ablation fixture depicted in FIG. 10B, according to various embodiments of the present disclosure.

FIG. 10B depicts a top view of the ablation fixture 270 in FIG. 10A after an ablation processing step has been completed and an ablated overmolded inboard understructure 280, according to various embodiments of the present disclosure. As depicted, the overmolding material 261 has been removed from the microelectrodes 227-1, 227-2, 227-3, 229-1, 229-2, 229-3, thus exposing the microelectrodes 227-1, 227-2, 227-3, 229-1, 229-2, 229-3. In some embodiments, overmolding material 261 can be removed from the proximal termination contact pads 235 in a similar manner. In some embodiments, a first side of the overmolded inboard understructure 260 can be ablated and can then be turned over so a second side of the partially ablated inboard understructure can be ablated. Thus, the overmolding material 261 can be circumferentially removed from the overmolded inboard understructure 260. FIG. 10C depicts a top view of the ablated overmolded inboard understructure 280 after being ejected from the ablation fixture 270, according to various embodiments of the present disclosure.

FIG. 11 depicts mechanical properties of various materials that can be used for forming understructures of the flexible tip portion 110, according to various embodiments of the present disclosure. In some embodiments, as discussed herein, the understructure can be formed from a flexible material. In some embodiments, the flexible material can be a super elastic material, such as Nitinol. Examples of Nitinol can include Nitinol available from NDC; Cu doped Nitinol available from Johnson Matthey Medical Components; Nitinol available from Fort Wayne Metals; and/or Nitinol available from Euroflex.

In some embodiments, the flexible material forming the understructure can include a flexible substrate. In some embodiments, the understructures of the flexible tip portion 110 can be formed from a flexible substrate, such as a polymer and/or printed circuit board, as discussed herein. In some embodiments, the flexible substrate can have mechanical properties that are similar to Nitinol. For example, the flexible substrate can have an elastic modulus that is the same or similar to Nitinol; an ultimate tensile strength that is the same or similar to Nitinol; a loading plateau that is the same or similar to Nitinol; and/or a flexural strength that is the same or similar to Nitinol. In some embodiments, the flexible substrate can include a liquid crystalline polymer (LCP) circuit material, such as Ultralam 3850HT available from Rogers Corporation; a glass microfiber reinforced polytetrafluoroethylene (PTFE) composite such as RT/duroid® 5870/5880 available from Rogers Corporation; a glass-reinforced epoxy laminate (FR4) in accordance with IPC 4101C/21/24/26/121/124/129; a glass-reinforced epoxy laminate (FR4) in accordance with Characterization of the material properties of two FR4 printed circuit board laminates, E. T. Haugan and P. Dalsjo, Norwegian Defense Research Establishment (FFI), Report 10 Jan. 2014; S1141 available from Shengyi Sci. Tech. Co. Ltd.; FR408HR available from Isola Group; a Bismaleimide/Triazine (BT) and epoxy resin blend such as BT G200 available from Isola; and/or a Bismaleimide/Triazine (BT) and epoxy resin blend such as N5000-32 available from Nelco®.

In some embodiments, the flexible tip portion 110 depicted in FIGS. 1A and 1B can have an array buckling force of less than or equal to 200 grams of force. For example, to cause the flexible tip portion 110 to deflect, an amount of force less than or equal to 200 grams of force can be applied to the flexible tip portion. For instance, the flexible tip portion can be deflected as shown in FIG. 1B when an amount of force less than or equal to 200 grams of force has been applied to a distal end of the flexible tip portion, which can be formed from the materials discussed herein.

Figure 12A:
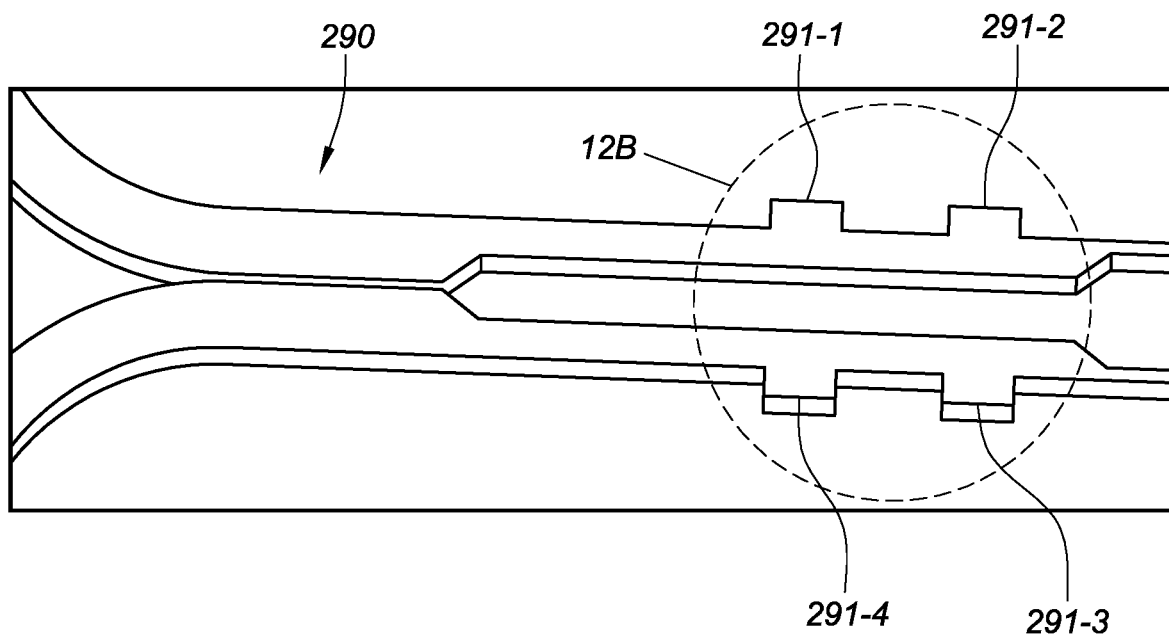
FIG. 12A depicts a top view of a proximal end of an inboard understructure, according to various embodiments of the present disclosure.

FIG. 12A depicts a top view of a proximal end of an inboard understructure 290, according to various embodiments of the present disclosure. In some embodiments, the inboard understructure 290 can include frame locks 291-1, 291-2, 291-3, 291-4 on the proximal end of the inboard understructure 290. It should be noted that an outboard understructure can include frame locks that correspond with frame locks 291-1, 291-2, 291-3, 291-4 on the inboard understructure.

Figure 12B:
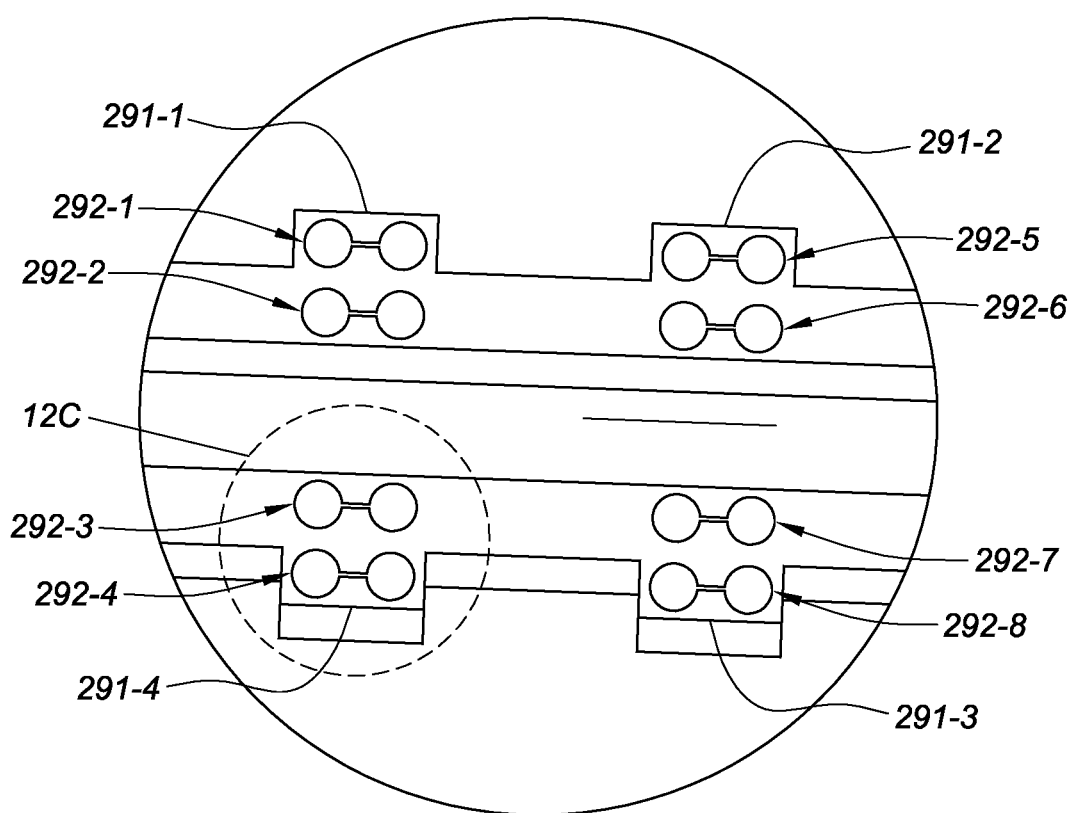
FIG. 12B depicts a top view of an enlarged portion (indicated by dotted circle 12B) of the frame locks depicted on a proximal end of the inboard understructure depicted in FIG. 12A, according to various embodiments of the present disclosure.

FIG. 12B depicts a top view of an enlarged portion (indicated by dotted circle 12B) of frame locks 291-1, 291-2, 291-3, 291-4 depicted on a proximal end of the inboard understructure depicted in FIG. 12A, according to various embodiments of the present disclosure. In some embodiments, one or more electrical connections 292-1, 292-2, . .

. 292-8 can be disposed on one or more of the frame locks 291-1, 291-2, 291-3, 291-4 and/or on one of the arms of the understructure. For example, the electrical connections 292-1, 292-2, . . . 292-8 can be formed on a proximal portion of the arms of the understructure.

Figure 12C:
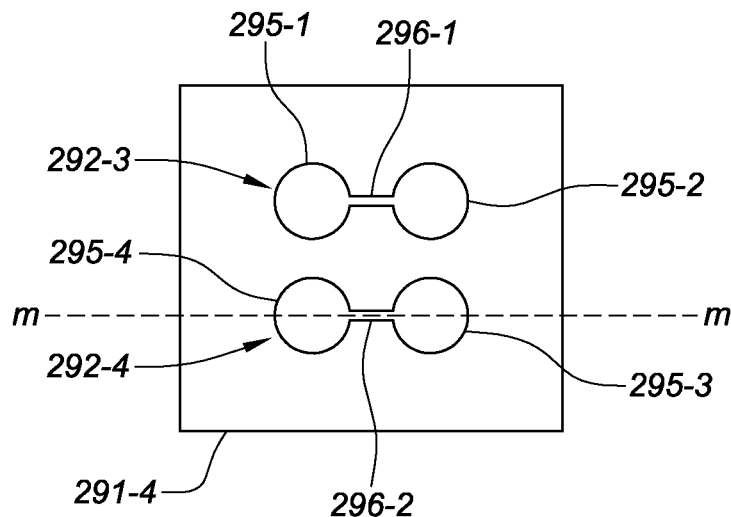
FIG. 12C depicts a top view of an enlarged portion (indicated by dotted circle 12C) of electrical connections depicted in FIG. 12B, according to various embodiments of the present disclosure.

FIG. 12C depicts a top view of an enlarged portion (indicated by dotted circle 12C) of electrical connections 292-3, 292-4 depicted in FIG. 12B, according to various embodiments of the present disclosure. In some embodiments, a third electrical connection 292-3 can include a distal contact pad 295-1 and a proximal contact pad 295-2 and a fourth electrical connection 292-4 can include a distal contact pad 295-4 and a proximal contact pad 295-3. As discussed herein, the electrical connections can be disposed on the proximal portion of an understructure of the flexible tip portion 110. In some embodiments, the electrical connections can be insulated from the understructure (e.g., where the understructure is electrically conductive) to prevent short circuiting from occurring between the electrical connections. With reference to the fourth electrical connection 295-4, the distal contact pad 295-4 and the proximal contact pad 295-3 can be electrically couple to one another via a trace 296-2.

Figure 12D:
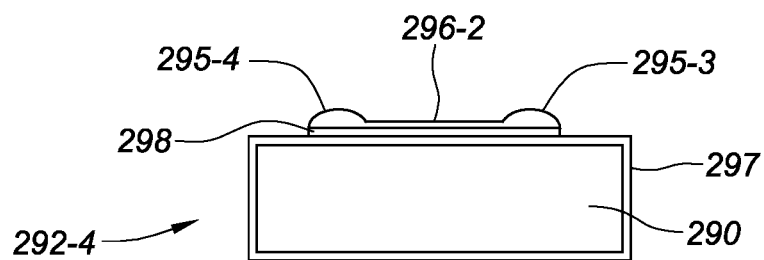
FIG. 12D is a cross-sectional view of FIG. 12C along line mm, according to various embodiments of the present disclosure.

FIG. 12D depicts a cross-sectional view of FIG. 12C along line mm, according to various embodiments of the present disclosure. In some embodiments, the understructure 290 can be coated with a dielectric 297 material, such as parylene. The dielectric material 297 can electrically insulate the electrical connections from a conductive understructure 290, as discussed herein. In some embodiments, a metallization can be completed on a surface of the dielectric, thus allowing for a secure connection between the electrical connection 292-4 to the understructure 290. In an example, a metal such as aluminum can be deposited on the surface of the dielectric material 297 and the electrical connection 292-4 can be disposed on top of the metal 298.

Figure 12E:
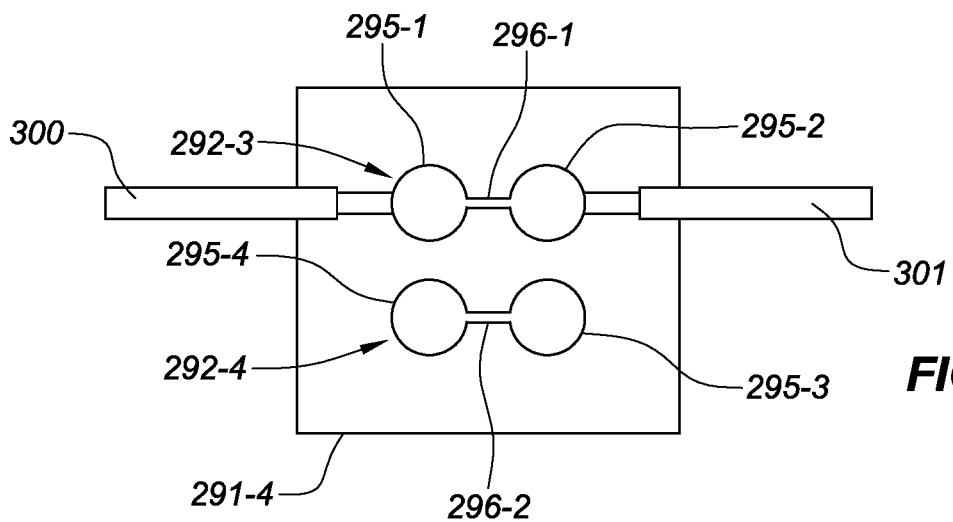
FIG. 12E depicts a top view of wires electrically coupled via an electrical connection, according to various embodiments of the present disclosure.

FIG. 12E depicts a top view of wires electrically coupled via an electrical connection depicted in 12C, according to various embodiments of the present disclosure. In an example, a distally running wire 300 and/or a proximally running wire 301 can be electrically coupled to the third electrical connection 292-3. In some embodiments the distally running wire 300 and the proximally running wire 301 can be connected via the third electrical connection 292-3. In an example, the distally running wire 300 can be soldered to the distal contact pad 295-4 and/or the proximally running wire 301 can be soldered to the proximal contact pad 295-3. In some embodiments where the flexible tip portion does not include electrically conductive traces that are electrically coupled with each of the microelectrodes, wires (e.g., distally running wires) can be electrically coupled with each of the microelectrodes.

In some embodiments, a proximal end of the distally running wires can be electrically coupled with distal contact pads of each of the electrical connections. Accordingly, the flexible tip portion 110 can be formed as a module, wherein the individual distally running wires are connected at a distal end to each of the microelectrodes and at a proximal end to a distal contact pad of the electrical connections. In some embodiments, the proximal contact pad can be left open (e.g., a wire may not be electrically coupled to the proximal contact pad) such that the module can be tested. For example, each of the proximal contact pads can be probed with an electrical testing device to establish that continuity exists and that a signal noise associated with each of the microelectrodes and associated distally running wire does not exceed a defined amount. This can be accomplished prior to assembling the entire high density electrode mapping catheter 101.

In contrast, some prior methods assemble the entire high density electrode mapping catheter 101 before testing is performed. In addition, the electrical connectors can decrease a complexity associated with connecting the proximally running wires and the distally running wires of the high density electrode mapping catheter 101. For example, rather than directly connecting the proximally and distally running wires, the proximal end of the distally running wire can be coupled with the distal pad of the electrical connection and the distal end of the proximally running wire can be coupled with the proximal pad of the electrical connection.

In some embodiments, a pre-made substrate (e.g. flex substrate) can be employed, wherein the pre-made substrate includes the electrical connections and can be bonded to the understructure (e.g., the parylene coated frame). In an example, the substrate design can copy the basic electrical connection configuration discussed and depicted in relation to FIGS. 12B to 13B. This can allow for a microelectrode density to be increased on an array formed by the flexible tip portion 110 (e.g. increase number of microelectrodes from 22 to 32 to 64) by forming multilayer substrates. In some embodiments, the pre-made substrate can be attached to the understructure using adhesive materials, such as epoxy.

Figure 13A:
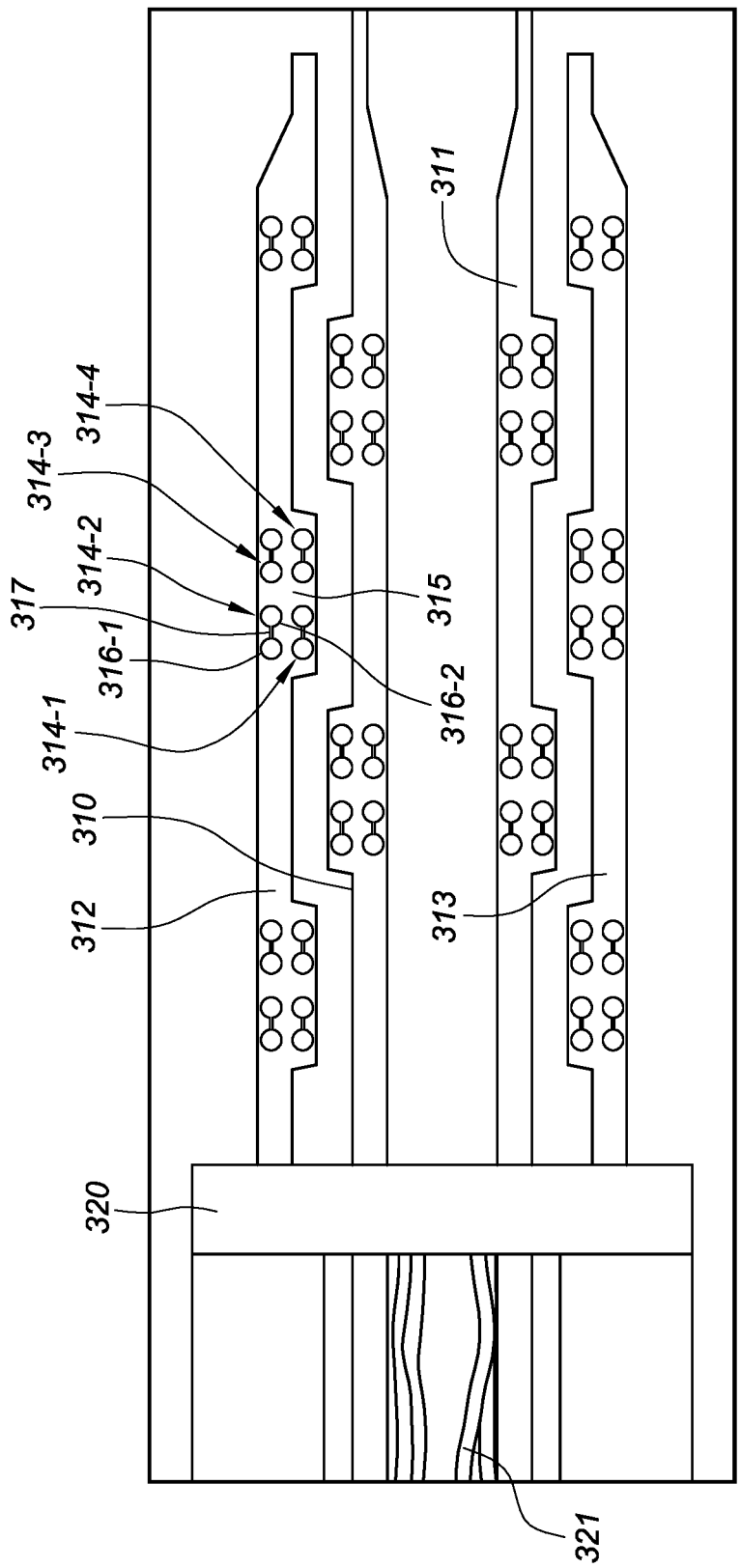
FIG. 13A depicts a top view of a plurality of electrical connections disposed on a first inboard arm; second inboard arm, first outboard arm; and second outboard arm of a flexible framework of a flexible tip portion of the high density electrode mapping catheter, according to various embodiments of the present disclosure.

FIG. 13A depicts a top view of a plurality of electrical connections disposed on an first inboard arm 310; second inboard arm 311, first outboard arm 312; and second outboard arm 313 of a flexible framework of a flexible tip portion 110 of the high density electrode mapping catheter 101, according to various embodiments of the present disclosure. The plurality of electrical connections are generally discussed in relation to electrical connections 314-1, 314-2, 314-3, 314-4. As discussed in relation to FIGS. 12A to 12E, the electrical connections can be disposed on frame locks (e.g., frame lock 315) and/or a proximal portion of the arms 310, 311, 312, 314. In some embodiments, a number of electrical connections disposed on each frame lock can range from 1 to 10. Electrical connection density can be increased in accordance with targeted device dimensions and pad/trace line and space requirements. If the design provides sufficient real estate, the number of connections can be increased as needed. With reference to a first electrical connection 314-1, each of the electrical connections can include a proximal contact pad and a distal contact pad electrically coupled by a trace 317. For example, the first electrical connection 314-1 can include a distal contact pad 316-1 and a proximal contact pad 316-2 connected by a trace 317, as discussed herein.

Figure 13B:
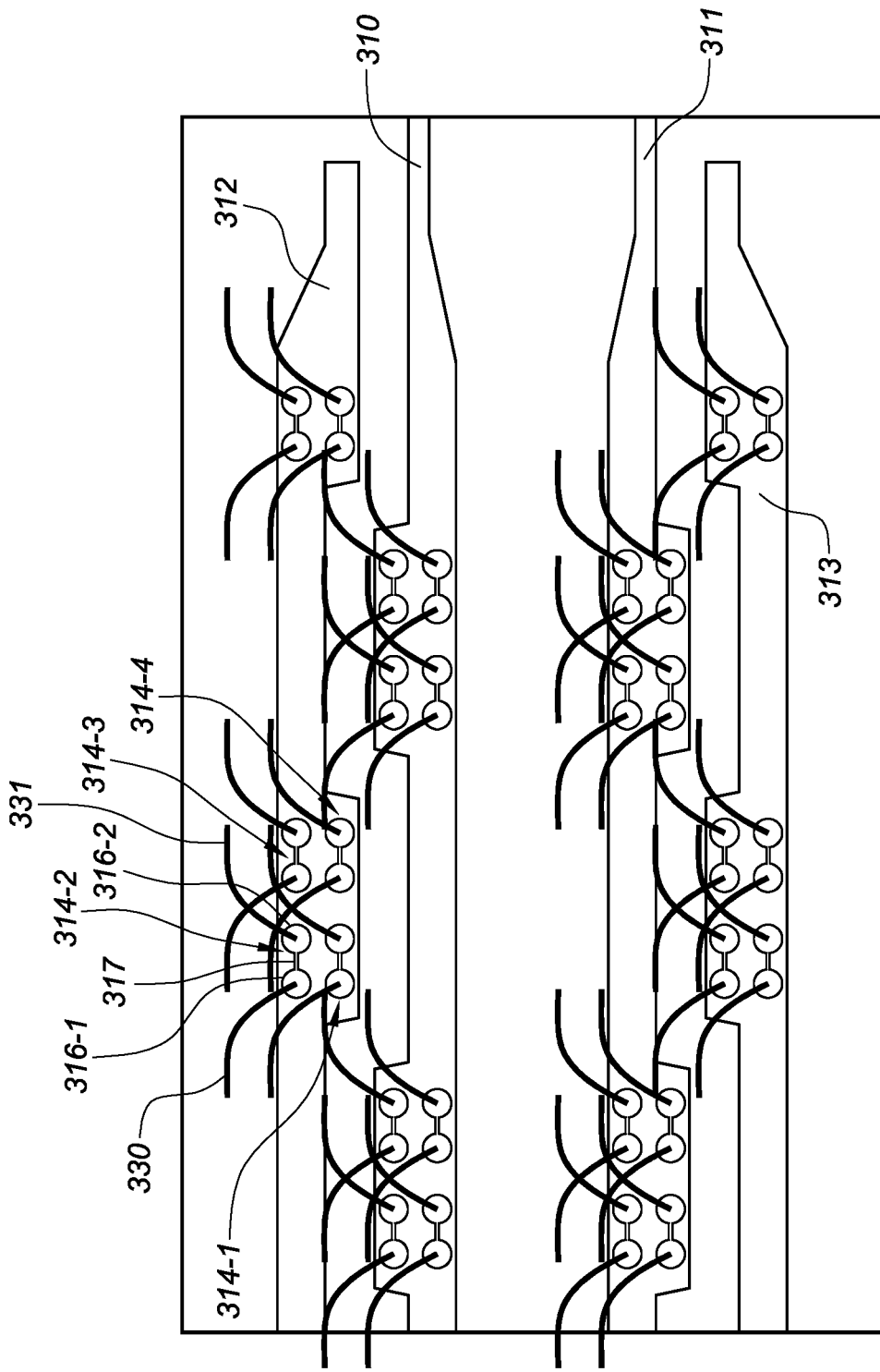
FIG. 13B depicts a top view of a subset of the electrical connections disposed on an first inboard arm; second inboard arm, first outboard arm; and second outboard arm of a flexible framework of a flexible tip portion of the high density electrode mapping catheter depicted in FIG. 13A, according to various embodiments of the present disclosure.

In some embodiments, distally extending wires, for example distally extending wire 321 can extend distally along the flexible framework of the high density electrode mapping catheter 101. As depicted in FIG. 13B, a proximal end of each of the distally extending wires can be electrically coupled to a distal contact pad (e.g., distal contact pad 316-1) of each of the electrical connections. Connection of the distal end of each of the distally extending wires can result in a single module that can be tested, as discussed herein.

In some embodiments, each of the arms can extend through a torsional spacer 320, which can be configured to maintain an alignment between the arms. In some embodiments, an overmolding and ablation process can be employed, as discussed in relation to FIGS. 9A to 10C, which can overmold each arm of the flexible framework (e.g., arms 310, 311, 312, 314) as well as the torsional spacer 320. In addition, the connector 108, depicted in FIGS. 1A and 1B, can be overmolded as well. In some embodiments, an overmolding material can include PEBAX® as discussed herein.

FIG. 13B depicts a top view of a portion of a subset of the electrical connections disposed on a first inboard arm 310; second inboard arm 311, first outboard arm 312; and second outboard arm 313 of a flexible framework of a flexible tip portion 110 of the high density electrode mapping catheter 101 depicted in FIG. 13A, according to various embodiments of the present disclosure. The subset of electrical connections is generally discussed in relation to electrical connections 314-1, 314-2, 314-3, 314-4. In an example, a proximal end of each of a plurality of distally extending wires can be electrically coupled to a respective one of a plurality of distal contact pads of each of the plurality of electrical connections and a distal end of each of a plurality of proximally extending wires can be electrically coupled to a respective one of proximal contact pads of each of the plurality of electrical connections. For example, with specific reference to electrical connection 314-2, distally extending wire 330 and proximally extending wire 331, the proximal end of the distally extending wire 330 can be electrically coupled to the distal contact pad 316-1 and the distal end of the proximally extending wire 331 can be electrically coupled to the proximal contact pad 316-2 of the electrical connection 314-2. The contact pads 316-1, 316-2 can be electrically coupled via the trace 317 as discussed herein, and thus the wires 330, 331 can be electrically coupled with one another.

Figure 14:
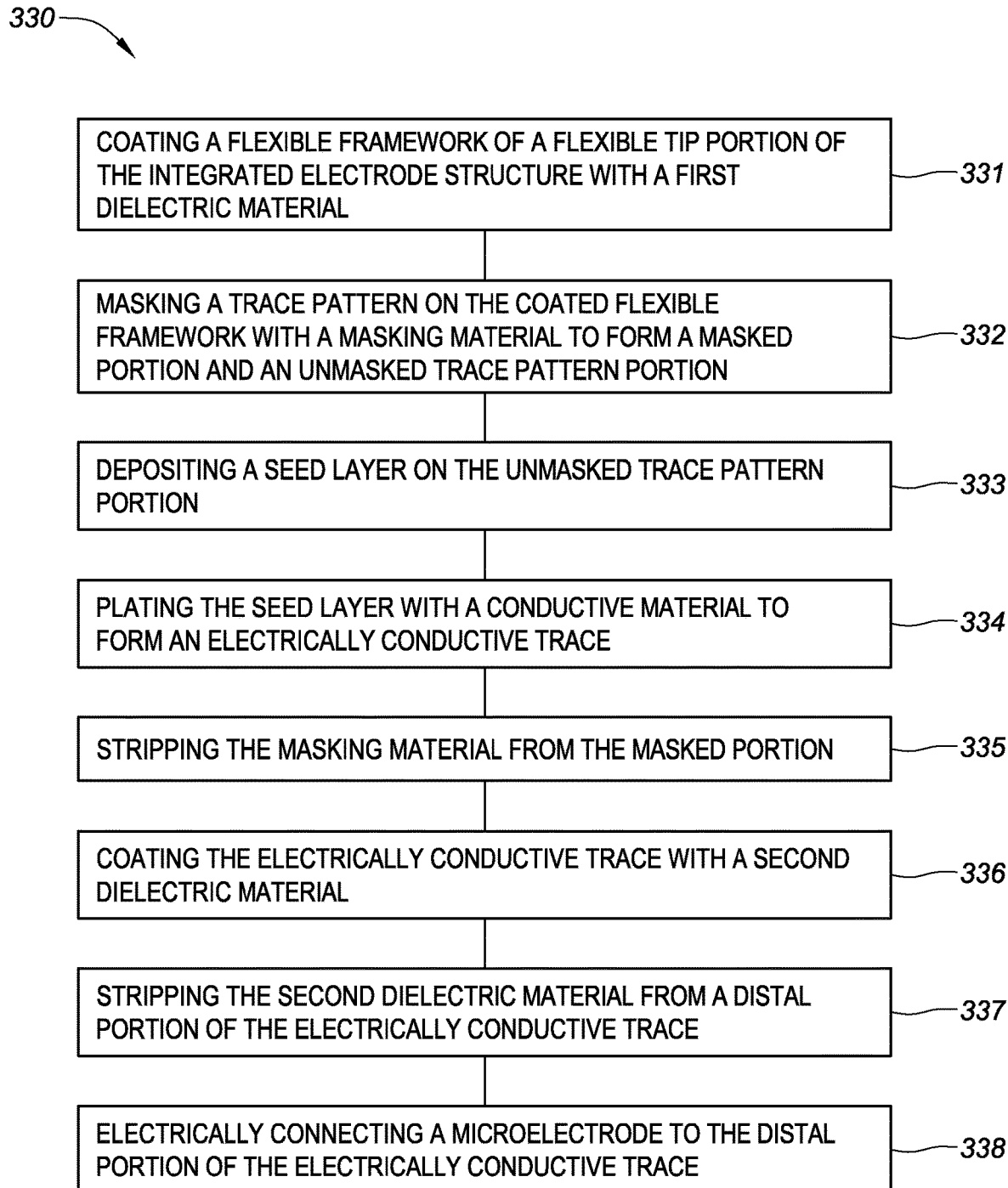
FIG. 14 depicts a method flow diagram for a process for forming an integrated electrode structure that includes a conductive understructure, according to various embodiments of the present disclosure.

FIG. 14 depicts a method flow diagram 340 for a process for forming an integrated electrode structure that includes a conductive understructure, according to various embodiments of the present disclosure. In some embodiments, the method can include coating a flexible framework of a flexible tip portion of the integrated electrode structure with a first dielectric material at step 331. A trace pattern on the coated flexible framework can be masked with a masking material to form a masked portion and an unmasked trace pattern portion at step 332. In some embodiments, a seed layer can be deposited on the unmasked trace pattern portion at step 333. The method can include plating the seed layer with a conductive material to form an electrically conductive trace at step 334. At step 335, the method can include stripping the masking material from the masked portion.

The method can include coating the electrically conductive trace with a second dielectric material at step 336. At step 337, the method can include stripping the second dielectric material from a distal portion of the electrically conductive trace. The method can include electrically connecting a microelectrode to the distal portion of the electrically conductive trace at step 338. Electrically connecting the microelectrode to the distal portion of the electrically conductive trace can include masking the flexible framework of the integrated electrode structure proximally and distally with respect to the distal portion of the electrically conductive trace to form a mask defined area; depositing a second seed layer across the mask defined area; and plating the mask defined area with an electrically conductive material to form the microelectrode, as discussed herein. In some embodiments, masked portions of the flexible framework can be stripped of the masking material, as discussed herein. In some embodiments wherein the microelectrodes are to extend circumferentially around the flexible framework, the method can include circumferentially masking the flexible framework of the integrated electrode structure proximally and distally with respect to the distal portion of the electrically conductive trace to form a circumferential mask defined area.

In some embodiments, the microelectrode may not be formed through a plating process (e.g., depositing a conductive material to form the microelectrode), rather a hollow cylindrical band can be electrically connected to the distal portion of the electrically conductive trace, wherein the hollow cylindrical band is coaxial with the flexible framework of the flexible tip portion. In some embodiments, electrically connecting the hollow cylindrical band to the distal portion of the electrically conductive trace can include depositing solder on the distal portion of the electrically conductive trace; coaxially aligning the hollow cylindrical band with the distal portion of the electrically conductive trace and the flexible framework; and reflowing the solder to electrically couple the hollow cylindrical band with the distal portion of the electrically conductive trace.

Figure 15:
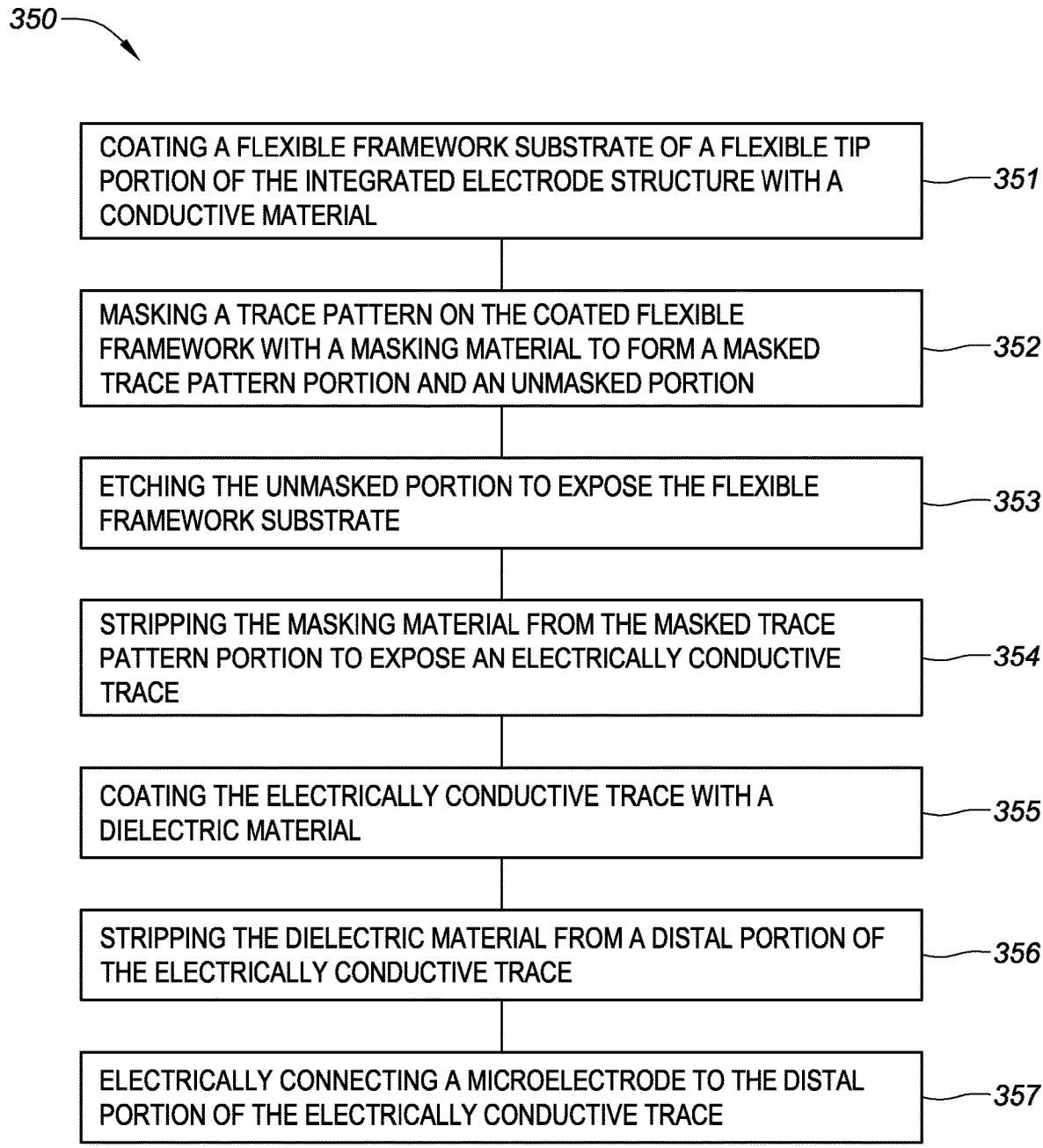
FIG. 15 depicts a method flow diagram for a process for forming an integrated electrode structure that includes a substrate understructure, according to various embodiments of the present disclosure.

FIG. 15 depicts a method flow diagram 350 for a process for forming an integrated electrode structure that includes a substrate understructure, according to various embodiments of the present disclosure. In some embodiments, the method can include coating a flexible framework substrate of a flexible tip portion of the integrated electrode structure with a conductive material at step 351. In some embodiments, the flexible framework can be formed of a flexible substrate. The method can include masking a trace pattern on the coated flexible framework with a masking material to form a masked trace pattern portion and an unmasked portion at step 352. At step 353, the method can include etching the unmasked portion to expose the flexible framework substrate. In some embodiments, the method can include stripping the masking material from the masked trace pattern portion to expose an electrically conductive trace at step 354. The method can include coating the electrically conductive trace with a dielectric material at step 355. In some embodiments, the method can include stripping the dielectric material from a distal portion of the electrically conductive trace at step 356. At step 357, the method can include electrically connecting a microelectrode to the distal portion of the electrically conductive trace.

As discussed herein, the method can further include overmolding the integrated electrode structure with a polymer such as PEBAX®, in some embodiments. The overmolding can be removed from an outer surface of the microelectrode via a ablating step, as discussed herein, in some embodiments.

FIG. 16 depicts a side view of an arm 369 of the high density electrode mapping catheter, according to various embodiments of the present disclosure. In some embodiments, a dielectric material 371 can coat an understructure 370 of the arm 369 of the high density electrode mapping catheter. In some embodiments, one or more electrically conductive traces 372 can be formed on an outer facing surface of the dielectric material 371 (facing away from the understructure 370), as discussed herein. For example, in a manner analogous to that discussed herein, a mask can be applied to the dielectric material 371 to form unmasked trace pattern portions. A seed layer can be applied to coat the unmasked trace pattern portions. The electrically conductive trace 372 can be formed on top of the seed layer, which can adhere the electrically conductive trace 372 to the dielectric material 371.

In some embodiments, multiple layers of electrically conductive traces 372 can be formed on the arm 369 of the high density electrode mapping catheter, as depicted in FIG. 16. One or more additional electrically conductive traces 373 can be formed on a second layer of dielectric material 374. The second layer of dielectric material 374 can be applied over the first layer of dielectric material 371 and over the electrically conductive trace 372. In some embodiments, a first via 375 can be formed in the dielectric material 374 that coats the electrically conductive trace 372. In an example, a mask can be applied over a portion of the electrically conductive trace 372 (e.g., a portion where the via 375 will be formed) before the second layer of dielectric material 374 is applied and/or the second layer of dielectric material 374 can be removed to create the first via 375. Additional electrically conductive traces can be constructed in this manner.

In some embodiments, the additional electrically conductive trace 373 can be applied over a portion of the second layer of dielectric material 374. In an example, a distal end of the additional electrically conductive trace can be disposed proximally with respect to the first via 375. In some embodiments, the additional electrically conductive trace 373 and the electrically conductive trace 372 can run parallel with respect to one another and parallel with respect to the understructure 370. In some embodiments, a third layer of dielectric material 376 can coat a portion (e.g., outer facing surface) of the second layer of dielectric material 374 and the additional electrically conductive trace 373. In some embodiments, a mask can be applied over the additional electrically conductive trace 373 (e.g., a portion where the via 377 will be formed) before the third layer of dielectric material 376 is applied and/or the third layer of dielectric material 376 can be removed to create the via 377 for the second electrically conductive trace 373.

In some embodiments, the mask applied to the electrically conductive trace 372 can be removed after application of the third layer of dielectric material 376, thus creating the first via 375 in the second layer of dielectric material 374 and a second via 378 in the third layer of dielectric material 376 to form via 379. As depicted in FIG. 16, multiple layers of electrically conductive traces 372, 373 can be formed on the understructure 370 of the arm 369. As discussed herein, this can be beneficial when a real estate associated with a surface of the arm 369 is not large enough to support formation of more than a particular number of electrically conductive traces next to one another. Accordingly, some embodiments of the present disclosure can allow for electrically conductive traces to be formed in different layers.

In some embodiments, a similar formation can be formed on another side of the understructure 370 of the arm 369. For example, another side of the arm 369 (e.g., opposite side of the arm 369 with respect to the electrically conductive traces 372, 373) can include a similar formation that supports formation of electrically conductive traces in different layers, as discussed herein.

Figure 17A:
FIGS. 17A to 17F depict a side view of an arm of the high density electrode mapping catheter and associated processing steps, according to various embodiments of the present disclosure.
Figure 17B:
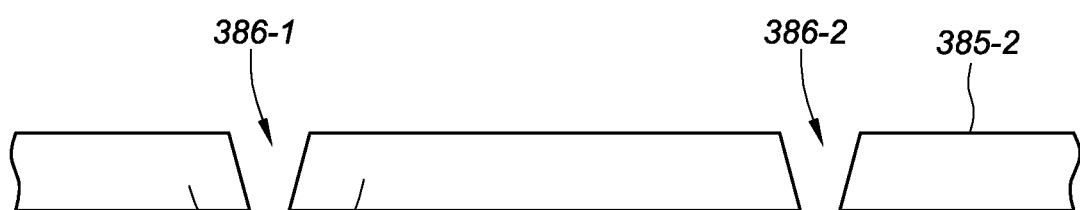
Figure 17C:
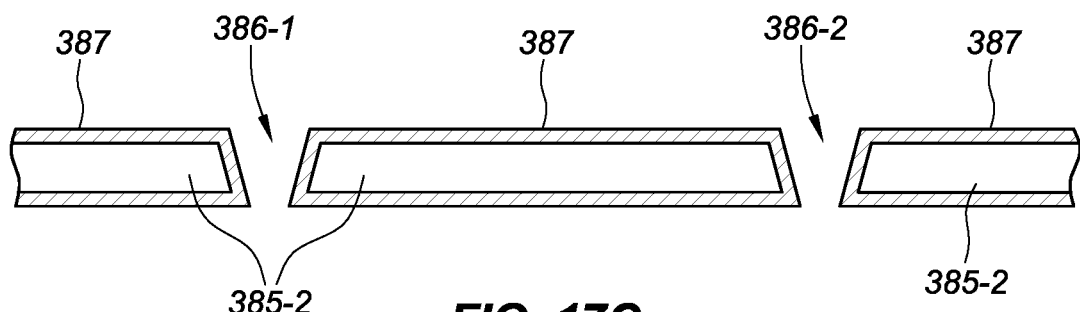

FIGS. 17A to 17E depict a side view of an understructure of an arm of the high density electrode mapping catheter and associated processing steps, according to various embodiments of the present disclosure. FIG. 17A depicts an understructure 385-1 associated with the arm of the high density electrode mapping catheter. As depicted in FIG. 17B, in some embodiments, a first via 386-1 and second via 386-2 can be formed in the understructure 385-2. In an example, the vias 386-1, 386-2 can be cut via a laser, drilled, etc. As depicted in FIG. 17C, in some embodiments, the understructure 385-2 can be coated with a first coating of dielectric material 387, such as parylene, for example.

Figure 17D:
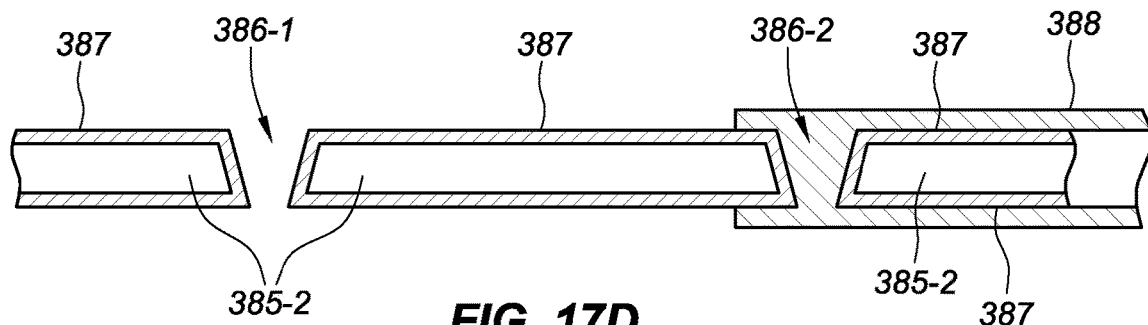

As depicted in FIG. 17D, an electrically conductive trace 388 can be applied on the first coating of dielectric material 387 that coats the understructure 385-2. In some embodiments, the electrically conductive trace 388 can be applied to a top surface and bottom surface associated with the first coating of dielectric material 387 that coats the understructure 352-2. The electrically conductive trace 388 can fill the via 386-2, thus electrically coupling a bottom portion of the electrically conductive trace 388 applied to the bottom surface associated with the first coating of dielectric material 387 and a top portion of the electrically conductive trace 388 applied to the top surface associated with the first coating of dielectric material 387. In some embodiments, the electrically conductive trace 388 can extend proximally with respect to the via 386-2. In some embodiments, the electrically conductive trace 388 can extend distally with respect to the second via 386-2. For example, and as depicted in FIG. 17D, a distal end of the electrically conductive trace 388 can be disposed between the first via 386-1 and the second via 386-2.

Figure 17E:
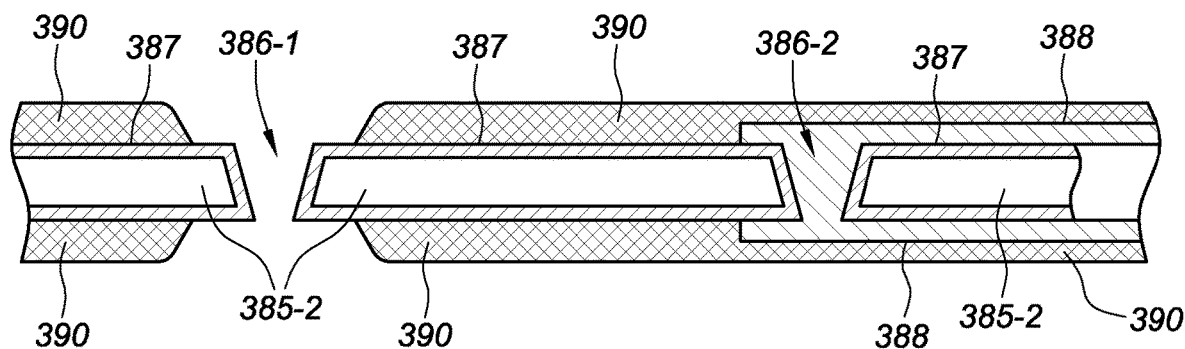
Figure 17F:
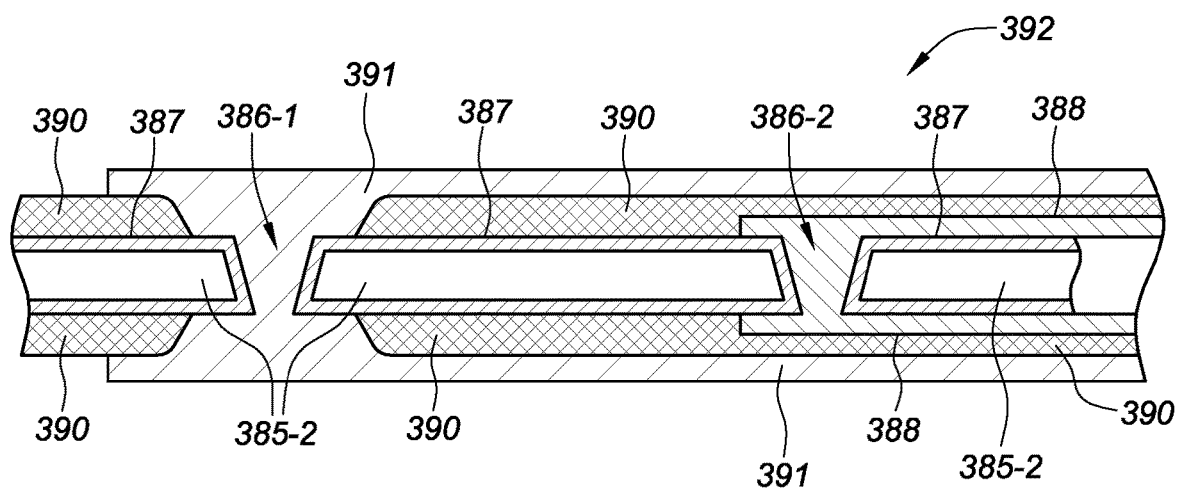

As depicted in FIG. 17E, a second coating of dielectric material 390 can be applied to a top surface and bottom surface of the first coating of dielectric material 387 and the electrically conductive trace 388. In some embodiments, the second coating of dielectric material 390 may not be applied to the first via 386-1 and/or can be removed from the first via 386-1. FIG. 17F depicts a processed understructure 392 that includes a second electrically conductive trace 391 applied to a top surface and bottom surface of the second coating of dielectric material 390. In some embodiments, as depicted in FIG. 17F, the second electrically conductive trace 391 can be applied to the portions of the first coating of dielectric material 387 surrounding the first via 386-1, that are not coated with the second coating of dielectric material 390. In an example, the second coating of dielectric material 390 can be applied proximally and/or distally with respect to the first via 386-1, leaving the first coating of dielectric material 387 exposed for coating with the second electrically conductive trace 391. The second electrically conductive trace 391 can extend along a top portion and a bottom portion of processed understructure 392. The second electrically conductive trace 391 can extend through the via 386-1, thus electrically coupling portions of the second electrically conductive trace 391 extending along the top portion and the bottom portion of the processed understructure 392.

In some embodiments, the first electrically conductive trace 388 can be laterally offset from the second electrically conductive trace 391. As such, a via can be formed in the second coating of dielectric material 390, which can be used to electrically connect a microelectrode or other device to the first electrically conductive trace 388, while electrically insulating the microelectrode or other device from the second electrically conductive trace 391. In some embodiments, a third coating of dielectric material can be applied to the second electrically conductive trace 391 and a microelectrode can be electrically coupled with the second electrically conductive trace 391 through a via formed in the third coating of dielectric material.

Figure 18A:
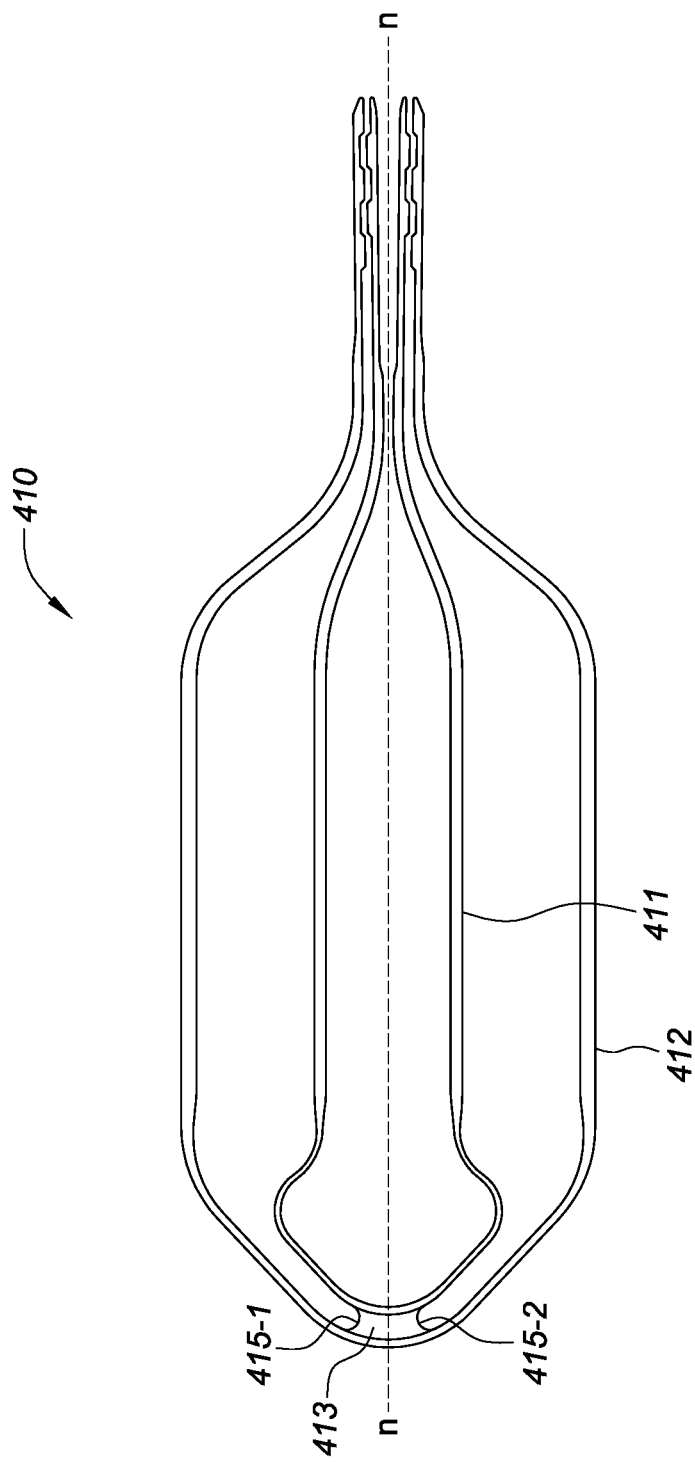

FIGS. 18A to 18G depict top views of embodiments of an understructure of a high density electrode mapping catheter in FIG. 1A, according to various embodiments of the present disclosure. The embodiments depicted in FIGS. 18A to 18G can be constructed from a unitary piece of material. For example, FIG. 18A depicts an understructure 410 that includes an inner understructure 411 (also referred to herein as inboard understructure) and an outer understructure 412 (also referred to herein as outboard understructure), which can be formed from a single piece of material. In some embodiments, the inner understructure 411 and the outer understructure 412 can be laser cut from a single piece of material and/or photo etched from a single piece of material.

As depicted in FIG. 18A, a distal end of the inner understructure 411 can be connected to a distal end of the outer understructure 412 via a connective portion 413. The connective portion 413 can be formed from the same unitary piece of material as the inner understructure 411 and the outer understructure 412. The connective portion 413 can extend from a distal side of the distal end of the inner understructure 411 to a proximal side of the distal end of the outer understructure 412. In some embodiments, the connective portion 413 can be planar and can be equal in thickness with the inner understructure 411 and the outer understructure 412. The connective portion can extend between the distal end of the inner understructure 411 and the distal end of the outer understructure 412 on either side of an understructure longitudinal axis nn defined by the inner understructure 411 and the outer understructure 412, which is depicted in FIG. 18A.

As depicted in FIG. 18A, outer edges 415-1, 415-2 can be radiused toward the understructure longitudinal axis nn. In some embodiments, the radiused outer edges 415-1, 415-2 can help with minimizing strain existing between the inner understructure 411 and the outer understructure 412, as the understructure 410 is inserted and/or deployed from a sheath. For example, in some embodiments where the outer edges are straight, and are not radiused, the portions of the inner understructure 411 and the outer understructure 412 located adjacent to the outer edges of the connective portion 413 can experience an increased strain. In contrast, the radiused outer edges 415-1, 415-2 can better distribute the strain as the understructure 410 is deflected and/or inserted into or deployed from the sheath.

Figure 18B:
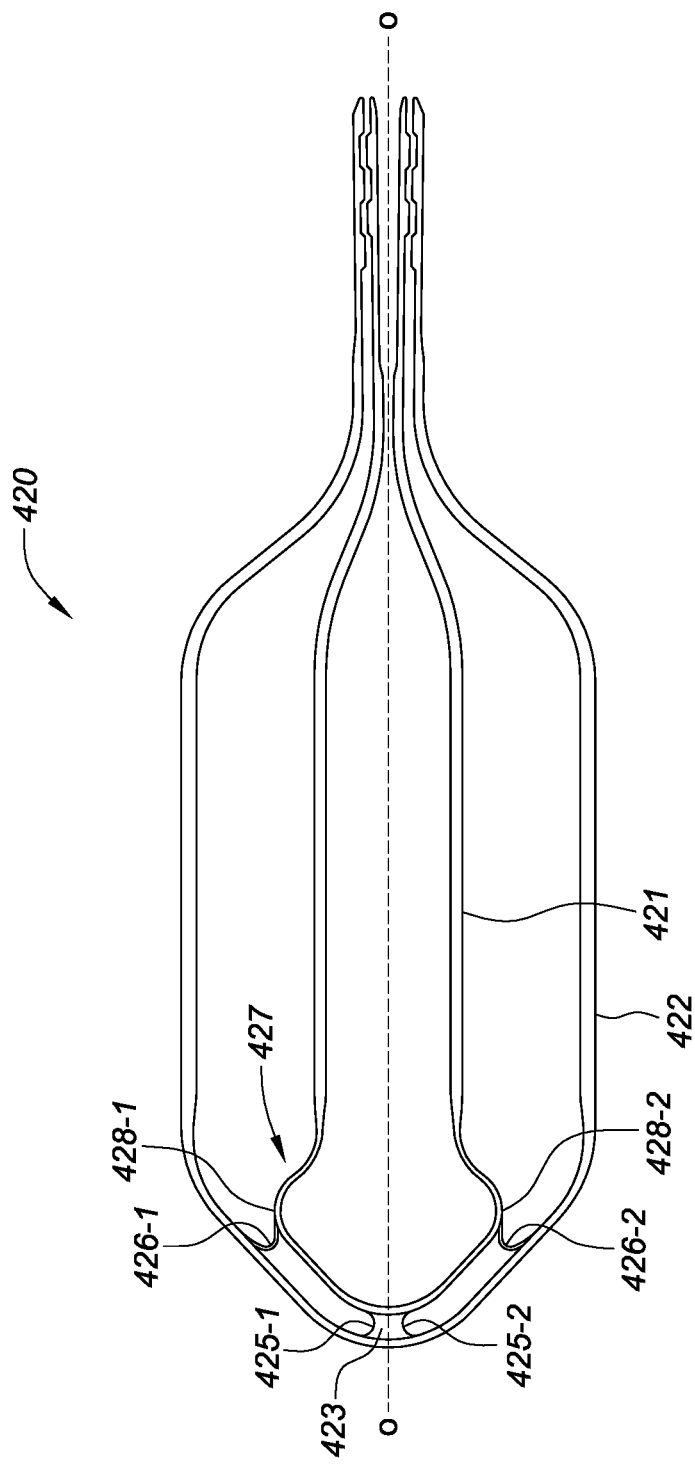

FIG. 18B depicts an embodiment of an understructure 420 that includes an inner understructure 421 and an outer understructure 422. As depicted in FIG. 18B, a distal end of the inner understructure 421 can be connected to a distal end of the outer understructure 422 via a connective portion 423. The connective portion 423 can be formed from a same unitary piece of material as the inner understructure 421 and the outer understructure 422. The connective portion 423 can extend from a distal side of the distal end of the inner understructure 421 to a proximal side of the distal end of the outer understructure 422, in some embodiments.

In some embodiments, the connective portion 423 can be planar and can be equal in thickness with the inner understructure 421 and the outer understructure 422. The connective portion 423 can extend between the distal end of the inner understructure 421 and the distal end of the outer understructure 422 on either side of an understructure longitudinal axis oo defined by the inner understructure 421 and the outer understructure 422, which is depicted in FIG. 18B. In contrast to FIG. 18A, the connective portion 423 may not extend as far to either side of the understructure longitudinal axis oo for reasons discussed herein. As discussed in relation to FIG. 18A, the connective portion can include radiused outer edges 425-1, 425-2, which can better distribute strain between the inner understructure 421, the connective portion 423, and the outer understructure 422, as the understructure 420 is deflected and/or inserted into or deployed from a sheath. In some embodiments, because the connective portion 423 does not extend as far to either side of the understructure longitudinal axis oo, the understructure may be deflected with less force, in some embodiments, and/or can be introduced and/or deployed from a sheath more easily.

In some embodiments, the understructure 420 can include first and second outer connective members 426-1, 426-2, which connect a flared distal head 427 of the inner understructure 421 to the outer understructure 422. For example, the flared distal head 427 can include a first flared segment 428-1 that is flared away from the understructure longitudinal axis oo and a second flared segment 428-2 that is flared away from the understructure longitudinal axis oo. In some embodiments, a first outer connective member 426-1 can connect the first flared segment 428-1 to the outer understructure 422 and a second outer connective member 426-2 can connect the second flared segment 428-2 to the outer understructure 422. The first and second outer connective members 426-1, 426-2 can connect with the outer understructure 422 at points on the outer understructure that are adjacent to a respective one of the first flared segment 428-1 and the second flared segment 428-2.

In some embodiments, the first connective member 426-1 can be flared towards the connective portion 423 and the second connective member 426-2 can be flared towards the connective portion 423, in some embodiments. Alternatively, the first and second connective members 426-1, 426-2 can be flared away from the connective portion 423. By flaring the connective members 426-1, 426-2, the members can be lengthened or shortened as the understructure is deflected and/or inserted into or deployed from a sheath (e.g., slack can built into the connective members 426-1, 426-2). For example, as the understructure 420 is introduced into a sheath, the outer understructure 422 can be compressed towards the understructure longitudinal axis oo, causing an increase in axial length. To compensate for this increase in axial length, the flared distal head 427 can straighten (become less flared) as the outer understructure 422 is compressed and lengthened. This can effectively increase a length of the inner understructure 421, and prevent the inner understructure 421 from pulling on the outer understructure 422, thus preventing the outer understructure 422 from hooking within the sheath. As the inner understructure 421 straightens and elongates, the first and second connective members 426-1, 426-2 can straighten (become less flared) and elongate to allow the outer understructure 422 to elongate. In some embodiments, as the outer understructure 422 is compressed, the first and second connective members 426-1, 426-2 can help pull the first and second flared segments 428-1, 428-2 of the flared distal head 427 and cause the flared distal head 427 to elongate with the outer understructure 422.

Figure 18C:
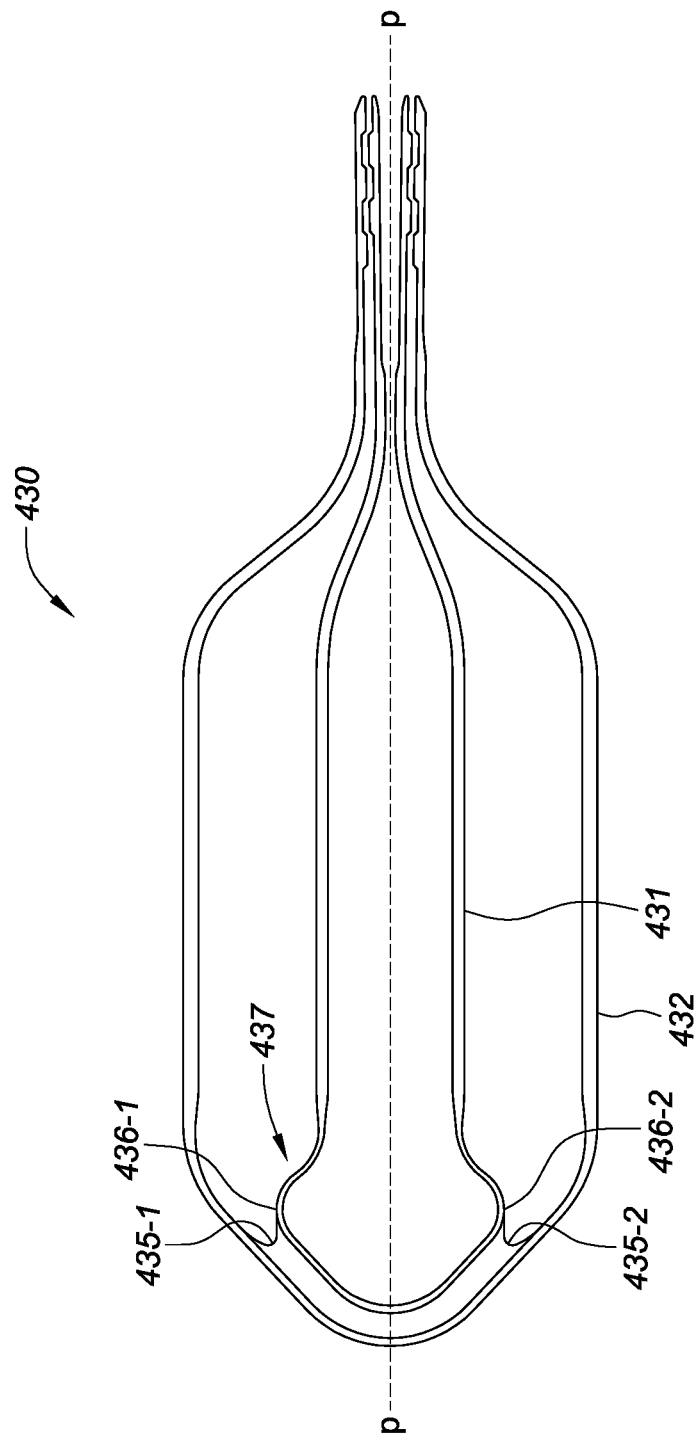

FIG. 18C depicts an understructure 430 that includes an inner understructure 431 and an outer understructure 432, which can be formed from a single piece of material. In some embodiments, the inner understructure 431 and the outer understructure 432 can be laser cut from a single piece of material and/or photo etched from a single piece of material. As depicted in FIG. 18C, a distal end of the inner understructure 431 can be connected to a distal end of the outer understructure 432 via a connective portion 433. The connective portion 433 can be formed from the same unitary piece of material as the inner understructure 431 and the outer understructure 432. The connective portion 433 can extend from a distal side of the distal end of the inner understructure 431 to a proximal side of the distal end of the outer understructure 432. In some embodiments, the connective portion 433 can be planar and can be equal in thickness with the inner understructure 431 and the outer understructure 432. The connective portion 433 can extend between the distal end of the inner understructure 431 and the distal end of the outer understructure 432 on either side of an understructure longitudinal axis pp defined by the inner understructure 431 and the outer understructure 432, which is depicted in FIG. 18C.

As depicted in FIG. 18C, the connective portion 433 can extend from the understructure longitudinal axis pp to an outermost portion of the first and second flared segments 436-1, 436-2. In some embodiments, the connective portion 433 can extend from the understructure longitudinal axis pp to a point that is distal of the outermost portion of the first and second flared segments 436-1, 436-2, as depicted in FIG. 18C. The connective portion 433 can include radiused outer edges 435-1, 435-2, which can better distribute strain as the understructure 430 is deflected and/or inserted into or deployed from a sheath, as discussed in relation to FIG. 18A.

Figure 18D:
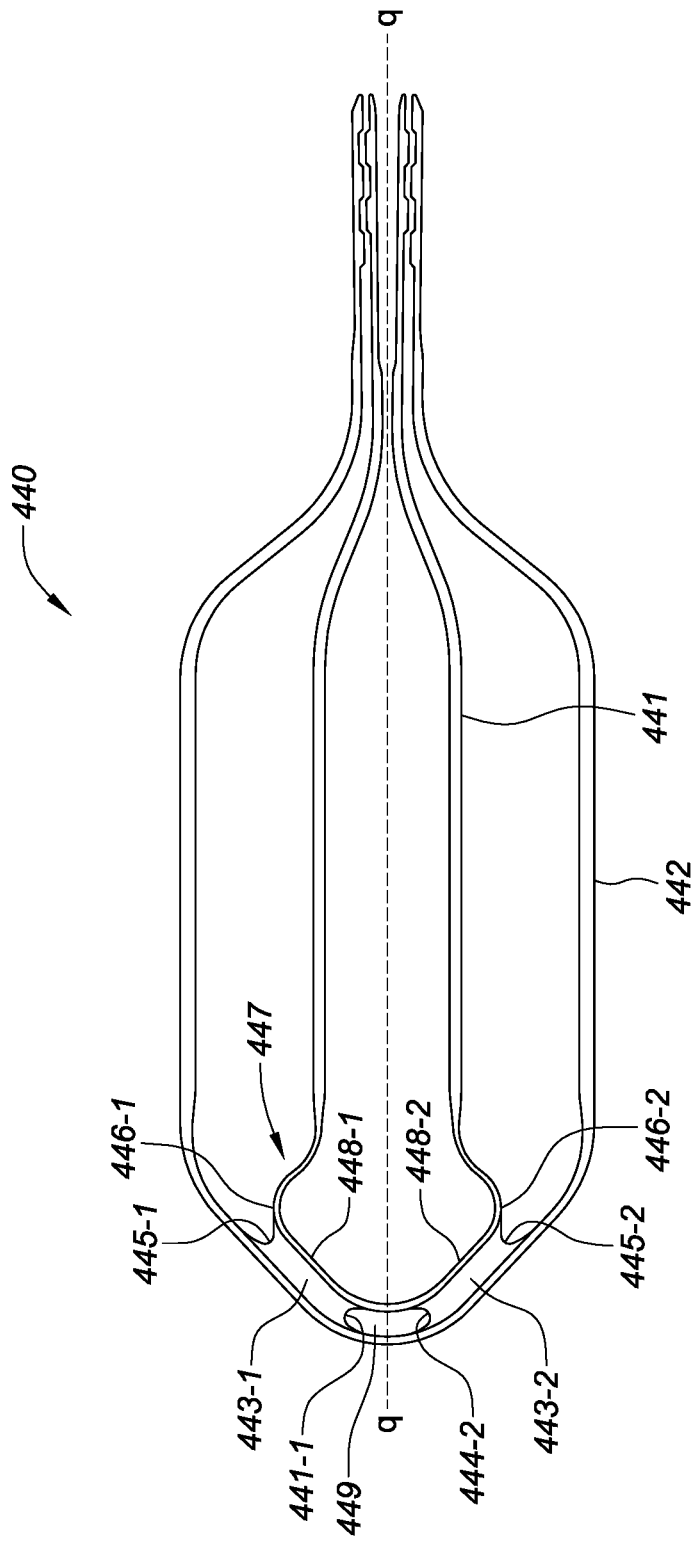

FIG. 18D depicts an understructure 440 that includes an inner understructure 441 and an outer understructure 442, which can be formed from a single piece of material. In some embodiments, the inner understructure 441 and the outer understructure 442 can be laser cut from a single piece of material and/or photo etched from a single piece of material. As depicted in FIG. 18D, a distal end of the inner understructure 441 can be connected to a distal end of the outer understructure 442 via connective portions 443-1, 443-2. The connective portions 443-1, 443-2 can be formed from the same unitary piece of material as the inner understructure 441 and the outer understructure 442. The connective portions 443-1, 443-2 can extend from a distal side of the distal end of the inner understructure 441 to a proximal side of the distal end of the outer understructure 442. In some embodiments, the connective portions 443-1, 443-2 can be planar and can be equal in thickness with the inner understructure 441 and the outer understructure 442. The connective portions 443-1, 443-2 can extend between the distal end of the inner understructure 441 and the distal end of the outer understructure 442 on either side of an understructure longitudinal axis qq defined by the inner understructure 441 and the outer understructure 442, which is depicted in FIG. 18D.

As depicted in FIG. 18D, a first connective portion 443-1 can extend between a first distally angled segment 448-1 of the inner understructure 441 and a corresponding segment of the outer understructure 442. A second connective portion 443-2 can extend between a second distally angled segment 448-2 of the inner understructure 441 and a corresponding segment of the outer understructure 442. In some embodiments, a side of the first connective portion 443-1 located towards the understructure longitudinal axis qq can include an inner edge 444-1 radiused away from the understructure longitudinal axis qq and a side of the second connective portion 443-2 located towards the understructure longitudinal axis qq can include an inner edge 444-2 radiused away from the understructure longitudinal axis qq, such that a gap 449 is defined between the inner edges 444-1, 444-1 of the connective portions 443-1, 443-2 and distal ends of the inner and outer understructures 441, 442. In some embodiments, the gap 449 can allow for better flexibility of the understructure 440 as it is deflected and/or inserted into or deployed from a sheath. In some embodiments, the connective portions 443-1, 443-2 can include outer edges 445-1, 445-2 that are radiused towards the distal end of the understructure 440, as discussed in relation to FIG. 18A. The radiused inner edges 444-1, 444-2 and radiused outer edges 445-1, 445-2 can better distribute strain, as discussed herein.

Figure 18E:
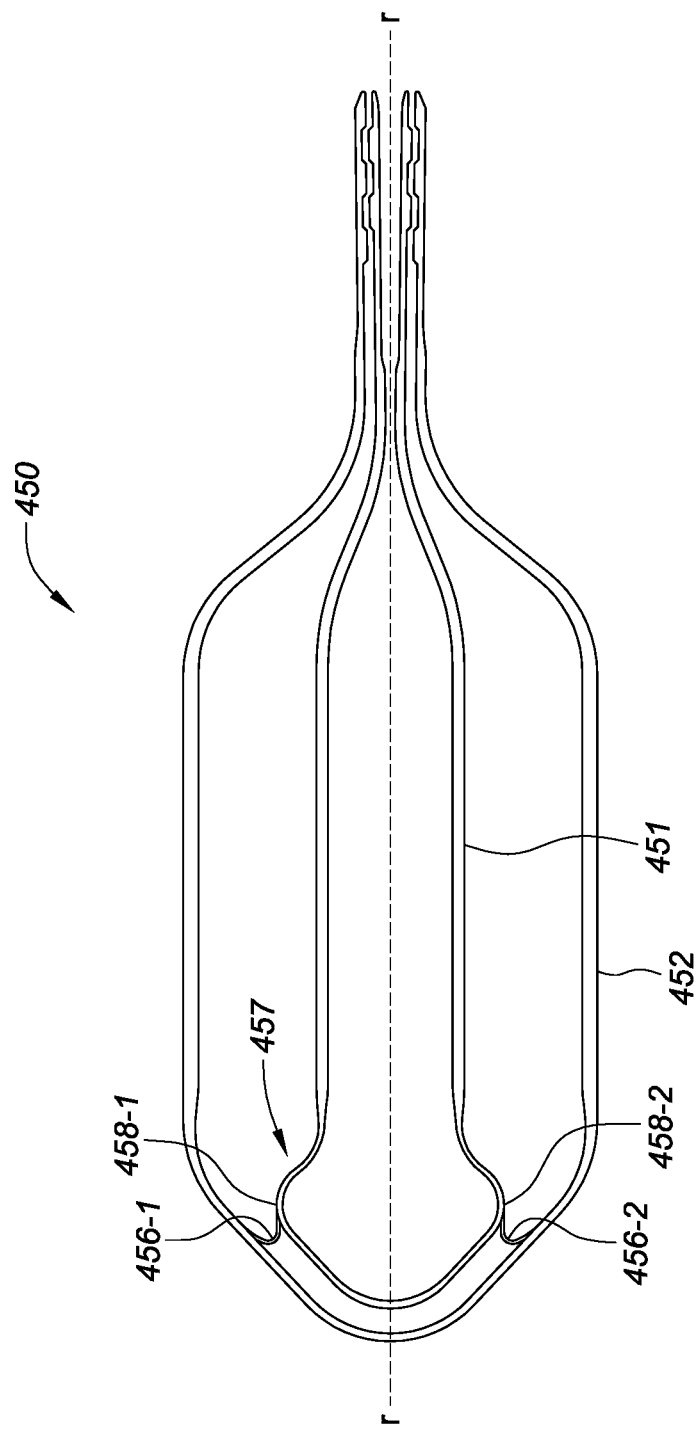

FIG. 18E depicts an embodiment of an understructure 450 that includes an inner understructure 451 and an outer understructure 452. In some embodiments, the understructure 450 can include first and second outer connective members 456-1, 456-2, which connect a flared distal head 457 of the inner understructure 451 to the outer understructure 452. For example, the flared distal head 457 can include a first flared segment 458-1 that is flared away from the understructure longitudinal axis IT and a second flared segment 458-2 that is flared away from the understructure longitudinal axis IT. In some embodiments, a first outer connective member 456-1 can connect the first flared segment 458-1 to the outer understructure 452 and a second outer connective member 456-2 can connect the second flared segment 458-2 to the outer understructure 452. The first and second outer connective members 456-1, 456-2 can connect with the outer understructure 452 at points on the outer understructure 452 that are adjacent to a respective one of the first flared segment 458-1 and the second flared segment 458-2.

In some embodiments, the first connective member 456-1 can be flared towards the distal ends of the inner and outer understructures 451, 452 and the second connective member 456-2 can be flared towards the distal ends of the inner and outer understructures 451, 452, in some embodiments. Alternatively, the first and second connective members 456-1, 456-2 can be flared away from the distal ends of the inner and outer understructures 451, 452. By flaring the connective members 456-1, 456-2, the members can be lengthened or shortened as the understructure 450 is deflected and/or inserted into or deployed from a sheath, as discussed herein.

FIG. 18F depicts an embodiment of an understructure 460 that includes an inner understructure 461-1, 461-2 and an outer understructure 462. In some embodiments, the understructure 460 can include first and second outer connective members 466-1, 466-2, which connect a flared distal head 467 of the inner understructure 461-1, 461-2 to the outer understructure 462. In contrast to FIG. 18E, the inner understructure 461-1, 462-2 can be terminated at a first flared segment 468-1 and a second flared segment 468-2 and may not extend distally from the first and second flared segments 468-1, 468-2. The inner understructure 461-1, 461-2, as depicted, extends proximally from the first and second flared segments 468-1, 468-2. In some embodiments, a first outer connective member 466-1 can connect the first flared segment 468-1 to the outer understructure 462 and a second outer connective member 466-2 can connect the second flared segment 468-2 to the outer understructure 462. The first and second outer connective members 466-1, 466-2 can connect with the outer understructure 462 at points on the outer understructure 462 that are adjacent to a respective one of the first flared segment 468-1 and the second flared segment 468-2.

In some embodiments, the first connective member 466-1 can be flared towards the distal ends of the inner and outer understructures 461-1, 461-2, 462 and the second connective member 466-2 can be flared towards the distal ends of the inner and outer understructures 461-1, 461-2, 462, in some embodiments. Alternatively, the first and second connective members 466-1, 466-2 can be flared away from the distal ends of the inner and outer understructures 461-1, 461-2, 462. By flaring the connective members 466-1, 466-2, the members can be lengthened or shortened as the understructure 460 is deflected and/or inserted into or deployed from a sheath, as discussed herein.

Figure 18G:
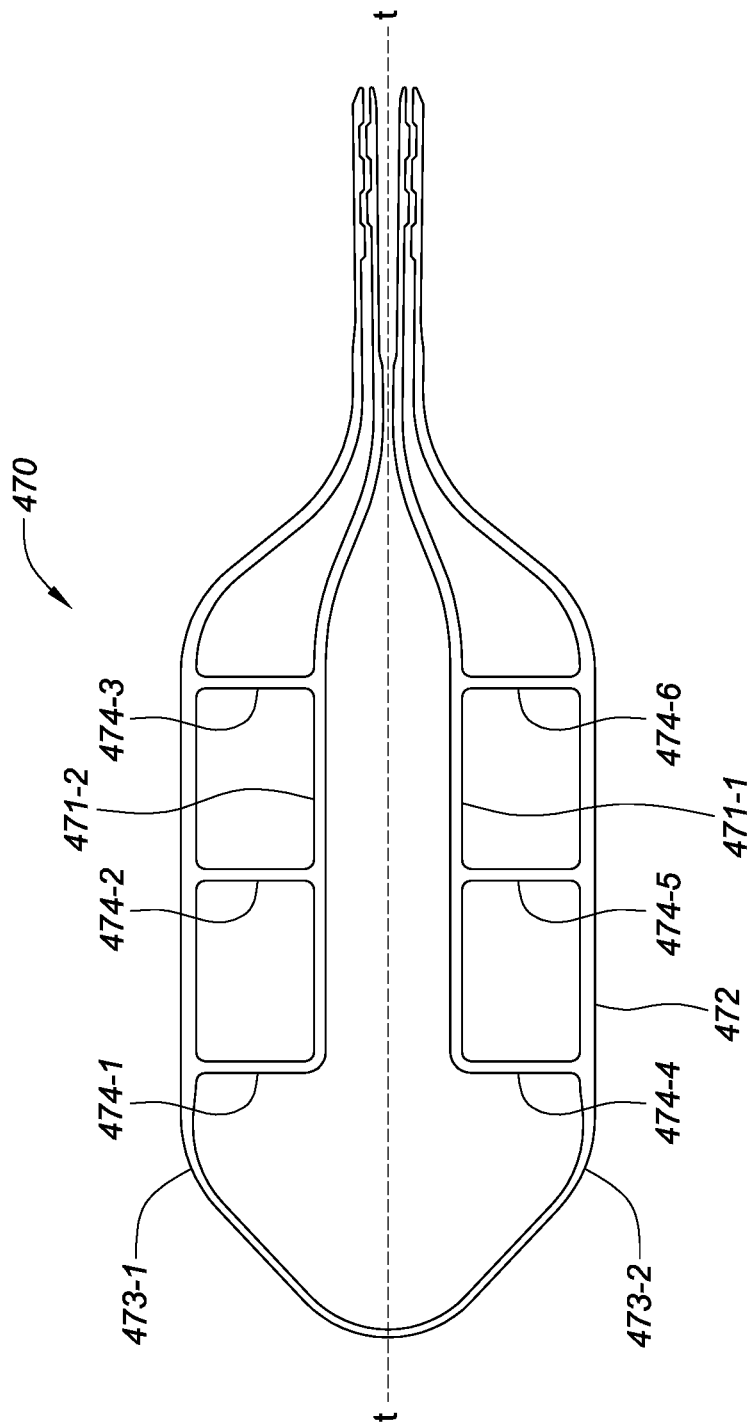

FIG. 18G depicts an embodiment of an understructure 470 that includes an inner understructure 471-1, 471-2 and an outer understructure 472. In some embodiments, a first and second arm of the inner understructure 471-1, 472-2 can extend distally from a proximal end of the understructure 470. A distal portion of the first and second arms of the inner understructure 471-1, 472-2 can extend parallel to a understructure longitudinal axis tt and can be terminated proximally with respect to a respective one of first and second radiused segments 473-1, 473-2 of the outer understructure 472. In some embodiments, connective arms 474-1, 474-2, . . . 474-6 can extend from the first and second arms of the inner understructure 471-1, 472-2 transversely to and away from the understructure longitudinal axis tt towards the outer understructure 472. The connective arms 474-1, 474-2, . . . 474-6 can be connected with the inner understructure 471-1, 471-2 and the outer understructure 472.

Figure 19A:
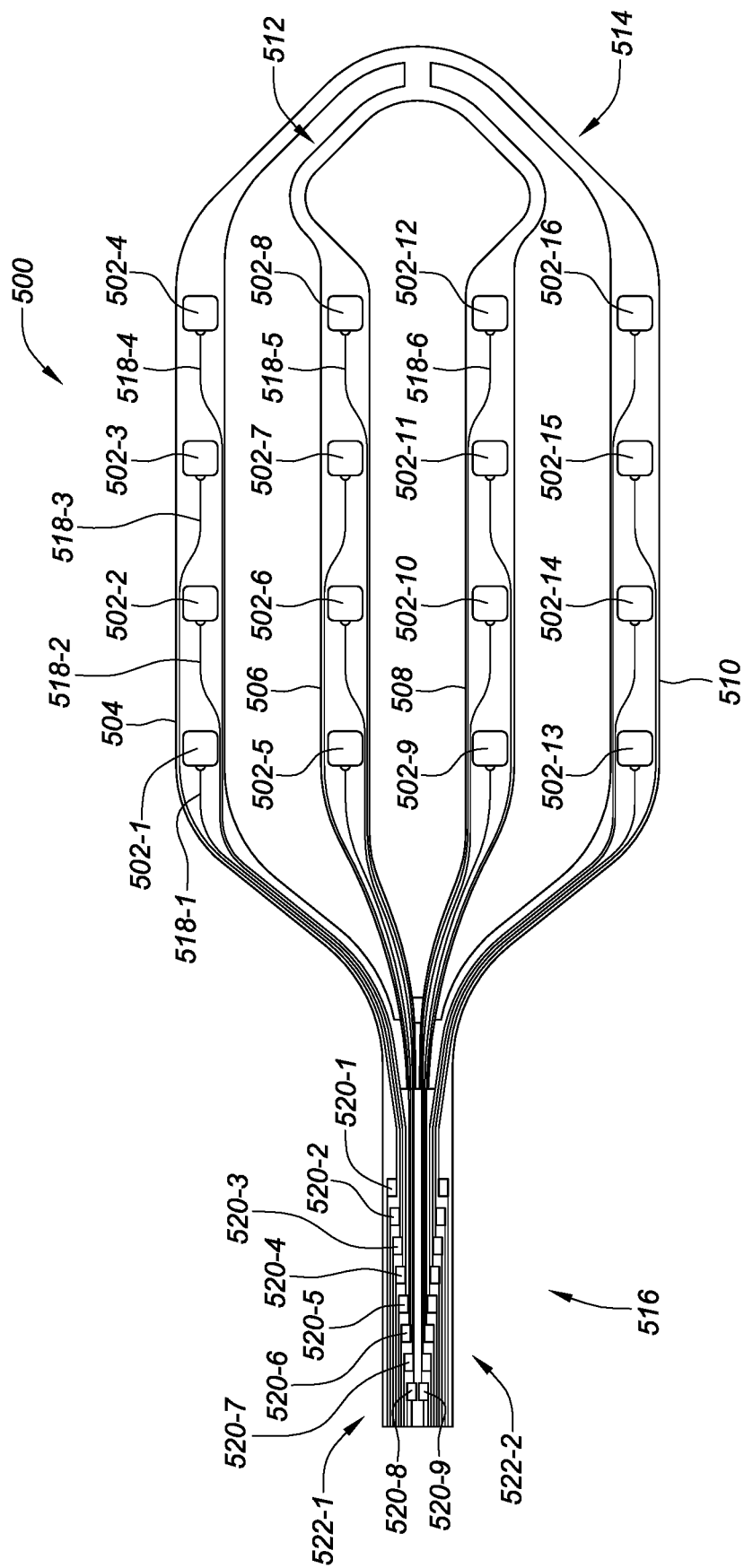
FIG. 19A depicts a top view of a flexible tip portion of a high density electrode mapping catheter that includes a plurality of electrodes, according to various embodiments of the present disclosure.

FIG. 19A depicts a top view of a flexible tip portion 500 of a high density electrode mapping catheter that includes a plurality of microelectrodes 502-1, 502-2, . . . , 502-16, according to various embodiments of the present disclosure. Hereinafter the plurality of microelectrodes 502-1, 502-2, . . . , 502-16 are referred to in the plural as microelectrodes 502 (also referred to herein as electrodes). In some embodiments, the flexible tip portion 500 forms a flexible array of microelectrodes 502, which can be disposed at a distal end of a catheter shaft. This planar array (or 'paddle' configuration) of microelectrodes 502 comprises four side-by-side, longitudinally-extending arms 504, 506, 508, 510, which can form a flexible framework on which the microelectrodes 502 are disposed. The four microelectrode-carrier arms comprise a first outboard arm 504, a second outboard arm 510, a first inboard arm 506, and a second inboard arm 508. These arms can be laterally separated from each other. The inboard portion of the flexible tip 500 can include a flared head portion 512 and the outboard portion of the flexible tip 500 can include a head portion 514. The first outboard arm 504 and the second outboard arm 510 can be part of an outboard understructure and the first inboard arm 506 and the second inboard arm 508 can be part of an inboard understructure, as previously discussed. The first and second inboard arms 506, 508, as well as the flared head portion 512, can form the inboard arm understructure that comprises an element that includes a planar cross-section and the first and second outboard arms 504, 510, as well as the head portion 514, can form the outboard arm understructure that comprises an element that includes a planar cross-section. In some embodiments, the flexible tip portion 500 can be formed from a flexible metal, such as nitinol. In some embodiments, the flexible tip portion 500 can be formed from a flexible printed circuit board. In some embodiments, the flexible tip portion 500 can include a mounting portion 516. In an example, the first and second outboard arms 504, 510 and the first and second inboard arms 506, 508 can be connected to the mounting portion 516. In some embodiments, the mounting portion 516, the first and second outboard arms 504, 510, the first and second inboard arms 506, 508, the flared head portion 512, and the head portion 514 can all be formed from a unitary piece of material. The mounting portion 516 can be inserted into a distal end of a catheter shaft, in some embodiments.

In some embodiments, the flexible tip portion 500 can include a plurality of electrically conductive traces 518-1, 518-2, 518-3, 518-4 disposed along the mounting portion 516, the first and second outboard arms 504, 510, the first and second inboard arms 506, 508, the flared head portion 512, and/or the head portion 514. Hereinafter, the electrically conductive traces 518-1, 518-2, 518-3, 518-4 are referred to in the plural as electrically conductive traces 518. Each one of the electrically conductive traces 518 can be electrically coupled with one of the microelectrodes 502. For example, a first microelectrode 502-1 can be electrically coupled with a first electrically conductive trace 518-1, a second microelectrode 502-2 can be electrically coupled with a second electrically conductive trace 518-2, a third microelectrode 502-3 can be electrically coupled with a third electrically conductive trace 518-3, and/or a fourth microelectrode 502-4 can be electrically coupled with a fourth electrically conductive trace 518-4. Although more than four traces are disposed on the flexible tip portion, for clarity only the traces 518-1, 518-2, 518-3, 518-4 are discussed herein.

In some embodiments, the traces 518 and/or microelectrodes 502 can be formed as previously discussed herein. In some embodiments, the traces 518 and/or microelectrodes 502 can be formed in a manner such as that discussed in relation to FIGS. 23A to 23F. As depicted, the first trace 518-1 can extend from a proximal side of the first microelectrode 502-1. In some embodiments, each of the traces 518 can be electrically coupled with a respective one of the microelectrodes 502 through a via, as further discussed herein. As depicted, the microelectrodes 502 can be disposed along a longitudinal length of each one of the arms. In some embodiments, the traces 518 can be routed around each one of the microelectrodes 502 that the traces 518 are not electrically coupled with to avoid contacting those microelectrodes, and thus preventing a short from occurring. In an example and as depicted, the second electrically conductive trace 518-2 can be routed around the first microelectrode 502-1 to avoid contact with the first microelectrode 502-1. The second electrically conductive trace 518-2 can be extend along an inner side of the first microelectrode 502-1 and can be coupled with the second microelectrode 502-2. The third trace 518-3 can be routed around an outer side of the first microelectrode 502-1 and second microelectrode 502-2 and can be coupled with the third microelectrode 502-3. The fourth trace 518-4 can be routed around an inner side of the first microelectrode 502-1, second microelectrode 502-2, and third microelectrode 502-3 and can be coupled with the fourth microelectrode 502-4. In an example, a trace associated with each longitudinally alternating microelectrodes 502 can be routed around alternating sides of the preceding microelectrodes 502, as depicted. For example, the second trace 518-2 associated with the second microelectrode can be routed on an inside of the preceding first microelectrode 502-1; the third trace 518-3 associated with the third microelectrode 502-3 can be routed on an outside of the preceding first and second microelectrodes 502-1, 502-3; and the fourth trace 518-4 associated with the fourth microelectrode 502-4 can be routed on an inside of the preceding first microelectrode 502-1, second microelectrode 502-2, and third microelectrode 502-3. This can allow for a more even distribution of the traces 518 on either side of the microelectrodes 502, thus allowing for the microelectrodes 502 to be more evenly spaced in the center of each arm.

In some embodiments, each of the traces 518 can be routed proximally along each one of the arms 504, 506, 508, 510 to the mounting portion 516. In some embodiments, the mounting portion 516 can include a plurality of contact pads 520-1, 520-2, . . . , 520-9, hereinafter referred to in the plural as contact pads 520, arranged in a first row 522-1 and a second row 522-2. For clarity only contact pads 520-1, 520-2, . . . , 520-9 are discussed. In some embodiments, a proximal end of each one of the traces 518 can terminate at a respective one of the contact pads 520.

In some embodiments, each row of contact pads 522-1, 522-2 can be divergent with a longitudinal axis of the flexible tip portion 500. In an example, each row of contact pads 522-1, 522-2 can extend away from the longitudinal axis of the flexible tip portion 500 as the row of contact pads 522-1, 522-2 extends distally. Accordingly, each row of contact pads 522-1, 522-2 can extend laterally away from one another as the rows extends distally. In some embodiments, each row of contact pads 522-1, 522-2 can be linear. In an example, the mounting portion 516 can have a limited lateral width. Accordingly, the contact pads 520 can be longitudinally and laterally staggered with respect to one another. For instance, from the distal end to the proximal end of the mounting portion 516, the contact pads 520 can be longitudinally staggered toward the proximal end and laterally staggered toward the longitudinal axis of the flexible tip portion 500.

In some embodiments, the trace 518-3 can be connected to the proximal end of the contact pad 520-1. Accordingly, the contact pad 520-1 can be electrically coupled with the microelectrode 502-3. In some embodiments, a test trace can extend proximally with respect to one or more of the contact pads 520. For example, a test trace can extend proximally with respect to the contact pad 520-1. The test trace can lead to a test portion (not shown) that can include a larger contact test pad, which can be probed with a test instrument to ensure continuity between the contact pad 520-1, the electrical trace 518-3, and the microelectrode 502-3. In some embodiments, a contact test pad can be electrically coupled with each one of the contact pads 520 via a test trace. In some embodiments, the test traces can extend proximally from each one of the contact pads 520. The longitudinal and lateral staggering of the contact pads 520 allow for an electrical trace to extend distally from each one of the contact pads 520 and a test trace to extend proximally from each one of the contact pads, as depicted.

Figure 19B:
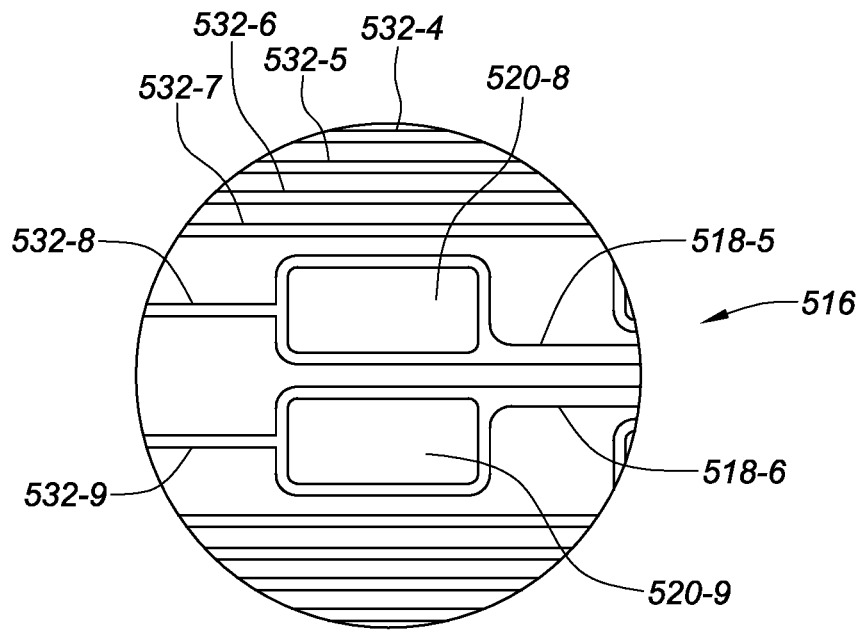
FIG. 19B depicts an enlarged top view of a pair of contact pads disposed on the flexible tip portion depicted in FIG. 19A, according to various embodiments of the present disclosure.

FIG. 19B depicts an enlarged top view of a pair of contact pads 520-8, 520-9 disposed on the flexible tip portion depicted in FIG. 19A, according to various embodiments of the present disclosure. In some embodiments, the contact pads 520 can be formed from an electrically conductive material. For example, the contact pads 520 can be formed from copper, gold, etc. In some embodiments, the contact pads 520 can have a lateral width of approximately 0.2 millimeters, although the contact pads can have a smaller or larger lateral width. In some embodiments, the contact pads 520 can have a longitudinal length of approximately 0.45 millimeters, although the contact pads can have a shorter or longer longitudinal length. As depicted, electrically conductive traces 518-5, 518-6 can extend distally from contact pads 520-8, 520-9 and can be electrically coupled with the contact pads 520-8, 520-9. For example, the electrically conductive traces 518-5, 518-6 can electrically couple the contact pad 520-8 with the microelectrode 502-8 and can electrically couple the contact pad 520-9 with the microelectrode 502-12, respectively. In some embodiments, the contact pads 520-8, 520-9 can include test traces 532-8, 532-9 that extend proximally from each one of the contact pads 520-8, 520-9, respectively, as previously discussed. As depicted, other test traces 532-4, 532-5, 532-6, 532-7, 532-8 can extend longitudinally along the mounting portion 516. In some embodiments, the test traces 532 can be laterally spaced apart from one another by approximately 0.05 millimeters, although the test traces can be spaced apart by a smaller or greater distance in some embodiments. In some embodiments, the test traces can have a lateral width of approximately 0.03 millimeters, although the test traces can have a lateral width that is greater than or less than 0.03 millimeters.

Figure 19C:
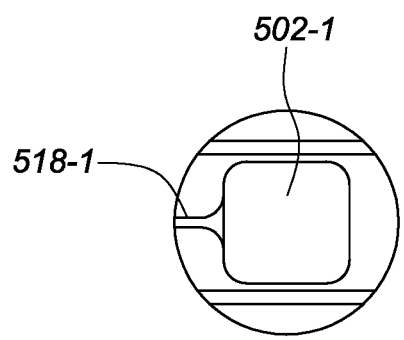
FIG. 19C depicts an enlarged top view of a microelectrode disposed on the flexible tip portion depicted in FIG. 19A, according to various embodiments of the present disclosure.

FIG. 19C depicts an enlarged top view of a microelectrode 502-1 disposed on the flexible tip portion 500 depicted in FIG. 19A, according to various embodiments of the present disclosure. In some embodiments, the microelectrode 502-1 can have an electrically conductive trace 518-1 that extends proximally from the microelectrode 502-1. In some embodiments, the microelectrode 502-1 can have a longitudinal length in a range from 0.1 to 5 millimeters and can have a lateral width in a range from 0.1 to 5 millimeters. However, in some embodiments, the microelectrode 502-1 can have a longitudinal length of approximately 0.92 millimeters and can have a lateral width of approximately 0.9 millimeters. However, in some embodiments, the microelectrode 502-1 can have a longitudinal length of approximately 0.92 millimeters and a lateral width of approximately 0.3 millimeters. As depicted, electrically conductive traces can extend on either side of the microelectrode 502-1, connecting other microelectrodes 502 with a respective one of the contact pads 520.

FIG. 19D depicts a side view of microelectrodes disposed on a top and bottom of the flexible tip portion 500 depicted in FIG. 19A, according to various embodiments of the present disclosure. FIG. 19A depicts a top of the flexible tip portion 500 with microelectrodes 502 disposed on the first outboard arm 504. In some embodiments, a bottom of the flexible tip portion 500 can include the same features as those of the top of the flexible tip portion 500. For example, as depicted in FIG. 19D, a bottom of the flexible tip portion 500 can also include microelectrodes 502-17, 502-18, 502-19, 502-20, hereinafter referred to in the plural as microelectrodes 502, electrically conductive traces 518 (not shown), contact pads 520 (not shown), etc. In an example, this can enable investigation of different unipolar and bipolar electrogram configurations. In an example, where the electrodes disposed on the top of the flexible tip portion 500 are disposed against tissue and the electrodes of the bottom of the flexible tip portion 500 are disposed in a blood pool, or vice versa, a different electrical signal can be received by the top electrodes than the bottom electrodes. In some embodiments, the signal (e.g., impedance) received from the top electrodes can be analyzed with respect to the signal (e.g., impedance) received from the bottom electrodes to determine whether the flexible tip portion 500 is in contact with tissue. In some embodiments, a degree of contact between the flexible tip portion 500 and associated microelectrodes 502 and tissue can be determined based on the analysis of the signals received from the bottom electrodes and the top electrodes. In an example, where the signals from both bottom electrodes and the top electrodes are the same, this can be an indication that the entire flexible tip portion 500 is disposed in a blood pool and is not in contact with tissue.

In an example, using this 'bottom minus top' bipolar configuration can result in electrograms that are distinctly different in morphology compared to bipolar electrograms that use a 'bottom minus adjacent bottom' bipolar configuration. For example, some medical devices that are used to produce electrograms receive electrical signals from electrodes that are adjacent to one another and located on a same side of the medical device. Electrograms produced with devices of the present disclosure, for example, those that include electrodes on both sides (e.g., top and bottom) of the device (e.g., flexible tip portion 500), can produce distinctly different electrograms.

As depicted in FIG. 19D, the microelectrodes 502 can be disposed on the top and/or bottom of the flexible tip portion 500. For example, the microelectrodes 502 can be disposed on a top and/or bottom of the first outboard arm 504, the second outboard arm 510 (FIG. 19A), the first inboard arm 506 (FIG. 19A), and/or the second inboard arm 508 (FIG. 19A). Each of the top microelectrodes 502 can have a vertically adjacent bottom microelectrode 502. In an example, a first top microelectrode 502-1 can be vertically adjacent to a bottom electrode 502-17 that is located directly beneath the first top microelectrode 502-1. In some embodiments, a vertical spacing (Vs) between an outer surface of each of the microelectrodes 502 on the top and bottom of the flexible tip portion 500 can be in a range from 0 to 3 millimeters. In some embodiments, the vertical spacing (Vs) between an outer surface of each of the microelectrodes 502 on the top and bottom of the flexible tip portion 500 can approximately 0.22 millimeters. The vertical spacing Vs between the microelectrodes 502 disposed on the top and those disposed on the bottom can provide a third dimension between the microelectrodes 502, enabling the microelectrodes 502 disposed on the top and bottom of the flexible tip portion 500 to receive extracellular matrix (ECM) signals.

Some medical devices can include electrodes that are disposed along a single line, providing one-dimensional spacing, or along a plane (e.g., that are laterally adjacent to one another), providing two-dimensional spacing. However, embodiments of the present disclosure can provide microelectrodes 502 that are laterally adjacent to one another and also vertically adjacent to one another and can be configured to receive ECM signals with both the bottom electrodes and top electrodes that are vertically adjacent to one another. In some embodiments of the present disclosure, the vertical spacing Vs between the microelectrodes 502 can provide a greater resolution of extracellular matrix (ECM) signals. In addition, clean bi-pole signals can be generated between the microelectrodes 502 disposed on the top of the flexible tip portion 500 and the microelectrodes 502 disposed on the bottom of the flexible tip portion 500.

As previously discussed, a determination of whether any of the microelectrodes on the flexible tip portion 500 are in contact with tissue can be made based on a difference in a bottom signal that is received by a microelectrode 502 disposed on the bottom of the flexible tip portion 500 and a top signal that is received by a microelectrode 502 disposed on the top of the flexible tip portion 500. For example, if the bottom microelectrode 502 is in contact with tissue and the top microelectrode 502 is disposed in a blood pool, the bottom signal will be different than the top signal. If both the bottom and top microelectrodes 502 are disposed in the blood pool, the bottom signal and the top signal can be the same in some embodiments. This determination can be made by an electronic control that is in communication with each one of the microelectrodes, such as that discussed in relation to FIG. 31.

As further depicted in FIG. 19D, the microelectrodes 502 can extend vertically from a surface of the understructure (e.g., first outboard arm 504). In some embodiments, microelectrodes 502 can have a thickness in a range from 0.1 to 1000 microns. In some embodiments, the microelectrodes 502 can have a thickness of 0.5 microns. By raising the microelectrodes 502 off of a surface of the understructure, the microelectrodes 502 can more easily contact tissue.

FIG. 20 depicts an isometric side, top, and distal end view of the flexible tip portion 500 depicted in FIG. 19A, according to various embodiments of the present disclosure. The flexible tip portion 500 includes those features as discussed in relation to FIGS. 19A to 19C. In an example, the flexible tip portion 500 includes the longitudinally-extending arms 504, 506, 508, 510, flared head portion 512, head portion 514, and mounting portion 516. As depicted, the different elements (e.g., longitudinally-extending arms 504, 506, 508, 510, flared head portion 512, head portion 514, and mounting portion 516) that form the flexible tip portion 500 can include planar cross-sections. For example, a thickness of each element can be less than a lateral width of each element. Accordingly, a top surface of the flexible tip portion 500 and a bottom surface of the flexible tip portion 500 can be flat, which can prove to be beneficial when forming the microelectrodes 502, the electrically conductive traces 518, and/or the contact pads 520 on the flexible tip portion 500. As discussed herein, an understructure of the flexible tip portion 500 can be formed from a flexible metal, such as nitinol, and/or a flexible printed circuit board, upon which the microelectrodes 502, the electrically conductive traces 518, and/or the contact pads 520 can be disposed.

Figure 21:
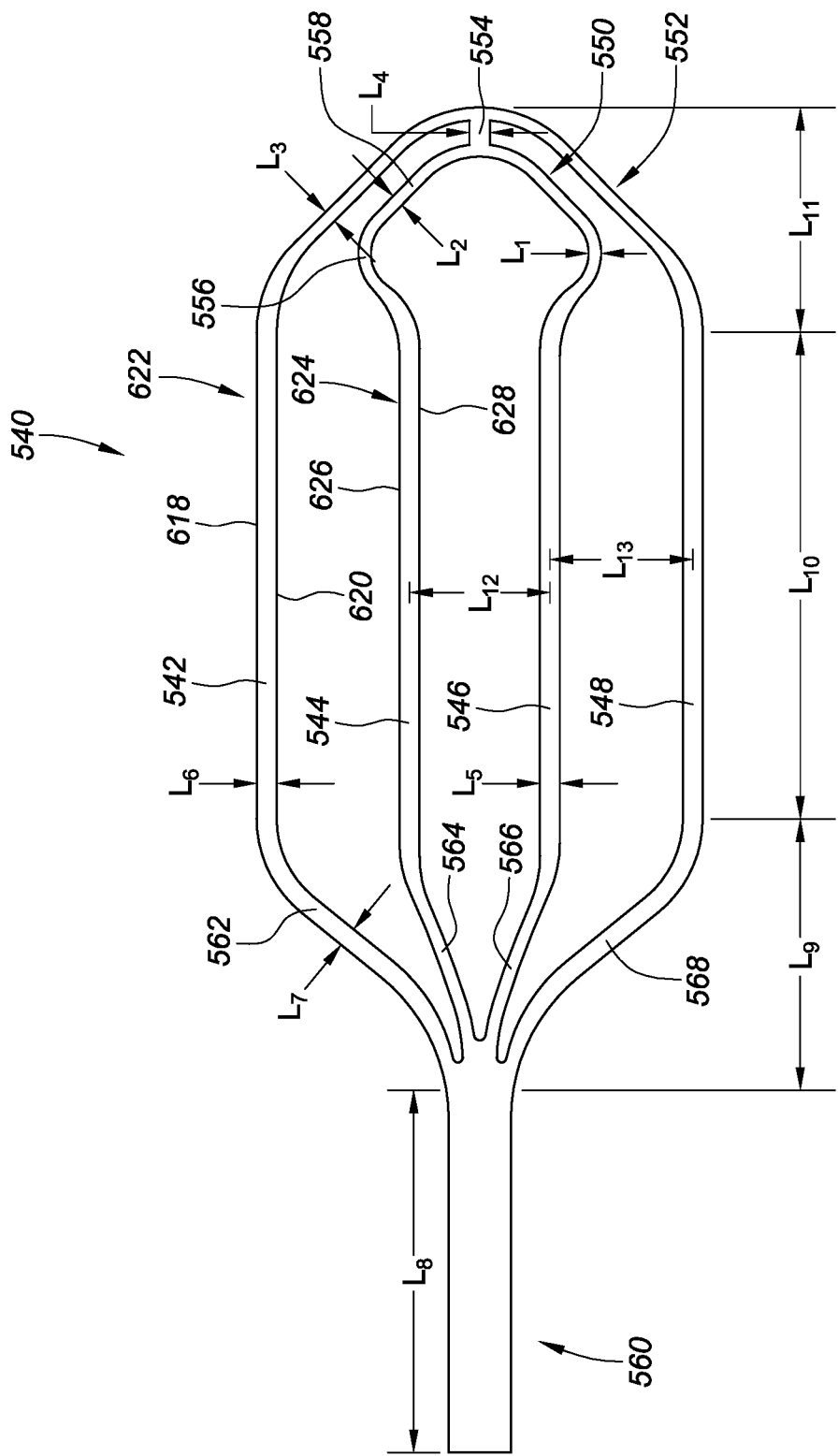
FIG. 21 depicts a top view of an understructure of a flexible tip portion of a high density electrode mapping catheter, according to various embodiments of the present disclosure.

FIG. 21 depicts a top view of an understructure of a flexible tip portion 540 of a high density electrode mapping catheter, according to various embodiments of the present disclosure. In some embodiments, the flexible tip portion 540 can include four microelectrode-carrier arms that comprise a first outboard arm 542, a second outboard arm 548, a first inboard arm 544, and a second inboard arm 546. These arms can be laterally separated from each other. The inboard portion of the flexible tip 540 can include a flared head portion 550 and the outboard portion of the flexible tip 540 can include a head portion 552, which are connected via a connective portion 554. In some embodiments, the flared head portion 550 can include a lateral apex portion 556. In some embodiments, a lateral width $L_1$ of the lateral apex portion 556 can be in a range from 0.08 to 0.32 millimeters. In an example, the lateral width $L_1$ of the apex portion 556 can be approximately 0.16 millimeters. The flared head portion 550 can additionally include a tapered head arm 558 that can have a width $L_2$ in a range from 0.10 to 0.45 millimeters. In an example, the width $L_2$ of the tapered head arm 558 can be approximately 0.21 millimeters. In some embodiments, the arms that form the head portion 552 can have a width $L_3$ in a range from −0.1 to 0.45 millimeters. In an example, the width $L_3$ of the arms that form the head portion 552 can have a width of approximately 0.21 millimeters. The connective portion 554 can have a lateral width $L_4$ in a range from 0.08 to 0.32 millimeters. In some embodiments, the connective portion 554 can have a lateral width $L_4$ of approximately 0.16 millimeters.

The first outboard arm 542 and the second outboard arm 548 can include an outboard understructure and the first inboard arm 544 and the second inboard arm 546 can include an inboard understructure, as previously discussed. In some embodiments, a lateral width $L_5$ of the first and second inboard arms 544, 546 can be in a range from 0.10 to 1.0 millimeters. In some embodiments, the lateral width $L_5$ of the first and second inboard arms 544, 546 can be approximately 0.51 millimeters. In some embodiments, a lateral width $L_6$ of the first and second outboard arms 542, 548 can be in a range from 0.10 to 1.0 millimeters. In some embodiments, the lateral width $L_6$ of the first and second outboard arms 542, 548 can be approximately 0.51 millimeters.

In some embodiments, a first outboard transition arm 562 can connect the first outboard arm 542 to the mounting portion 560; a first inboard transition arm 564 can connect the first inboard arm 544 to the mounting portion 560; a second inboard transition arm 566 can connect the second inboard transition arm 546 to the mounting portion; and a second outboard transition arm 568 can connect the second outboard arm 548 to the mounting arm 560. In some embodiments, the width $L_7$ of the first and second outboard transition arms 562, 568 can be in a range from 0.10 to 1.0 millimeters. In some embodiments, the width $L_7$ of the first and second outboard transition arms 562, 568 can be approximately 0.51 millimeters.

In some embodiments, the flexible tip portion 540 can include a mounting portion 560, as previously discussed. In some embodiments, a longitudinal length Lg of the mounting portion 560 can be in a range from 5 to 20 millimeters. In some embodiments, the longitudinal length Lg of the mounting portion 560 can approximately 11.1 millimeters. In some embodiments, a longitudinal length L9 of the inboard and outboard transition arms can be in a range from 3 to 20 millimeters. In some embodiments, the longitudinal length L9 of the portion of the flexible tip that includes the transition arms can be 9.1 millimeters. In some embodiments, a longitudinal length $L_{10}$ of the inboard and outboard arms can be in a range from 8 to 50 millimeters. In some embodiments, the longitudinal length $L_{10}$ of the inboard and outboard arms can be 13.9 millimeters. In some embodiments, a longitudinal length $L_{11}$ of the flared head portion 550 and the head portion 552 can be in a range from 3 to 20 millimeters. In some embodiments, the longitudinal length $L_{11}$ of the flared head portion 550 and the head portion 552 can be 9.8 millimeters.

In some embodiments, a lateral spacing $L_{12}$ between the first inboard arm 544 and the second inboard arm 546 can be in a range from 0.10 to 4 millimeters. In some embodiments, the lateral spacing $L_{12}$ between the first inboard arm 544 and the second inboard arm 546 can be approximately 4 millimeters. In some embodiments, a lateral spacing $L_{13}$ between the first inboard arm 544 and the first outboard arm 542 and between the second inboard arm 546 and the second outboard arm 548 can be in a range from 0.10 to 4 millimeters. In some embodiments, the lateral spacing $L_{13}$ between can be approximately 4 millimeters.

Figure 22:
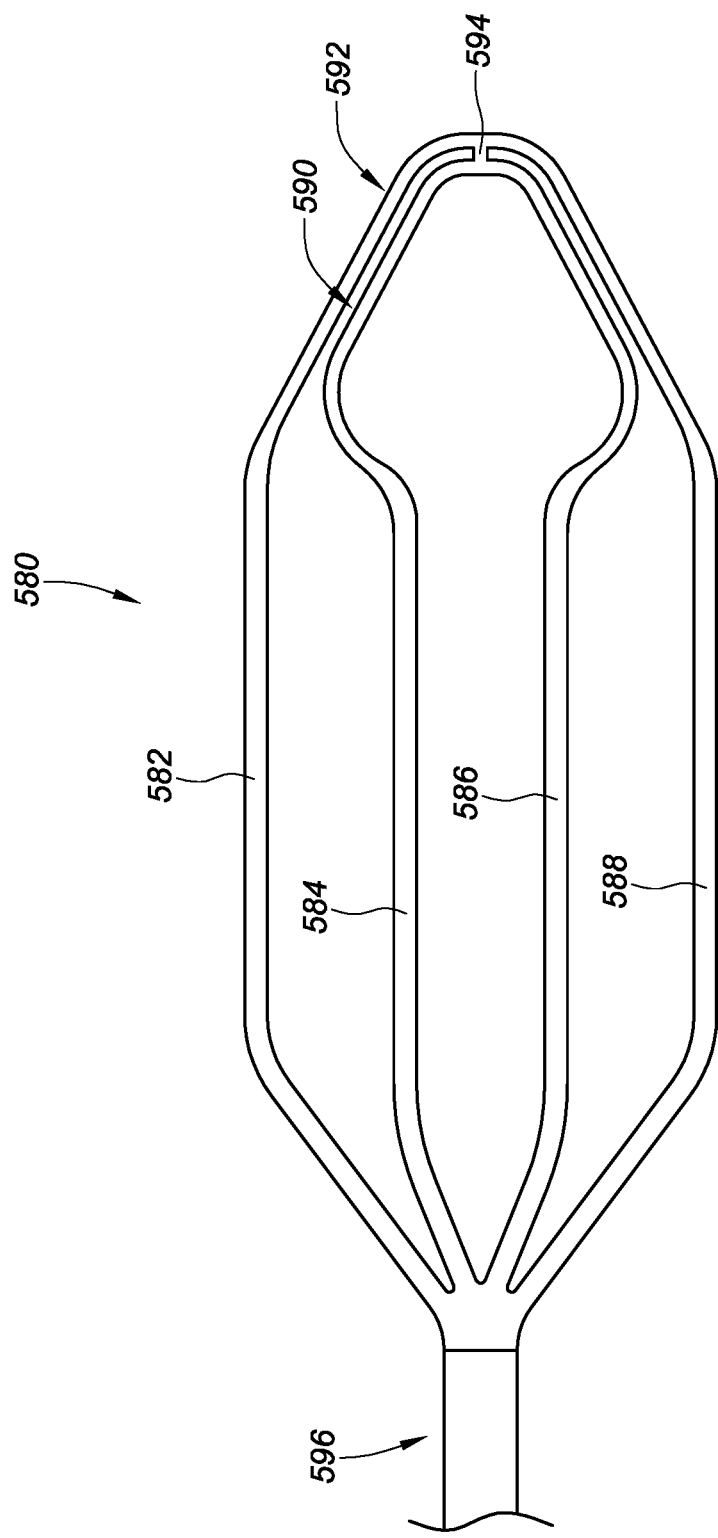
FIG. 22 depicts a top view of an alternate embodiment of an understructure of a high density electrode mapping catheter, according to various embodiments of the present disclosure.

FIG. 22 depicts a top view of an alternate embodiment of an understructure of a flexible tip portion 580 of a high density electrode mapping catheter, according to various embodiments of the present disclosure. In some embodiments, the flexible tip portion 580 can include four microelectrode-carrier arms that comprise a first outboard arm 582, a second outboard arm 588, a first inboard arm 584, and a second inboard arm 586, which can be mounted to a mounting portion 596. The mounting portion 596, the inboard and outboard arms 582, 584, 586, 588, the flared head portion 590, and head portion 592 can be formed from a single piece of material. The inboard portion of the flexible tip 580 can include a flared head portion 590 and the outboard portion of the flexible tip 580 can include a head portion 592, which are connected via a connective portion 594. In some embodiments, the flared head portion 590 and the head portion 592 can have a greater longitudinal length that those depicted in FIG. 21. In some embodiments, the elements that form the flared head portion 590 and the head portion 592 can have a width that is less than that depicted in relation to FIG. 21. In an example, by decreasing a width of the flared head portion 590 or the head portion 592, or other parts of the flexible tip 580, a force which is required to deflect the flared head portion 590, head portion 592 or other parts of the flexible tip 580 can be decreased. Accordingly, the various portions of the flexible tip 580 can be made more atraumatic. For example, the portions of the flexible tip 580 can more readily deflect when they contact tissue as a result of the reduced deflection force.

FIGS. 23A-23F depict an isometric top and side view of an arm of an understructure of a high density electrode mapping catheter and associated processing steps, according to various embodiments of the present disclosure. As depicted in FIG. 23A, the understructure 610 can be formed from a flexible material in some embodiments. In an example, the flexible material can include nitinol and can be approximately 160 microns thick, however the flexible material can be greater or less than 160 microns thick. In some embodiments, the understructure 610 can be coated with a top dielectric layer 612-1 and/or bottom dielectric layer 612-2, as depicted in FIG. 23B. In an example, the dielectric material can include, for example, a parylene, a polyimide, an epoxy, etc., as previously discussed herein. However, the dielectric material can include other types of dielectrics. In some embodiments, the dielectric layer 612-1, 612-2 can be in a range from 1.0 to 30 microns thick. In an example, the dielectric layer 612-1, 612-2 can be approximately 10 microns thick, however, the dielectric material can be greater than or less than 10 microns thick. In some embodiments, the dielectric material can electrically insulate the understructure from conductive traces that are formed on top of the dielectric layers. In some embodiments, a tie layer can be disposed between the dielectric material and the flexible material. In an example, the tie layer can be sputtered chrome with a thickness of approximately 1000 angstroms, although the thickness of the sputtered chrome can be greater than or less than 1000 angstroms thick.

In some embodiments, the dielectric layers 612-1, 612-2 can extend laterally outward with respect to the understructure 610 to form an atraumatic inboard and/or outboard edge. In an example, the understructure 610 can have a planar cross-section, as previously discussed herein, having a thickness that is less than a width of the understructure 610. In some embodiments, a lateral edge of the understructure 610 can be sharp, due to a relatively thin thickness of the understructure 610. To provide an atraumatic lateral edge (e.g., outboard and/or inboard edge) of the understructure 610, the dielectric layers 612-1, 612-2 can extend laterally outward with respect to the understructure 610, as depicted in FIG. 23C. The atraumatic edge can act as a protector/bumper to prevent the understructure 610 from contacting other materials (e.g., inner diameter of an introducer sheath, tissues in the heart, etc.).

FIG. 23C is a cross-sectional view of the coated understructure 610 depicted in FIG. 23B, along the line 23C-23C. For example, the first and second dielectric layers 612-1, 612-2 can include a first and second outboard overhang 614-1, 614-2 and the first and second dielectric layers 612-1, 612-2 can include a first and second inboard overhang 616-1, 616-2, as depicted in FIG. 23C. In some embodiments, the first and second outboard overhang 614-1, 614-2 and/or the first and second inboard overhang 616-1, 616-2 can be formed on each portion of a flexible tip portion of a high density electrode mapping catheter, such as that discussed in relation to FIGS. 19A to 22. For example, with respect to the flexible tip portion 540 depicted and discussed in relation to FIG. 21, an outboard understructure 622 that includes the first outboard transition arm 562, the first outboard arm 542, the head portion 552, the second outboard arm 548, and the second outboard transition arm 568 can have a first and second outboard overhang 614-1, 614-2 disposed along an outboard edge 618 that extends along a perimeter of the outboard understructure 622 (FIG. 21). In some embodiments, the first and second outboard overhang 614-1, 614-2 can be disposed along the outboard edge 618 of one or more of the first outboard transition arm 562, the first outboard arm 542, the head portion 552, the second outboard arm 548, and/or the second outboard transition arm 568. In some embodiments, the outboard understructure 622 can have a first and second inboard overhang 616-1, 616-2 disposed along an inboard edge 620 of the outboard understructure 622. In some embodiments, the first and second inboard overhang 616-1, 616-2 can be disposed along the inboard edge 620 of one or more of the first outboard transition arm 562, the first outboard arm 542, the head portion 552, the second outboard arm 548, and/or the second outboard transition arm 568.

With further reference to FIG. 21, in some embodiments, an inboard understructure 624 that includes the first inboard transition arm 564, the first inboard arm 544, the flared head portion 550, the second inboard arm 546, and the second inboard transition arm 566 can have a first and second outboard overhang 614-1, 614-2 disposed along an outboard edge 626 that extends along a perimeter of the inboard understructure 624 (FIG. 21). In some embodiments, the first and second outboard overhang 614-1, 614-2 can be disposed along the outboard edge 624 of one or more of the first inboard transition arm 564, the first inboard arm 626, the flared head portion 550, the second inboard arm 546, and/or the second inboard transition arm 566. In some embodiments, the inboard understructure 624 can have a first and second inboard overhang 616-1, 616-2 disposed along an inboard edge 628 of the inboard understructure 624. In some embodiments, the first and second inboard overhang 616-1, 616-2 can be disposed along the inboard edge 628 of one or more of the first inboard transition arm 564, the first inboard arm 544, the flared head portion 550, the second inboard arm 546, and/or the second inboard transition arm 566.

As depicted in FIG. 23D, one or more electrically conductive traces 636-1, 636-2 and/or electrically conductive pads 638 can be formed on an outer surface of the dielectric material 612-1, 612-2. In some embodiments, one or more electrically conductive traces 636-1, 636-2 and/or electrically conductive pads 638 can be formed on the outer surface of the first dielectric layer 612-1 and/or the outer surface of the second dielectric layer 612-2. In some embodiments, the electrically conductive traces 636-1, 636-2 and/or the electrically conductive pads 638 can be formed from an electrically conductive material, such as copper. The copper can have a thickness of approximately 7 microns, although the thickness of the copper can be greater or less than 7 microns. In some embodiments, a tie layer can be included between the electrically conductive traces 636-1, 636-2 and the dielectric material 612-1, 612-2. In an example, the tie layer can be sputtered chrome with a thickness of approximately 130 angstroms. However, the thickness of the tie layer can be greater than or less than 130 angstroms.

As depicted in FIG. 23E, the first dielectric layer 612-1 has been coated with a first overcoat dielectric layer 640-1 and the second dielectric layer 612-2 has been coated with a second overcoat dielectric layer 640-2. In some embodiments, the overcoat dielectric layers 640-1, 640-2 can protect the one or more electrically conductive traces 636-1, 636-2 and/or the one or more electrically conductive pads 638 and/or prevent the one or more electrically conductive traces 636-1, 636-2 and/or the one or more electrically conductive pads 638 from contacting tissue. In some embodiments, an exposed area 642 can be created in the overcoat dielectric layer 640-1 and the overcoat dielectric layer 640-2 (although not shown). In an example, the exposed area 642 can be a via that extends through the overcoat dielectric layer 640-1, such that the electrically conductive pad 638 can be accessed. In some embodiments, the overcoat dielectric layers 640-1, 640-2 can have a thickness of approximately 10 microns, although the thickness of the overcoat layers can be greater than or less than 10 microns. As depicted in FIG. 23F, an electrode 644 can be disposed on an outer surface of the overcoat dielectric layer 640-1. In an example, the electrode 644 can be formed from an electrically conductive material, such as gold. The gold can be approximately 0.5 microns thick, although the thickness of the gold can be greater than or less than 0.5 microns thick. In some embodiments, a tie layer can be disposed between the conductive pad 638 and the electrode 644. In an example, the tie layer can include nickel. In some embodiments, the nickel can have a thickness of approximately 0.4 microns, although the thickness of the nickel can be greater than or less than 0.4 microns.

Figure 24A:
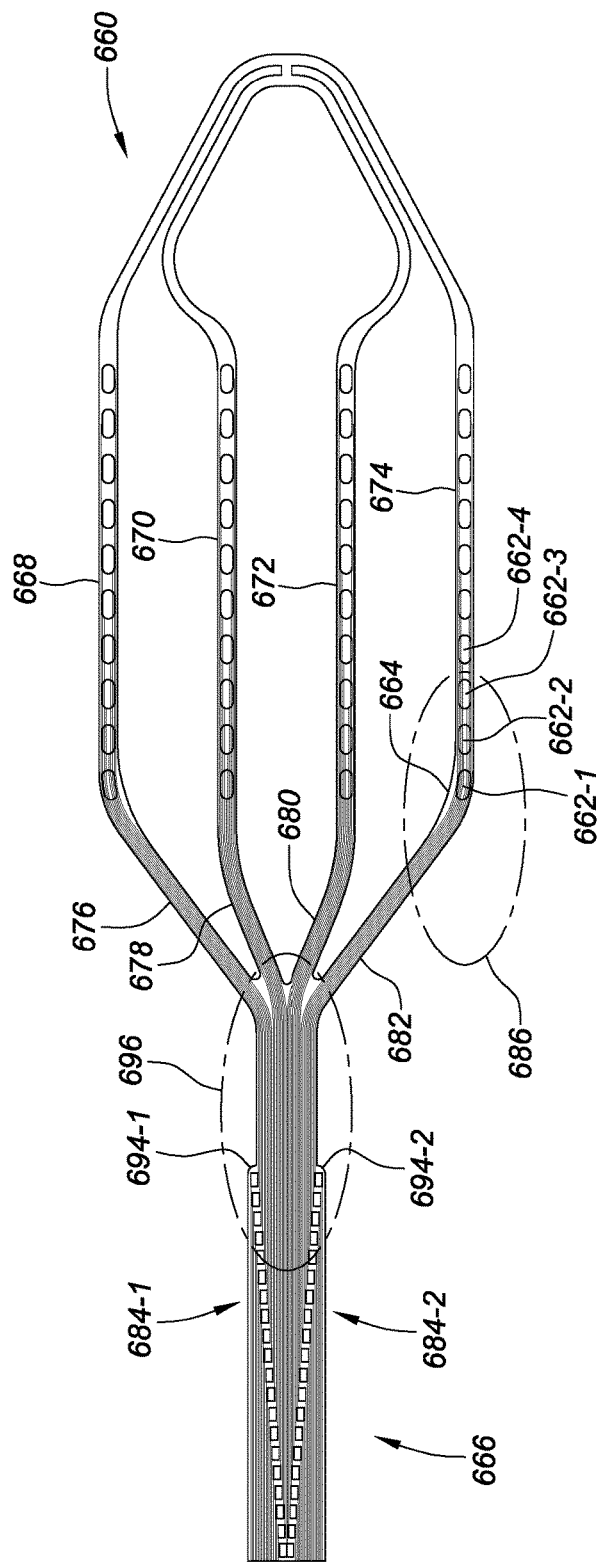
FIG. 24A depicts a top view of an understructure of a flexible tip portion 660 of a high density electrode mapping catheter that includes a plurality of electrodes, traces, and a contact pad, according to various embodiments of the present disclosure.

FIG. 24A depicts a top view of an understructure of a flexible tip portion 660 of a high density electrode mapping catheter that includes a plurality of electrodes 662-1, 662-2, 662-3, 662-4, hereinafter referred to in the plural as electrodes 662, traces 664, and a mounting portion 666, according to various embodiments of the present disclosure. As discussed herein, the flexible tip portion 660 can include a first outboard arm 668, a first inboard arm 670, a second inboard arm 672, and a second outboard arm 674. In some embodiments, the flexible tip portion 660 can include a first outboard transition arm 676, a first inboard transition arm 678, a second inboard transition arm 680, and a second outboard transition arm 682. A proximal end of the transition arms can be connected to the mounting portion, which includes a contact pad 684. As discussed in relation to FIGS. 8A to 8C, electrically conductive traces 664 can be connected to each one of the electrodes disposed on the understructure of the flexible tip portion 660. The electrically conductive traces 664 can extend proximally from each one of the electrodes 662 down each of the outboard arms 668, 674, inboard arms 670, 672, outboard transition arms 676, 682, and inboard transition arms 678, 680, to the mounting portion 666. In some embodiments, the electrically conductive traces 664 can terminate at a first or second row of contact pads 684-1, 684-2, as previously discussed in relation to FIG. 19A. In some embodiments, test traces can extend proximally from each one of the contact pads in the first and second row of contact pads 684-1, 684-2. As generally depicted in FIG. 24A, a density of electrically conductive traces 664 covering the understructure of the flexible tip portion 660 increases in the proximal direction. For example, as depicted, a proximal portion of the outboard mounting arms 668, 674 and inboard mounting arms 678, 680; each one of the outboard transition arms 676, 682 and the inboard transition arms 678, 680; and the mounting portion 666 can include electrically conductive traces 664 that cover a majority of their surfaces, as depicted.

Figure 24B:
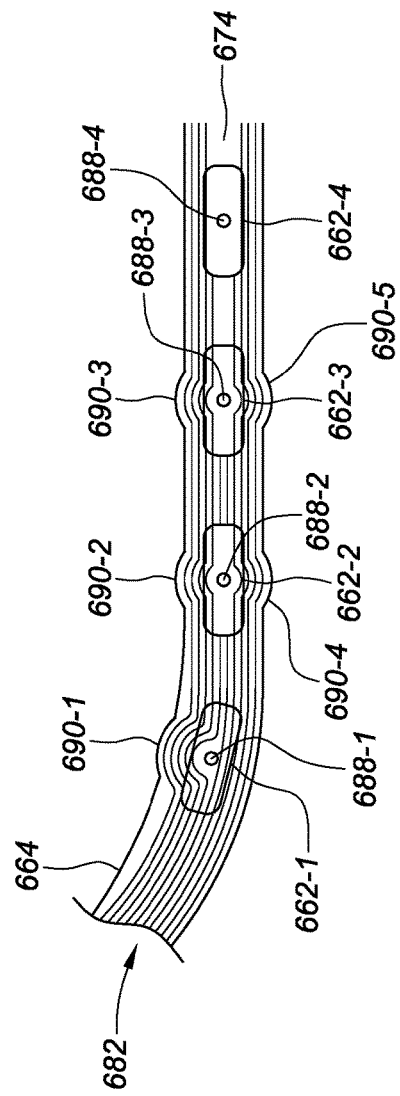
FIG. 24B depicts an enlarged top view of a portion of a second outboard arm of the flexible tip portion depicted in FIG. 24A, according to various embodiments of the present disclosure.

As depicted in FIG. 24B, the junction between the proximal end of the second outboard arm 674 and the second outboard transition arm 682 can include a plurality of electrically conductive traces 664 that cover a majority of the second outboard arm 674 and the second outboard transition arm 682. In some embodiments, the traces can extend beneath each one of the plurality of electrodes 662, as previously discussed herein, for example, in relation to FIG. 4D. In some embodiments, vias 688-1, 688-2, 688-3, 688-4, hereinafter referred to in the plural as vias 688, can be formed in a dielectric coating that covers the understructure of the flexible tip portion 660 and can provide an electrical connection between each one of the electrically conductive traces 664 and each one of the electrodes 662. In some embodiments, each one of the electrically conductive traces 664 can be routed around each one of the vias 688. In an example, each one of the electrically conductive traces 664 can have a routing bend 690-1, 690-2, 690-3, 690-4, 690-4, 690-5, hereinafter referred to in the plural as routing bends 690, in a portion of the electrically conductive trace 664 that is adjacent to each one of the vias 688. In an example, the routing bends 690 can be formed towards a proximal end of the outboard and inboard arms, where a density of the electrically conductive traces 664 is increased. For instance, in order to route the electrically conductive traces 664 around the vias 688, the traces 664 can be routed outward or inwardly with respect to a longitudinal axis of the flexible tip portion 660 around the vias 688. As depicted in FIG. 24B, routing bends 690-1, 690-2, 690-3 can be included in the trace 664. The routing bends 690-1, 690-2, 690-3 can become larger (e.g., extend further outward or inward), in some embodiments, as the trace 664 extends proximally along the understructure (e.g., second outboard arm 674).

Figure 24C:
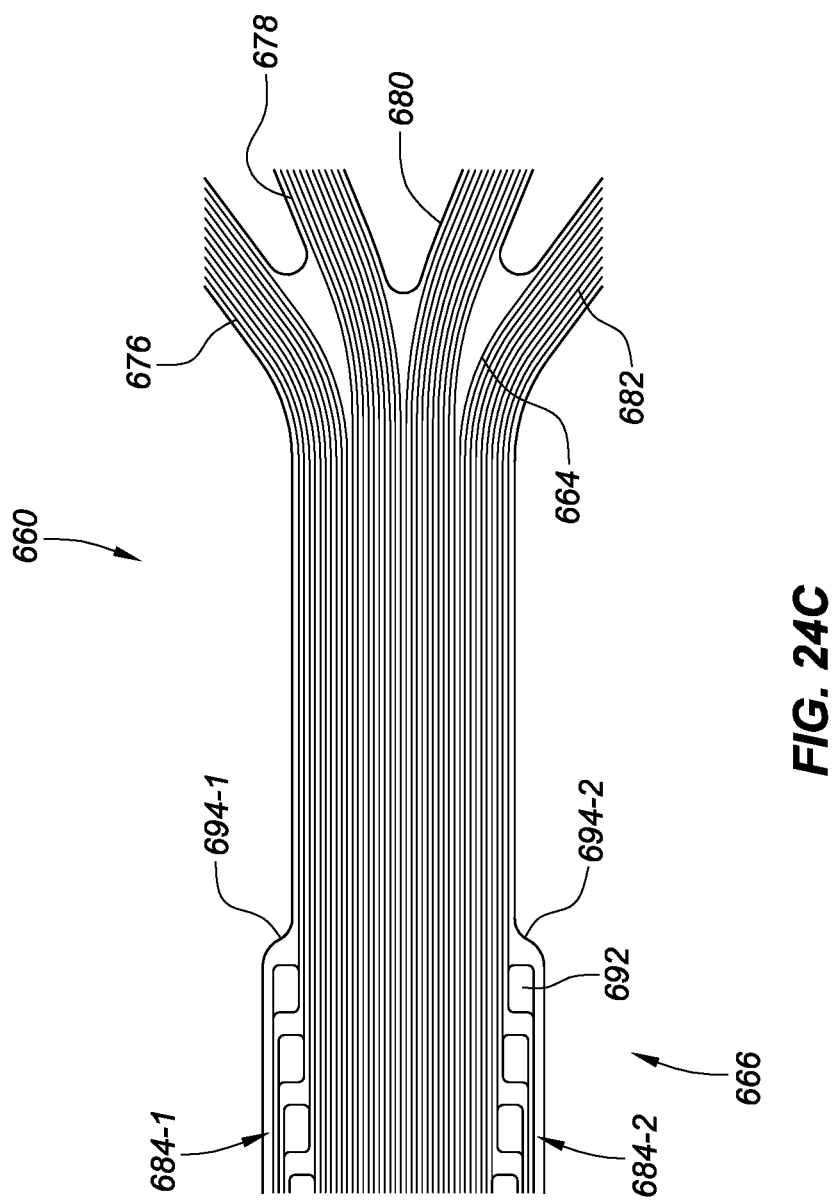
FIG. 24C depicts an enlarged top view of a portion of the flexible tip portion that includes a contact pad depicted in FIG. 24A, according to various embodiments of the present disclosure.

FIG. 24C depicts an enlarged top view of a portion 696 of the flexible tip portion 660 that includes first and second rows of contact pads 684-1, 684-2 depicted in FIG. 24A, according to various embodiments of the present disclosure. As depicted, the plurality of traces 664 can extend along the outboard and inboard transition arms 676, 682, 678, 680 and the mounting portion 666 to contact pads (e.g., contact pad 692). In some embodiments, the mounting portion 666 can include flared contact pad portions 694-1, 694-2. In an example, the flared contact pad portions 694-1, 694-2 can extend laterally from either side of the mounting portion 666 and can provide an area that includes an increased lateral width, which can provide increased space for mounting the first and second rows of contact pads 684-1, 684-2.

Figure 25A:
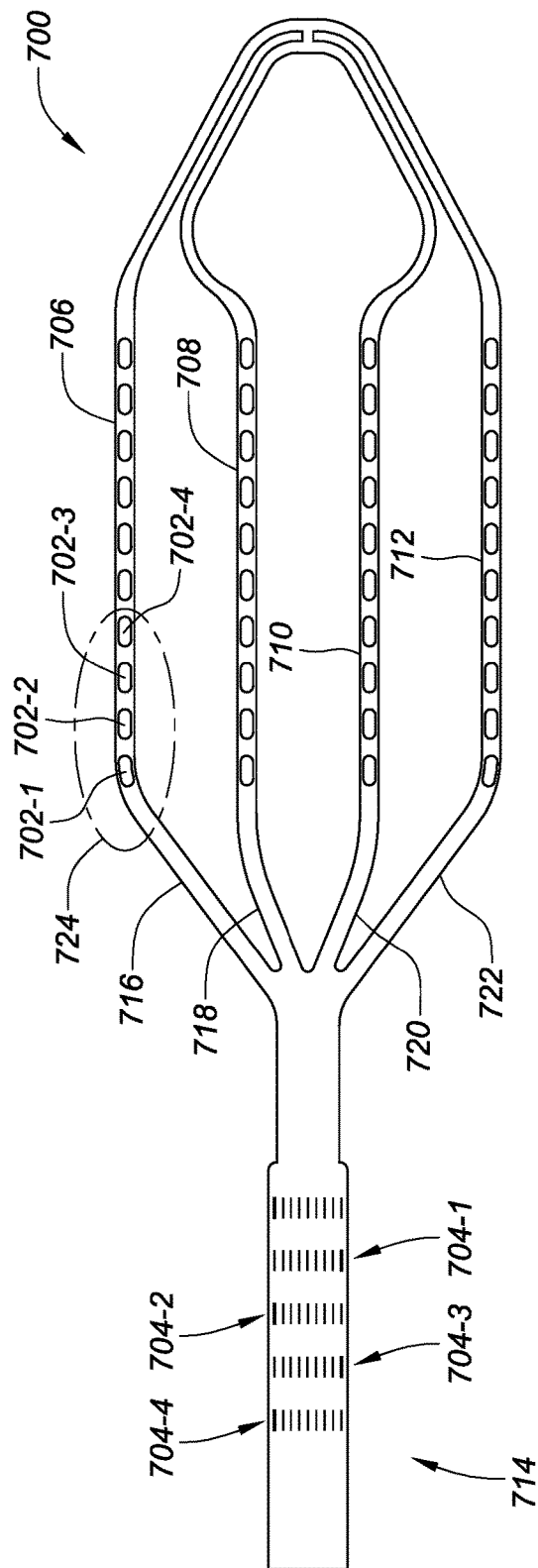
FIG. 25A depicts a top view of an understructure of a flexible tip portion of a high density electrode mapping catheter that includes a plurality of electrodes and rows of contact pads, according to various embodiments of the present disclosure.

FIG. 25A depicts a top view of an understructure of a flexible tip portion 700 of a high density electrode mapping catheter that includes a plurality of electrodes 702-1, 702-2, 702-3, 702-4 and rows of contact pads 704-1, 704-2, 704-3, 704-4, according to various embodiments of the present disclosure. The flexible tip portion 700 can include a first outboard arm 706, second outboard arm 712, first inboard arm 708, and a second inboard arm 710. In some embodiments, the flexible tip portion 700 can include a mounting portion 714 that is connected to the outboard arms 706, 712 via a first outboard transition arm 716 and second outboard transition arm 722. The mounting portion 714 can be connected to the first and second inboard arms 708, 710 via a first inboard transition arm 718 and a second inboard transition arm 720.

Figure 25B:
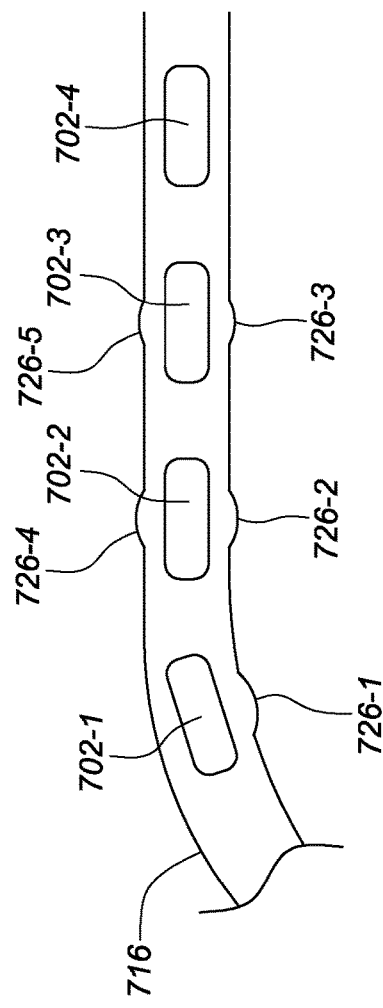
FIG. 25B depicts an enlarged view of the flexible tip portion depicted in FIG. 25A, according to various embodiments of the present disclosure.

As depicted in FIG. 25A, a plurality of electrodes (e.g., electrodes 702-1, 702-2, 702-3, 702-4) can be disposed along the arms of the flexible tip portion 700. FIG. 25B depicts an enlarged view of a portion 724 of the flexible tip portion 700 depicted in FIG. 25A, according to various embodiments of the present disclosure. In some embodiments, portions of the understructure that form the outboard arms 706, 712 and/or the inboard arms 708, 710 can include bumpouts 726-1, 726-1, 726-3, 726-4, 726-5, hereinafter referred to in the plural as bumpouts 726. In some embodiments, the bumpouts 726 can laterally extend from areas of the understructure that include the electrodes 702. As previously discussed in relation to FIG. 24B, traces that proximally extend from each of the electrodes 702 can have routing bends 690 (FIG. 24B). In some embodiments, the routing bends 690 can be disposed on the bumpouts 726.

FIG. 25C depicts an enlarged top view of the mounting portion 714 of the flexible tip portion depicted in FIG. 25A, according to various embodiments of the present disclosure. As depicted, the mounting portion 714 can include flared contact pad portions 730-1, 730-2. In some embodiments, the flared contact pad portions 730-1, 730-2 can increase a lateral width of the mounting portion 714, such that rows of contact pads 704-1, 704-2, 704-3, 704-4 can be disposed on the mounting portion 714, as previously discussed herein. In some embodiments, each row of contact pads 704 can include a plurality of laterally spaced apart contact pads 732-1, 732-2, ..., 732-8. In some embodiments, each row of contact pads 704 can include a common ground 734. In some embodiments, each row of contact pads 704 can correspond to the set of electrodes 702 disposed on the outboard and inboard arms. In an example, a first row of contact pads 704-1 can correspond to microelectrodes disposed on the first outboard arm 706; the second row of contact pads 704-2 can correspond to microelectrodes disposed on the first inboard arm 708; the third row of contact pads 704-3 can correspond to microelectrodes disposed on the second inboard arm 710; and the fourth row of contact pads 704-4 can correspond to microelectrodes disposed on the second outboard arm 712. In some embodiments, as depicted, each row of contact pads 704 can include a ground pad 734, which can serve as a ground for electrodes disposed on a corresponding arm of the flexible tip portion 700. In some embodiments, each row of contact pads 704 can be longitudinally spaced apart from one another, as depicted. Although not depicted, an opposite side of the mounting portion 714 can include additional rows of contact pads. For example, where electrodes are disposed on both sides of the outboard understructure and the inboard understructure, contact pads can be disposed on either side of the mounting portion 714. Contact pads disposed on a first side of the mounting portion 714 can be electrically coupled to electrodes disposed on a first side of the outboard and inboard understructure, while contact pads disposed on a second side of the mounting portion 714 can be electrically coupled to electrodes disposed on a second side of the outboard and inboard understructure.

FIG. 26 depicts a flexible tip portion 740 of a high density electrode mapping catheter similar to that depicted in FIG. 19A that includes a plurality of wires 746 connected to contact pads disposed on a mounting portion 742, according to various embodiments of the present disclosure. In an example, as discussed herein, the flexible tip portion can include a mounting portion 742 upon which a plurality of contact pads are disposed (hidden from view in FIG. 26). In some embodiments, a wire (e.g., wire 746) can be connected to each one of the contact pads, electrically coupling each electrode (e.g., electrode 748) disposed on the flexible tip portion 740 and an associated electrically conductive trace 750 with the wire 746.

Figure 27A:
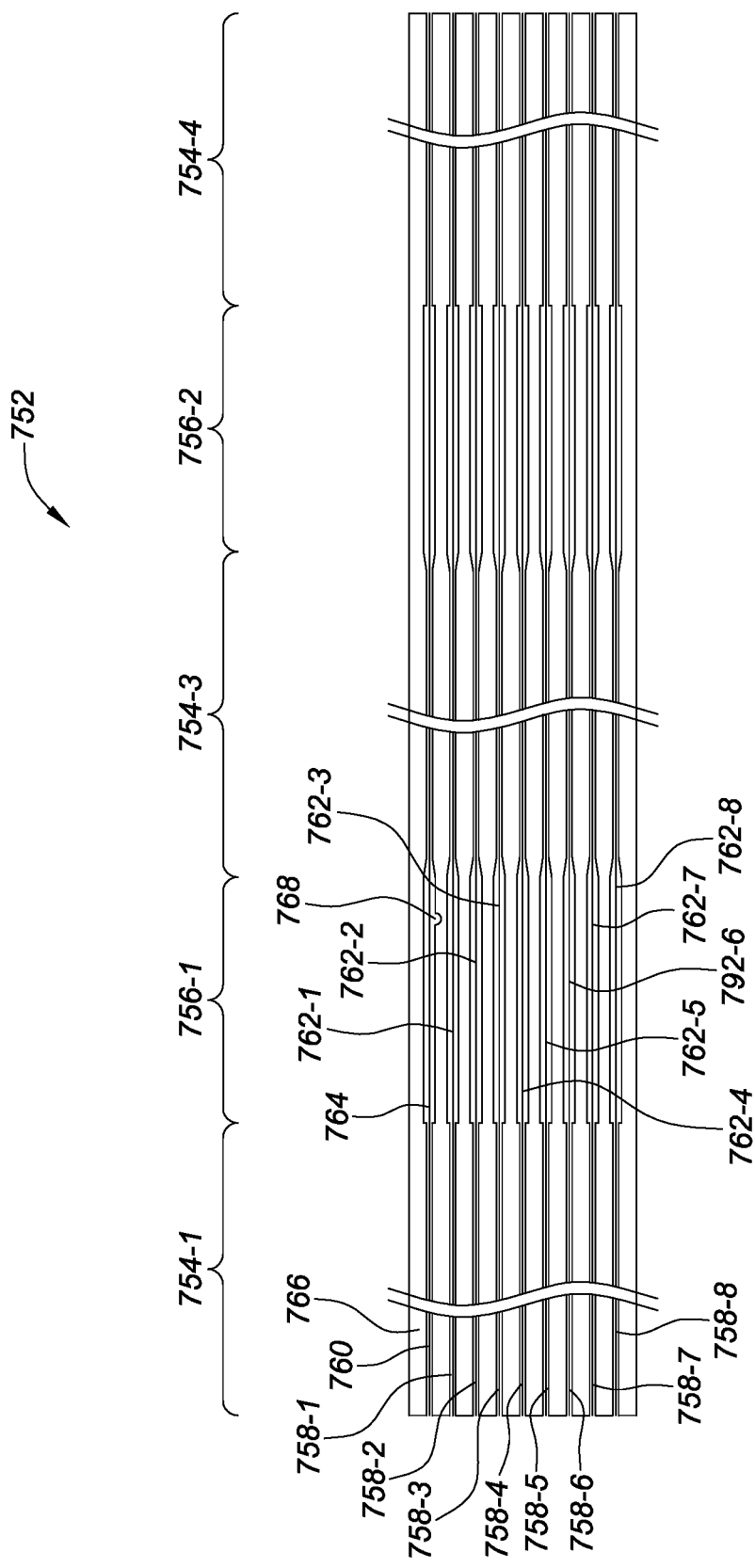
FIG. 27A depicts sections of flex cable, according to various embodiments of the present disclosure.

FIG. 27A depicts sections of flex cable 752, according to various embodiments of the present disclosure. In some embodiments, a first section of flex cable 754-1, a second section of flex cable 754-2, and a third section of flex cable 754-3, hereinafter referred to in the plural as flex cable 754 are depicted. In an example, each section of flex cable includes a plurality of electrically conductive traces. For example, the first section of flex cable 754-1 can include the electrically conductive traces 758-1, 758-2, ..., 758-8, hereinafter referred to in the plural as electrically conductive traces 758. In some embodiments, the plurality of electrically conductive traces 758 can be disposed on a polymer backing 766, as further discussed in relation to FIG. 27B. Additionally, each one of the sections of flex cable can include a ground trace 764 that extends parallel with the electrically conductive traces 758. In some embodiments, test sections 756-1, 756-2 can be disposed between the sections of flex cable 754. In an example, each test section 756-1, 756-2 can include a plurality of test traces 762-1, 762-2, ..., 762-8, hereinafter referred to in the plural as test traces 762, that are connected to each one of the electrically conductive traces 758. In some embodiments, each test section 756-1, 756-2 can also include a ground test trace 764 that is electrically connected to the ground trace 764. In some embodiments, the test traces 762 and the ground test trace 764 can have a wider lateral width than the electrically conductive traces 758 to allow for an instrument to probe the traces of the test section 756. The ground test trace 764 can include a via 768 that extends through the polymer backing 766 and electrically couples the ground test trace 764 to a grounding pad 772 (FIG. 27B).

Figure 27B:
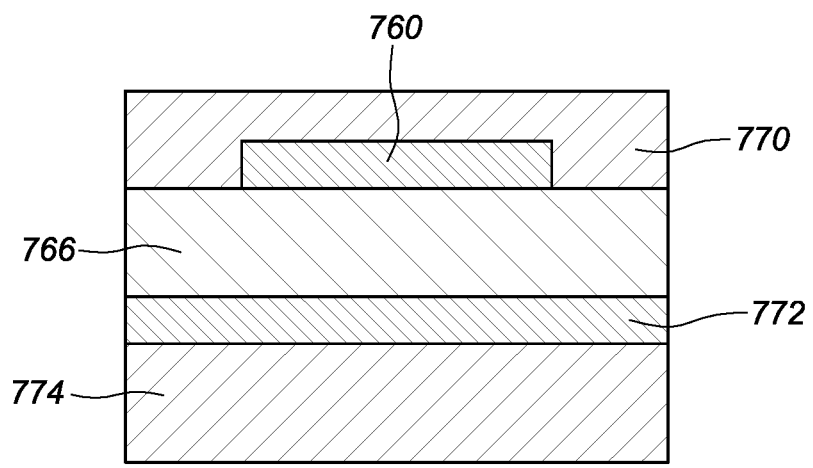
FIG. 27B depicts a cross-sectional end view of a ground trace of the flex cable depicted in FIG. 27A, according to various embodiments of the present disclosure.

In some embodiments, the ground test trace 764 can include a via that electrically connects it to a grounding pad 772, as further depicted in FIG. 27B. FIG. 27B depicts a cross-sectional end view of a ground trace 760 of the flex cable 752 depicted in FIG. 27A, according to various embodiments of the present disclosure. In some embodiments, the ground trace 760 can be formed from copper and can be disposed on top of a polymer backing 766. The ground trace 760 can have a thickness of approximately 10 micrometers, although the thickness of the ground trace 760 can be greater than or less than 10 micrometers. In an example, the polymer backing 766 can be formed from a polyimide. The polymer backing 766 can have a thickness of approximately 25 micrometers, although the thickness of the polymer backing 766 can be greater than or less than 25 micrometers. In some embodiments, each flex cable can have a ground trace 760, providing signal noise reduction and improving electrocardiogram signals that are received by the microelectrodes and passed through the flex cable 752.

In some embodiments, a grounding pad 772 can be disposed on an opposite side of the polymer backing 766 from the ground trace 760. The grounding pad 772 can have a thickness of approximately 12 micrometers, although the thickness of the grounding pad 772 can be greater than or less than 12 micrometers. In some embodiments, as discussed in relation to FIG. 27A, a via (not depicted) can be formed in the polymer backing 766 and can electrically couple the ground trace 760 to the grounding pad 772. In some embodiments, a first layer of polymer 770 can be disposed on a top of the flex circuit and a second layer of polymer 774 can be disposed on a bottom of the flex circuit to protect the traces (e.g., ground trace 760) and/or the grounding pad 772. The first layer of polymer 770 can have a thickness of approximately 15 micrometers, although the thickness of the first layer of polymer 770 can be greater than or less than 15 micrometers. The second layer of polymer 774 can have a thickness of approximately 25 micrometers, although the thickness of the second layer of polymer 774 can be greater than or less than 15 micrometers. In some embodiments, the first and second layer of polymer can include a polymer, such as a polymer selected from a Dissipation Factor-Photo Sensitive Resist (DF-PSR) group of materials.

In some embodiments, one or more flex cables 752 can be electrically coupled with microelectrodes disposed on a flexible tip portion of a high density electrode mapping catheter, as discussed herein. As depicted, the flex cable 752 can include eight test traces 762 and a common ground. In some embodiments, five flex cables can be attached to each side of the flexible tip portion of the high density electrode mapping catheter to allow for forty microelectrodes per side of the flexible tip portion. This can save time and resources as a result of providing a semi-automated process versus the individual soldering of forty contacts per side. In an example, each flex cable 752 can have a mating pattern on a contact pad disposed on the flexible tip portion. For example, the flex cable 752 can be mated with a row of contact pads 704 (FIG. 25C).

Figure 28:
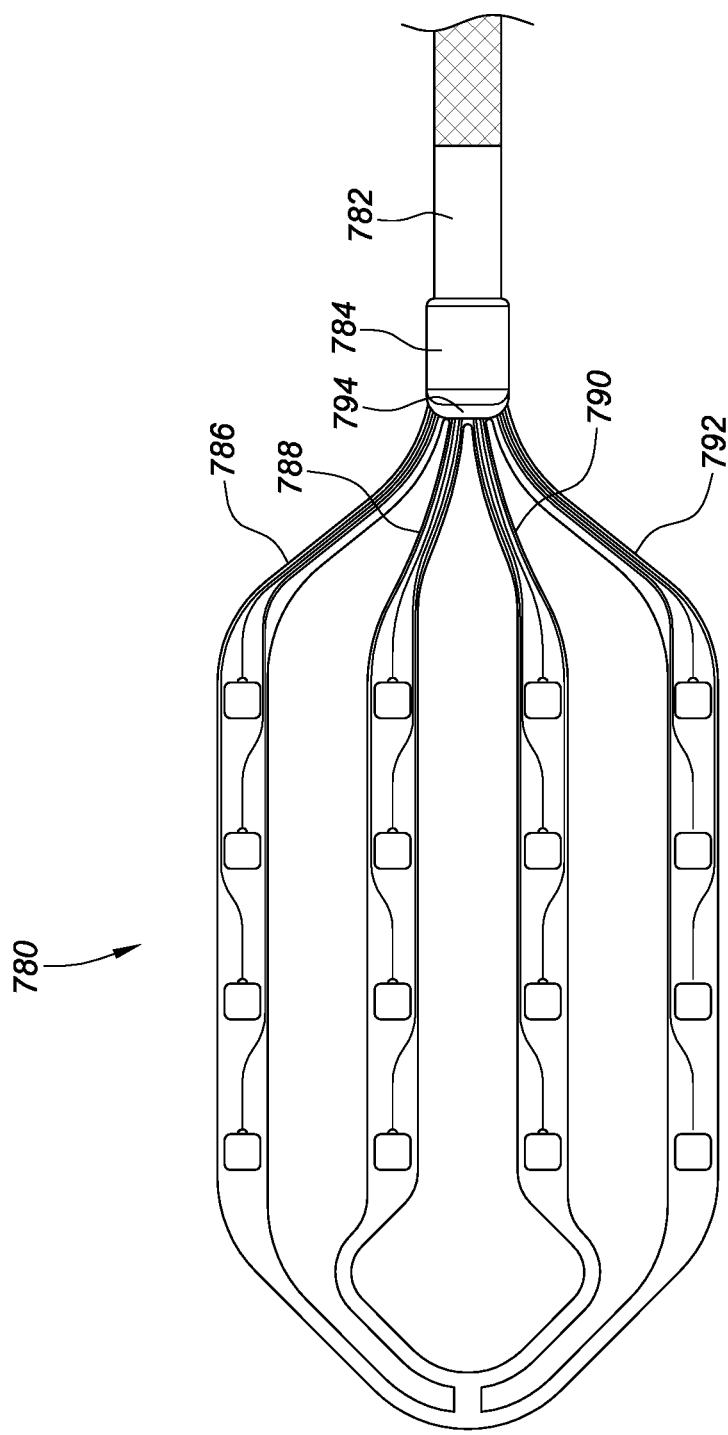
FIG. 28 depicts a flexible tip portion of a high density electrode mapping catheter disposed in a distal end of a catheter shaft, according to various embodiments of the present disclosure.

FIG. 28 depicts a flexible tip portion 780 of a high density electrode mapping catheter disposed in a distal end of a catheter shaft 782, according to various embodiments of the present disclosure. The flexible tip portion 780 of the high density electrode mapping catheter can include those features as discussed herein. As depicted, a proximal portion of the flexible tip portion 780 is disposed in the distal end of the catheter shaft 782. Although not depicted, a mounting portion of the flexible tip portion 780, as discussed herein, can be disposed in a lumen defined by the distal end of the catheter shaft 782. In some embodiments, a connector 784 can be disposed at the distal end of the catheter shaft 782 and can connect the flexible tip portion 780 to the distal end of the catheter shaft 782. As depicted, a first outboard transition arm 786, a second outboard transition arm 792, a first inboard transition arm 788, and a second inboard transition arm 790 can extend distally from the connector 784 and the distal end of the catheter shaft 782. In some embodiments, and as depicted, an adhesive 794 (e.g., epoxy) can be disposed around the proximal end of the transitional arms and the connector 784 to secure the flexible tip portion 780 with the catheter shaft 782.

Figure 29:
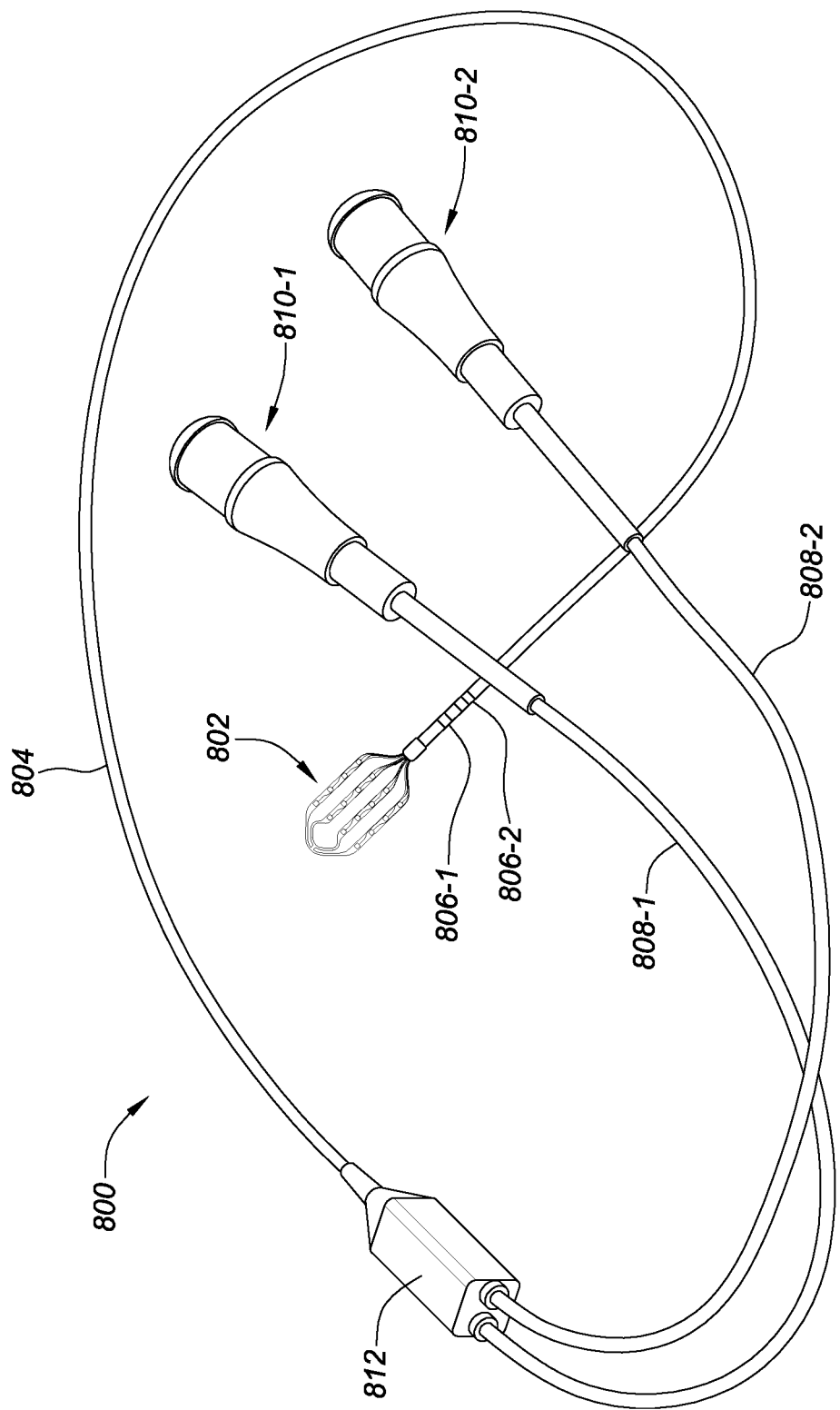
FIG. 29 depicts a high density electrode mapping catheter, according to various embodiments of the present disclosure.

FIG. 29 depicts a high density electrode mapping catheter 800, according to various embodiments of the present disclosure. In some embodiments, the high density electrode mapping catheter 800 can include a flexible tip portion 802 disposed at a distal end of a catheter shaft 804. In some embodiments, the catheter shaft 804 can include one or more ring electrodes 806-1, 806-2, as discussed herein. In some embodiments, the flexible tip portion 802 can include electrodes disposed on both sides of the flexible tip portion 802. In some embodiments, a cable to shaft coupler can be disposed at a proximal end of the catheter shaft 804 and can couple a first sensing cable 808-1 and a second sensing cable 808-2 with the catheter shaft. In some embodiments, the first sensing cable 808-1 can include electrical connections for electrodes disposed on a first side of the flexible tip portion 802 and the second sensing cable 808-2 can include electrical connections for electrodes disposed on a second side of the flexible tip portion 802. In some embodiments, the first sensing cable 808-1 can include electrical connections for the electrodes disposed on the flexible tip portion 802 and the second sensing cable 808-2 can include electrical connections for the ring electrodes 806-1, 806-2. In some embodiments, a proximal end of the first and second sensing cables 808-1, 808-2 can include a first and second connector 810-1, 810-2, which can be connected to a computer configured to analyze signals received from the electrodes disposed on the flexible tip portion 802.

Figure 30:
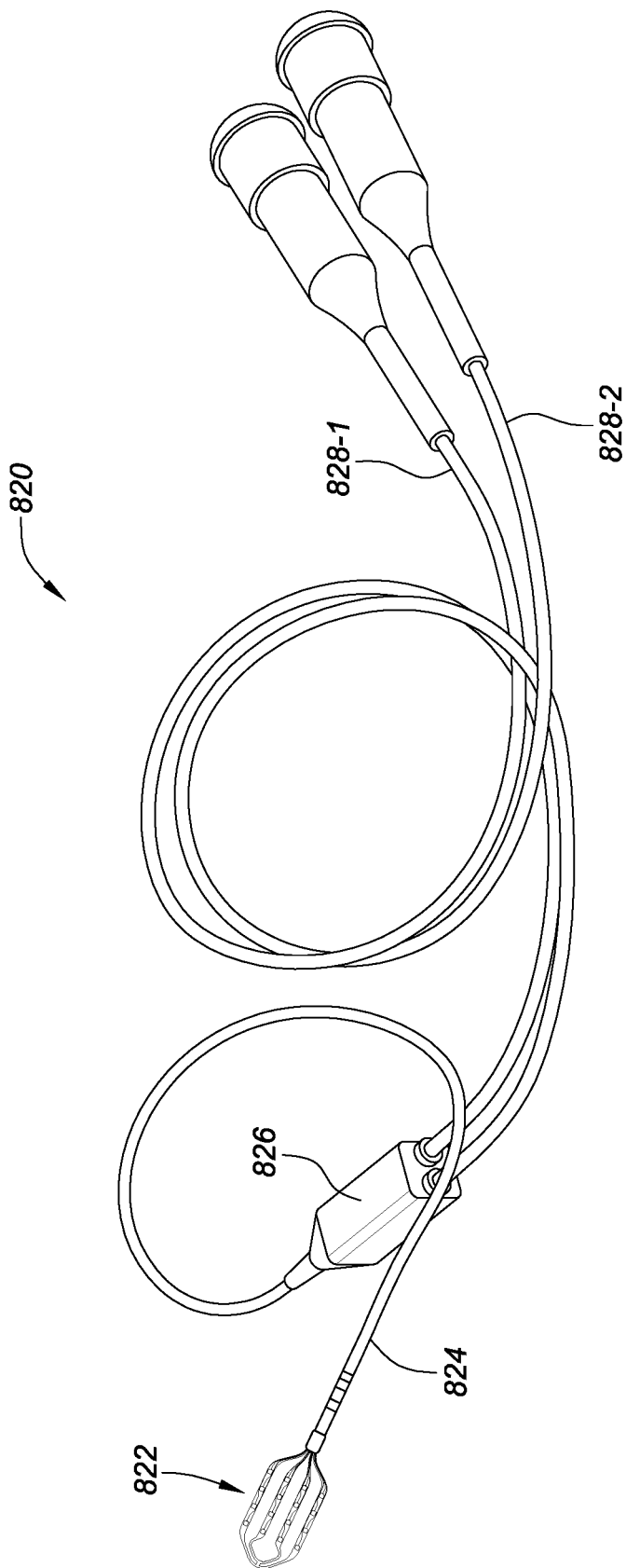
FIG. 30 depicts another embodiment of a high density electrode mapping catheter, according to various embodiments of the present disclosure.

FIG. 30 depicts another embodiment of a high density electrode mapping catheter 820, according to various embodiments of the present disclosure. In some embodiments, the high density electrode mapping catheter 820 can include a flexible tip portion 822 disposed at a distal end of a catheter shaft 824. In contrast to FIG. 29, the catheter shaft 824 does not include ring electrodes. In some embodiments, the flexible tip portion 822 can include electrodes disposed on both sides of the flexible tip portion 822. In some embodiments, a cable to shaft coupler 826 can be disposed at a proximal end of the catheter shaft 824 and can couple a first sensing cable 828-1 and a second sensing cable 828-2 with the catheter shaft 824. In some embodiments, the first sensing cable 828-1 can include electrical connections for electrodes disposed on a first side of the flexible tip portion 822 and the second sensing cable 828-2 can include electrical connections for electrodes disposed on a second side of the flexible tip portion 822. In some embodiments, a proximal end of the first and second sensing cables 828-1, 828-2 can include a first and second connector 820-1, 820-2, which can be connected to a computer configured to analyze signals received from the electrodes disposed on the flexible tip portion 822.

Figure 31:
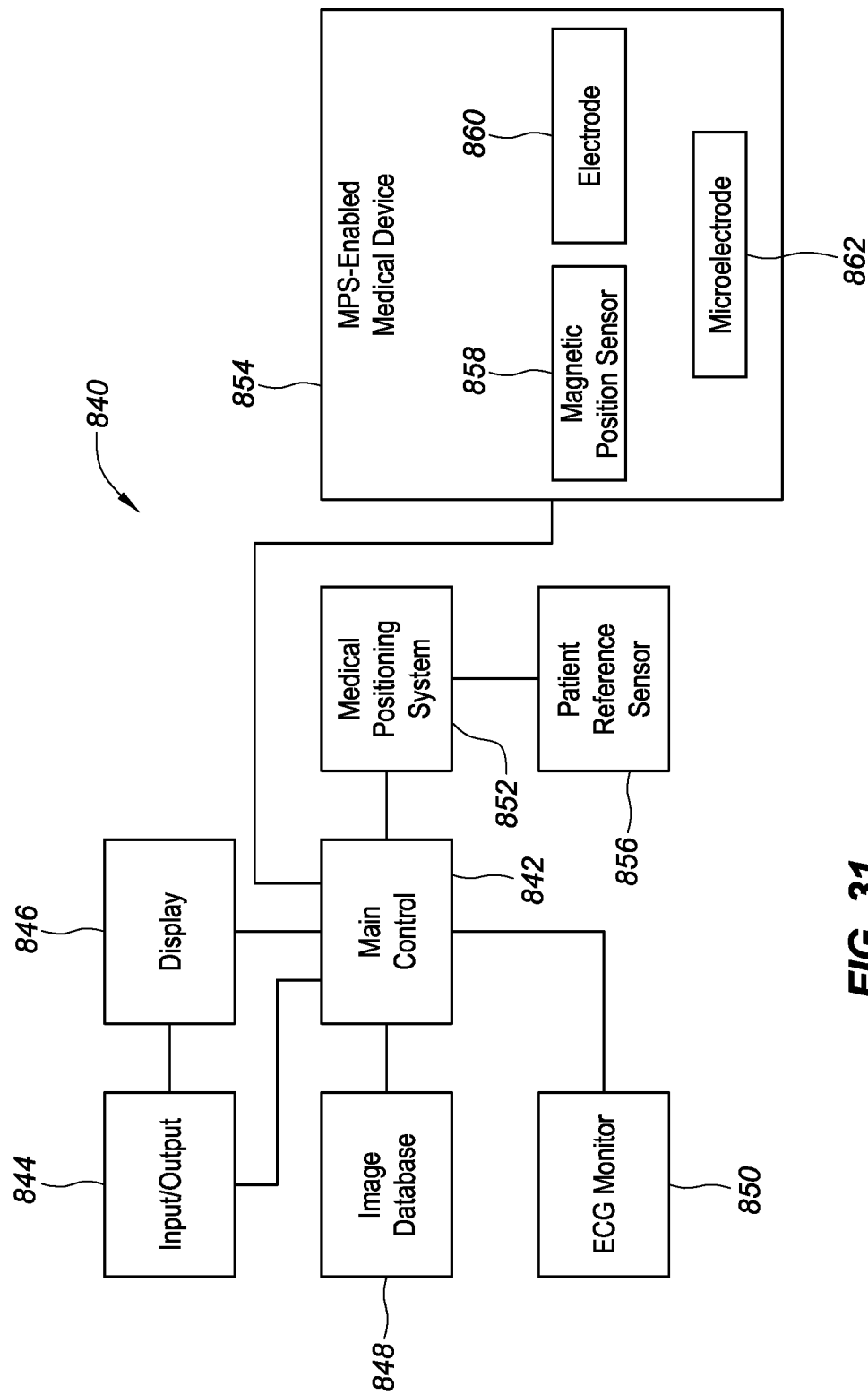
FIG. 31 depicts a schematic and block diagram view of an electromagnetic navigation system, according to various embodiments of the present disclosure.

FIG. 31 depicts a schematic and block diagram view of a medical system 840, in accordance with embodiments of the present disclosure. System 840, as depicted, includes a main electronic control unit 842 (e.g., a processor) having various input/output mechanisms 844, a display 846, an optional image database 848, an electrocardiogram (ECG) monitor 850, a localization system, such as a medical positioning system 852, a medical positioning system-enabled elongate medical device 854, a patient reference sensor 856, a magnetic position sensor 858, an electrode 860 (e.g., position sensing electrode), and a microelectrode 862 configured to sense electrical signals produced by the heart. For simplicity, one magnetic position sensor 858, one electrode 860, and one microelectrode 862 are shown, however, more than one magnetic position sensor 858, more than one electrode 860, and/or more than one microelectrode 862 can be included in the system 300.

Input/output mechanisms 844 may comprise conventional apparatus for interfacing with a computer-based control unit including, for example, one or more of a keyboard, a mouse, a tablet, a foot pedal, a switch and/or the like. Display 846 may also comprise conventional apparatus, such as a computer monitor.

System 840 may optionally include image database 848 to store image information relating to the patient's body. Image information may include, for example, a region of interest surrounding a destination site for medical device 854 and/or multiple regions of interest along a navigation path contemplated to be traversed by medical device 854. The data in image database 848 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 314. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 850 is configured to continuously detect an electrical timing signal of the heart organ through the use of a plurality of microelectrodes 862. The timing signal generally corresponds to a particular phase of the cardiac cycle, among other things. Generally, the ECG signal(s) may be used by the control unit 842 for ECG synchronized playback of a previously captured sequence of images (cine loop) stored in database 848. ECG monitor 850 and ECG-electrodes may both comprise conventional components. In some embodiments, the main control 842 can include a computing device, which can include hardware and/or a combination of hardware and programming that is configured to determine a difference in signals received by microelectrodes, as discussed in relation to FIG. 19D. For example, the main control 842 can include a non-transitory computer readable medium that stores instructions, which are executable by a processor, in communication with the main control 842, to determine a difference in signals received from microelectrodes. Medical positioning system 852 is configured to serve as the localization system and therefore to determine position (localization) data with respect to one or more magnetic position sensors 858 and/or electrodes 860 and output a respective location reading.

Figure 32:
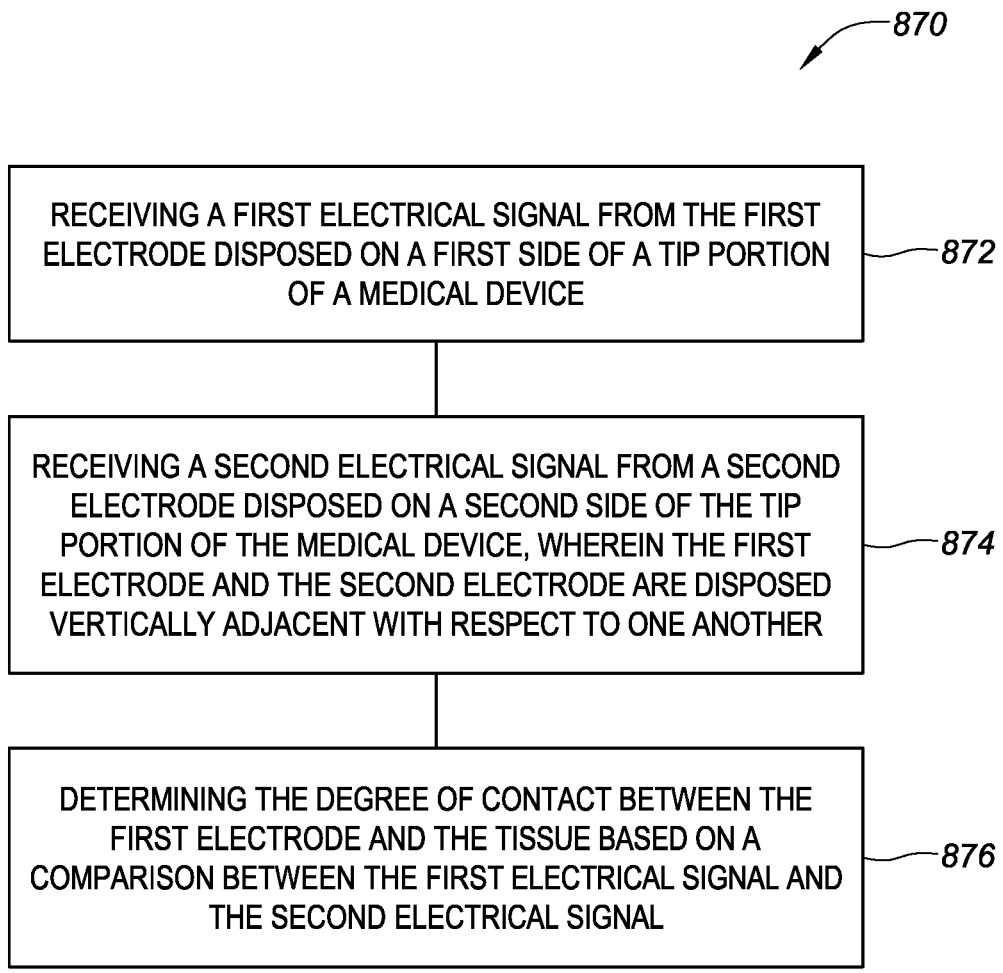
FIG. 32 depicts a method control block flow diagram for determining a degree of contact between a first electrode and tissue, according to various embodiments of the present disclosure.

FIG. 32 depicts a method 870 control block flow diagram for determining a degree of contact between a first electrode and tissue, according to various embodiments of the present disclosure. In some embodiments, as previously discussed herein, for example in relation to FIG. 19D, the method 870 can include receiving a first electrical signal from the first electrode disposed on a first side of a tip portion of a medical device, at method control block 872. The method 870 can further include receiving a second electrical signal from a second electrode disposed on a second side of the tip portion of the medical device, at method control block 874. As previously discussed, the first electrode and the second electrode can be disposed vertically adjacent with respect to one another. For example, the first electrode can be disposed directly beneath the second electrode, as depicted and discussed in relation to FIG. 19D.

In some embodiments, the method 870 can include determining the degree of contact between the first electrode and the tissue based on a comparison between the first electrical signal and the second electrical signal, at method control block 876. In an example, when the first electrode is disposed against tissue, the second electrode can be disposed on the opposite side of the medical device and in a blood pool. As such, a different electrical signal (e.g., voltage) can be received from the first electrode versus the second electrode. Accordingly, in some embodiments, the comparison between the first electrical signal and the second electrical signal can include comparing a first voltage associated with the first electrical signal and a second voltage associated with the second electrical signal.

In an example, cardiac tissue can generate a voltage whenever it depolarizes. The voltage can propagate through the heart muscle and also through the blood pool and can be picked up by both the first electrode and the second electrode. If one of the electrodes (e.g., first electrode) is touching the tissue, then that voltage will be different than the voltage picked up by the electrode disposed in the blood pool (e.g., second electrode). The difference between the first electrical signal associated with the first electrode and the second electrical signal associated with the second electrode will be greater when the first electrode is touching the tissue and the second electrode is disposed in the blood pool. The difference between the first electrical signal associated with the first electrode and the second electrical signal associated with the second electrode will be smaller when the first electrode and second electrode are both disposed in the blood pool.

Based on the differences in electrical signals (e.g., voltages), a determination of contact between the medical device (e.g., first electrode) and the tissue can be made. For example, the method 870 can include determining that the first electrode is not in contact with the tissue when the first voltage associated with the first electrical signal and the second voltage associated with the second electrical signal are the same. For example, when the voltages associated with the first electrode and the second electrode are the same, this can be an indication that the first electrode and the second electrode are disposed in the blood pool and are not in contact with the tissue. In some embodiments, the method can include determining that the first electrode is not in contact with the tissue when a difference between the first voltage associated with the first electrical signal and the second voltage associated with the second electrical signal is less than a threshold voltage (e.g., the voltages are close to being the same). For example, the voltages associated with each of the first and second electrodes may not be exactly the same due to electrical interference in the blood pool.

Alternatively, in some embodiments, the method 879 can include determining that the first electrode is in contact with the tissue when the first voltage associated with the first electrical signal is different than the second voltage associated with the with the second electrical signal. In an example, the method 879 can include determining that the first electrode is in contact with the tissue when a difference between the first voltage associated with the first electrical signal and the second voltage associated with the second electrical signal is greater than a threshold value. For instance, the method 879 can include determining that the first electrode is in contact with the tissue when the first voltage associated with the first electrical signal is greater than the second voltage associated with the second electrical signal (e.g., is greater than a defined threshold value). As discussed, when the first electrode is disposed against the tissue and the second electrode is disposed in the blood pool, the first electrical signal associated with the first electrode can have a greater voltage than the second electrical signal.

In some embodiments, the method 870 can include determining that a degree of contact between the first electrode and the tissue is increasing based on the first voltage associated with the first electrical signal being increased with respect to the second voltage associated with the second electrical signal. For example, if the first voltage associated with the first electrical signal increases at a greater rate than the second voltage associated with the second electrical signal and/or increases while the second voltage stays the same, a determination can be made that a degree of contact between the first electrode and the tissue is increasing. In some embodiments, ensuring that sufficient contact exists between the medical device and the tissue can be beneficial where diagnostic information is being collected by the medical device (e.g., electrodes) and/or therapeutic energy is being delivered to the tissue from the medical device (e.g., electrodes). Alternatively, the method 870 can include determining that a degree of contact between the first electrode and the tissue is decreasing based on the first voltage associated with the first electrical signal being decreased with respect to the second voltage associated with the second electrical signal.

In some embodiments, the first and/or second electrode can be configured to be driven by an electrical current (e.g., high frequency electrical current). In an example, the first and/or second electrode can be driven with the electrical current and a voltage (e.g., high frequency voltage) can be induced by the electrical current. For instance, a voltage can be induced in the cardiac tissue and/or in the blood pool. Accordingly, an induced voltage, which is generated by one or more of the electrodes, rather than the heart, can be received by one or more of the electrodes on the medical device. The induced voltage (e.g., impedance) associated with an electrical signal received from one of the electrodes can be measured. Depending on whether an electrode from which the electrical signal is received is disposed in the blood pool or is in contact with the tissue, the electrical signal can vary. In an example, the induced voltages that are measured from an electrical signal received from the first electrode and the second electrode can be different if one of the electrodes is disposed against tissue and one of the electrodes is disposed in the blood pool and can be similar if both electrodes are disposed in the blood pool.

In some embodiments, one or both of the first electrode and the second electrodes can be driven with the current and one or more other electrodes disposed on the medical device or an electrode disposed on a skin patch can receive an induced voltage. In some embodiments, the current can be induced in the first electrode and an induced voltage can be received by the second electrode. Depending on whether the second electrode is disposed in the blood pool or in contact with cardiac tissue can affect a magnitude of the induced voltage. Likewise, the current can be induced in the second electrode and an induced voltage can be received by the first electrode. Depending on whether the first electrode is disposed in the blood pool or in contact with cardiac tissue can affect a magnitude of the induced voltage. In some embodiments, a current can be induced in another electrode disposed on the medical device and an induced voltage can be received by one or both of the first and second electrodes. Induced voltages associated with electrical signals received from the first and second electrodes can vary depending on whether one or more of the first and second electrodes are disposed in the blood pool or disposed against cardiac tissue, as discussed herein.

Figure 33:
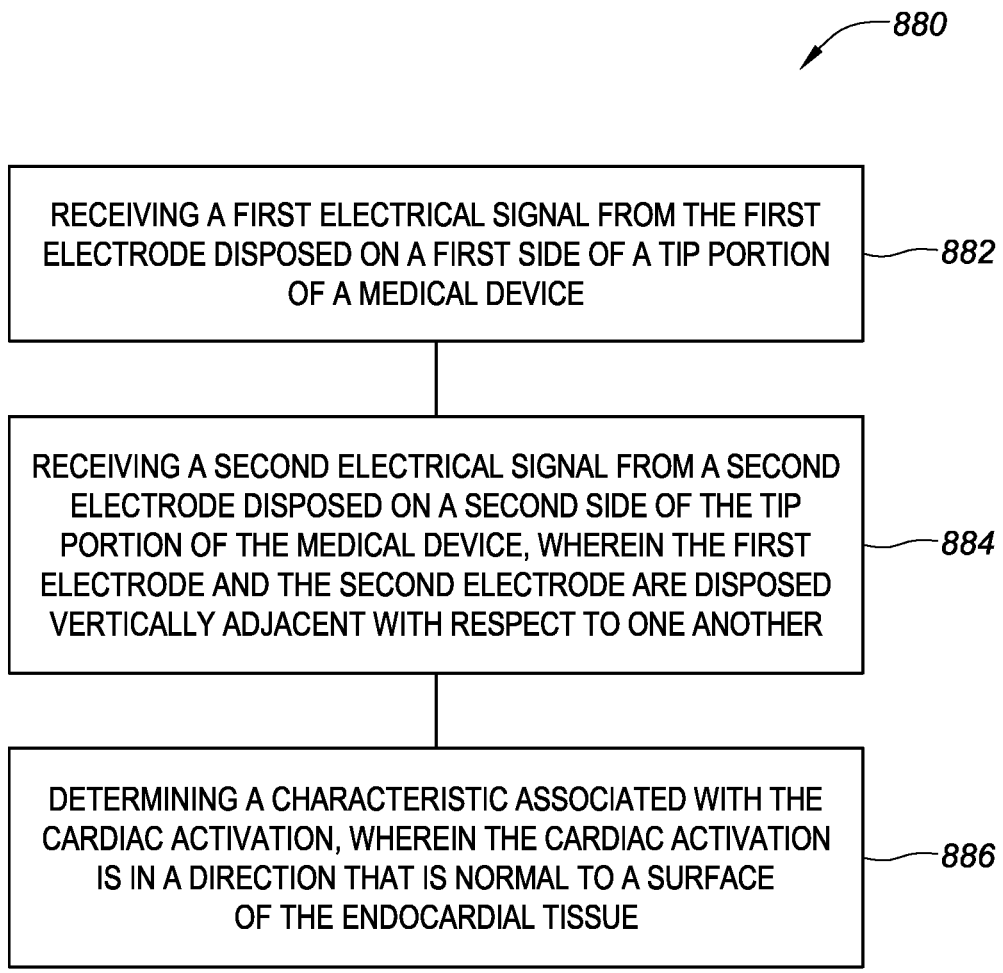
FIG. 33 depicts a method control block flow diagram for determining a cardiac activation associated with endocardial tissue, according to various embodiments of the present disclosure.

FIG. 33 depicts a method 880 control block flow diagram for determining a cardiac activation associated with endocardial tissue, according to various embodiments of the present disclosure. As discussed in relation to FIG. 33, the method 880 can include receiving a first electrical signal from a first electrode disposed on a first side of a tip portion of a medical device, at method control block 882. In some embodiments, the method 880 can include receiving a second electrical signal from a second electrode disposed on a second side of the tip portion of the medical device, at method control block 884. As previously discussed, the first electrode and the second electrode can be disposed vertically adjacent with respect to one another in a manner analogous to that depicted and discussed in relation to FIG. 19D.

In some embodiments, the method 880 can include determining a characteristic associated with the cardiac activation, wherein the cardiac activation is in a direction that is normal to a surface of the endocardial tissue, at method control block 886. In an example, because the first electrode and the second electrode are vertically adjacent to one another, as a cardiac activation travels through endocardial tissue, an electrical activation signal can be received by the first electrode disposed against the tissue and can then be received by the second electrode that is vertically adjacent to the first electrode. For instance, as the electrical activation signal travels toward a surface of the endocardial tissue on which the first electrode is disposed, the electrical activation signal can travel in a direction that is normal to the surface of the endocardial tissue, toward the first electrode. As the electrical activation signal reaches the surface of the endocardial tissue on which the first electrode is disposed, a first electrical signal can be received from the first electrode. The electrical activation signal can then travel through a portion of the blood pool and can be received by the second electrode disposed vertically adjacent to the first electrode. This can allow for a better measurement of the electrical activation signal since the two electrodes are disposed vertically adjacent to one another.

In some embodiments, the characteristic associated with the cardiac activation can include a direction of the cardiac activation. For example, a determination that a component of a directional vector of the cardiac activation is normal to a surface of the endocardial tissue can be made. In some embodiments, it can be common for cardiac activation to be in a direction that is normal to the surface of the endocardial tissue. For example, in thick ventricular tissue, cardiac activation can be in a direction that is normal to the surface of the endocardial tissue.

In some embodiments, the method 880 can include filtering out noise from the first electrical signal based on the second electrical signal. For example, where the first electrode is disposed against the surface of the endocardial tissue, surrounding noise can have negative effects on the first electrical signal associated with the first electrode. The surrounding noise can be caused by stray electrical signals that are flowing through the blood pool in some embodiments. Accordingly, the second electrode, which is disposed in the blood pool can receive any stray electrical signals that are flowing through the blood pool, which can be represented in the second electrical signal associated with the second electrode. In some embodiments, the second electrical signal can be used to filter out the stray electrical signals from the first electrical signal.

In some embodiments, the method 870 and method 880 can be executed by a computer such as that discussed in relation to FIG. 31. In some embodiments, the method control blocks (e.g., control blocks 872, 874, 876, 882, 884, 886) can represent computer executable instructions that can be stored on a non-transitory computer readable medium (CRM), which can be executed by a processor in communication with the computer to perform a particular function (e.g., receive a first electrical signal from the first electrode disposed on a first side of a tip portion of a medical device).

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a high density electrode mapping catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for forming an integrated electrode structure, comprising:

forming a flexible tip portion of a flexible framework from a planar substrate, wherein the flexible tip portion includes an inner understructure and an outer understructure each having a top surface and bottom surface;

coating the flexible tip portion of the flexible framework of the integrated electrode structure with a first dielectric material;

masking a trace pattern on the coated flexible framework with a masking material to form a masked portion and an unmasked trace pattern portion;

depositing a seed layer on the unmasked trace pattern portion;
plating the seed layer with a conductive material to form an electrically conductive trace;
stripping the masking material from the masked portion;
coating the electrically conductive trace with a second dielectric material;
stripping the second dielectric material from a distal portion of the electrically conductive trace; and
electrically connecting an electrode to the distal portion of the electrically conductive trace;
wherein the integrated electrode structure comprises a first array of electrodes patterned onto the top surfaces of the inner and outer understructures and a second array of electrodes patterned onto the bottom surfaces of the inner and outer understructures, wherein the first array of electrodes is parallel with the second array of electrodes and each electrode in the first and second array of electrodes are longitudinally aligned with one another when the flexible tip is an expanded configuration.

2. The method of claim 1, wherein electrically connecting the electrode to the distal portion of the electrically conductive trace includes:
masking the flexible framework of the integrated electrode structure proximally and distally with respect to the distal portion of the electrically conductive trace to form a mask defined area;
depositing a second seed layer across the mask defined area; and
plating the mask defined area with an electrically conductive material to form the electrode.

3. The method of claim 2, further comprising stripping masked portions of the flexible framework.

4. The method of claim 2, wherein the seed layer is a conductive metal selected from the group consisting of copper, nickel, and aluminum.

5. The method of claim 1, wherein the electrode is formed from gold.

6. The method of claim 1, further comprising circumferentially masking the flexible framework of the integrated electrode structure proximally and distally with respect to the distal portion of the electrically conductive trace to form a circumferential mask defined area.

7. The method of claim 6, further comprising circumferentially plating the circumferential mask defined area with the electrically conductive material to form a circumferential electrode.

8. The method of claim 7, wherein the circumferential electrode is coaxial with the flexible framework of the flexible tip portion.

9. The method of claim 7, wherein the method further comprises overmolding the integrated electrode structure with a polymer.

10. The method of claim 9, wherein the method further comprises removing the polymer from an outer surface of the electrode.

11. A method for forming an integrated electrode structure, comprising:
coating a flexible tip portion of a flexible framework of the integrated electrode structure with a first dielectric material;
masking a trace pattern on the coated flexible framework with a masking material to form a masked portion and an unmasked trace pattern portion;
depositing a seed layer on the unmasked trace pattern portion;
plating the seed layer with a conductive material to form an electrically conductive trace;
stripping the masking material from the masked portion;
coating the electrically conductive trace with a second dielectric material;
stripping the second dielectric material from a distal portion of the electrically conductive trace;
electrically connecting an electrode to the distal portion of the electrically conductive trace; and
electrically connecting a hollow cylindrical band to the distal portion of the electrically conductive trace by depositing solder on the distal portion of the electrically conductive trace, wherein electrically connecting the hollow cylindrical band to the distal portion of the electrically conductive trace includes coaxially aligning the hollow cylindrical band with the distal portion of the electrically conductive trace and the flexible framework.

12. The method of claim 11, wherein the hollow cylindrical band is coaxial with the flexible framework of the flexible tip portion.

13. The method of claim 11, wherein electrically connecting the hollow cylindrical band to the distal portion of the electrically conductive trace further includes reflowing the solder to electrically couple the hollow cylindrical band with the distal portion of the electrically conductive trace.

14. A method for forming an integrated electrode structure, comprising:
forming a flexible tip portion of a flexible framework from a planar substrate, wherein the flexible tip portion includes an inner understructure and an outer understructure each having a top surface and bottom surface;
coating the flexible tip portion of the flexible framework of the integrated electrode structure with a conductive material;
masking a trace pattern on the coated flexible framework with a masking material to form a masked trace pattern portion and an unmasked portion;
etching the unmasked portion to expose the flexible framework substrate;
stripping the masking material from the masked trace pattern portion to expose an electrically conductive trace;
coating the electrically conductive trace with a dielectric material;
stripping the dielectric material from a distal portion of the electrically conductive trace; and
electrically connecting an electrode to the distal portion of the electrically conductive trace;
wherein the integrated electrode structure comprises a first array of electrodes patterned onto the top surfaces of the inner and outer understructures and a second array of electrodes patterned onto the bottom surfaces of the inner and outer understructures, wherein the first array of electrodes is parallel with the second array of electrodes and each electrode in the first and second array of electrodes are longitudinally aligned with one another when the flexible tip is an expanded configuration.

15. The method of claim 14, wherein the method further comprises overmolding the integrated electrode structure with a polymer.

16. The method of claim 15, wherein the method further comprises removing the polymer from an outer surface of the electrode.

17. The method of claim 16, wherein removing the polymer from the outer surface of the electrode includes removing the polymer via an ablating step.

* * * * *